US007470777B2

(12) United States Patent
McCray, Jr. et al.

(10) Patent No.: US 7,470,777 B2
(45) Date of Patent: Dec. 30, 2008

(54) COMPOSITIONS AND METHODS RELATED TO MODIFIED RETROVIRAL VECTORS FOR RESTRICTED, SITE SPECIFIC INTEGRATION

(75) Inventors: Paul B. McCray, Jr., Iowa City, IA (US); Patrick L. Sinn, Iowa City, IA (US); Daniel F. Voytas, Ames, IA (US); Junbiao Dai, Ames, IA (US)

(73) Assignees: Iowa State University Research Foundation, Inc., Ames, IA (US); University of Iowa Research Foundation, Iowa City, IA (US)

( * ) Notice: Subject to any disclaimer, the term of this patent is extended or adjusted under 35 U.S.C. 154(b) by 8 days.

(21) Appl. No.: 11/317,330

(22) Filed: Dec. 22, 2005

(65) Prior Publication Data
US 2006/0154240 A1 Jul. 13, 2006

Related U.S. Application Data

(60) Provisional application No. 60/638,590, filed on Dec. 22, 2004.

(51) Int. Cl.
*A61K 39/385* (2006.01)
*A61K 39/12* (2006.01)
*A61K 39/21* (2006.01)
*C07K 14/00* (2006.01)
*A61K 39/00* (2006.01)

(52) U.S. Cl. ................. 530/402; 424/204.1; 424/193.1; 424/207.1

(58) Field of Classification Search ........................ None
See application file for complete search history.

(56) References Cited

U.S. PATENT DOCUMENTS

| | | | | |
|---|---|---|---|---|
| 5,339,346 | A | 8/1994 | White | 378/34 |
| 5,830,707 | A | 11/1998 | Bushman | 435/69.7 |
| 5,976,795 | A | 11/1999 | Voytas et al. | 435/6 |
| 6,150,511 | A | 11/2000 | Katz et al. | 536/23.1 |
| 6,228,647 | B1 | 5/2001 | Voytas et al. | 435/455 |
| 6,720,181 | B1 | 4/2004 | Chiaur et al. | 435/325 |
| 2001/0043921 | A1 | 11/2001 | Gunzburg et al. | 424/93.21 |
| 2003/0003567 | A1 | 1/2003 | Barber et al. | 435/235.1 |
| 2003/0119023 | A1 | 6/2003 | Choo et al. | 435/6 |
| 2004/0110923 | A1 | 6/2004 | Moore et al. | 530/350 |

FOREIGN PATENT DOCUMENTS

| | | |
|---|---|---|
| WO | WO 96/06166 | 2/1996 |
| WO | WO 98/53057 | 11/1998 |
| WO | WO 98/53058 | 11/1998 |
| WO | WO 98/53060 | 11/1998 |
| WO | WO 99/07389 | 2/1999 |
| WO | WO 2004/009792 | 1/2004 |

OTHER PUBLICATIONS

Saenz et al., FIV: from lentivirus to lentivector, 2004, The Journal of Gene Medicine, vol. 6, pp. S95-S104.*
Priet et al., JBC Papers in Press. Published on Nov. 27, 2002 as Manuscript M209311200, 27 pages.*
Dvorin et al., Reassessment of the Roles of Integrase and the Central DNA Flap in Human Immunodeficiency Virus Type 1 Nuclear Import, 2002, Journal of Virology, vol. 76, No. 23, pp. 12087-12096.*
Van Maele et al., Impact of the Central Polypurine Tract on the Kinetics of Human Immunodeficiency Virus Type 1 Vector Transduction, 2003, Journal of Virology, vol. 77, No. 8, pp. 4685-4694.*
Whitwam et al., Identification of a Central DNA Flap in Feline Immunodeficiency Virus, 2001, Journal of Virology, vol. 75, No. 19, pp. 9407-9414.*
Brooks et al., "Functional correction of established central nervous system deficits in an animal model of lysosomal storage disease with feline immunodeficiency virus-based vectors," *Proc. Natl. Acad. Sci. USA*, 99: 6216-8221., 2002.
Bushman and Miller, "Tethering human immunodeficiency virus type 1 preintegration complexes to target DNA promotes integration at nearby sites," *J. Virol.*, 71: 458-464, 1997.
Bushman, "Integration site selection by lentiviruses: biology and possible control," *Current Topics in Microbiology & Immunology*, 261: 165-77, 2002.
Bushman, "Tethering human immunodeficiency virus 1 integrase to a DNA site directs integration to nearby sequences," *Proc. Natl. Acad. Sci. USA*, 91(20):9233-92337, 1994.
Bushman, "Targeting retroviral integration," *Science*, 267(5203):1443-1444, 1995.
Busschots et al., "The interaction of LEDGF/p75 with integrase is lentivirus-specific and promotes DNA binding," *J. Biol. Chem.*, 280:17841-7, 2005.
Cavazzana-Calvo et al., "Gene therapy of human severe combined immunodeficiency (SCID)-X1 disease," *Science*, 288: 669-72, 2000.
Ciuffi et al., "A role for LEDGF/p75 in targeting HIV DNA integration," *Nat. Med.*, 11:1287-9, 2005.
Derksen et al., "Feline immunodeficiency virus vectors. Gene transfer to mouse retina following intravitreal injection," *J. Gene Med.*, 4: 463-469., 2002.
Espanel and Sudol, "Yes-associated protein and p53-binding protein-2 interact through their WW and SH3 domains," *J. Biol. Chem.*, 276:14514-14523, 2001.
Goulaouic and Chow, "Directed integration of viral DNA mediated by fusion proteins consisting of human immunodeficiency virus type 1 integrase and *Escherichia coli* LexA protein," *J. Virol.*, 70(1):37-46, 1996.

(Continued)

*Primary Examiner*—Bruce Campell
*Assistant Examiner*—Benjamin P Blumel
(74) *Attorney, Agent, or Firm*—Fulbright & Jaworski, LLP

(57) ABSTRACT

Embodiments of the invention include compositions comprising and methods utilizing a retroviral integrase complex comprising a recombinant integrase having a domain comprising a non-native protein binding site, and a DNA binding protein comprising a DNA binding domain and a peptide binding domain that binds the non-native protein binding site of the recombinant integrase.

13 Claims, 11 Drawing Sheets

OTHER PUBLICATIONS

Hacein-Bey-Abina et al., "A Serious adverse event after successful gene therapy for X-linked severe combined immunodeficiency," *N. Engl. J. Med.*, 348: 255-256., 2003.

Hacein-Bey-Abina et al., "LMO2-associated clonal T cell proliferation in two patients after gene therapy for SCID-X1," *Science*, 302: 415-19, 2003.

Haren et al., "Integrating DNA: transposases and retroviral integrases," *Annu. Rev. Microbio.*, 53:245-281, 1999.

Hughes et al., "Viral-mediated gene transfer to mouse primary neural progenitor cells," *Mol. Ther.*, 5: 16-24., 2002.

Joag et al., *Lentiviruses*. In: Fields BN, Knipe DM, Howley PM (eds.) Fields Virology. Lippincott—Raven Publishers, Philadelphia, pp. 1977-1996, 1996.

Johnston et al., "Minimum requirements for efficient transduction of dividing and nondividing cells by feline immunodeficiency virus vectors," *J. Virol.*, 73: 4991-5000, 1999.

Kang et al., "In vivo gene transfer using a nonprimate lentiviral vector pseudotyped with ross river virus glycoproteins," *J. Virol.*, 76: 9378-9388, 2002.

Khan et al., "Retroviral integrase domains: DNA binding and the recognition of LTR sequences," *Nucl. Acids Res.*, 19: 851-60, 1990.

Kumar et al., "Large-scale production of pseudotyped lentiviral vectors using baculovirus GP64," *Hum. Gene Ther.*, 14: 67-77, 2003.

Kuriyan and Cowburn, "Modular peptide recognition domains in eukaryotic signaling," *Annu. Rev. Biophys. Biomol. Struct.*, 26:259-288, 1997.

Llano et al., "LEDGF/p75 determines celluar tranfficking of diverse lentiviral but not murine oncoretroviral integrase proteins and is a component of functional lentiviral preintegration complexes," *J. Virol.*, 78:9524-37, 2004.

Lotery et al., "Gene transfer to the nonhuman primate retina with recombinant feline immunodeficiency virus vectors," *Hum. Gene Ther.*, 13: 689-696., 2002.

Mitchell et al., "Retroviral DNA integration: ASLV, HIV, and MLV show distinct target site preferences," *PLoS Biol* 2: E234, 2004.

Molteni et al., "Identification of a small-molecule binding site at the dimer interface of the HIV integrase catalytic domain," *Acta Crystallographica Section D-Biological Crystallography*. 57: 536-44, 2001.

Nourry et al., "PDZ domain proteins: plug and play!," *Sci. STKE.* 179:RE7, 2003.

Olivares et al., "Site-specific genomic integration produces therapeutic factor IX levels in mice," *Nature Biotechnology*, 20: 1124-28, 2002.

Ortiz-Urda et al., "Stable nonviral genetic correction of inherited human skin disease," *Nature Med* 8: 1166-70, 2002.

Otte et al., "WW domain sequence activity relationships identified using ligand recognition propensities of 42 WW domains," *Protein Science*, 12:491-500, 2003.

Polard and Chandler, "Bacterial transposases and retroviral integrases," *Mol. Microbiol.*, 1:13-23, 1995.

Quackenbush et al., "The TIGR gene indices: analysis of gene transcript sequences in highly sampled eukaryotic species," *Nucleic Acids Res.*, 29: 159-164., 2001.

Sandmeyer, "Integration by design," *Proc. Natl. Acad. Sci. USA*, 100: 5586-88, 2003.

Schröder et al., "HIV-1 integration in the human genome favors active genes and local hotspots," *Cell*, 110: 521-529., 2002.

Schuler, "Pieces of the puzzle: espressed sequence tags and the catalog of human genes," *J. Mol. Med.*, 75: 694-698., 1997.

Shibagaki and Chow, "Central Core Domain of Retroviral Integrase is responsible for target site selection," *J. Biol. Chem.*, 272:8361-8369.

Shibagaki et al., "Characterization of feline immunodeficicency virus integrase and analysis of functional domains," *Virology*, 230: 1-10, 1997.

Sinn et al., "Persistent gene expression in mouse nasal epithelia following feline immunodeficiency virus-based vector gene transfer," *J Virol.*, 79(20):12818-27, 2005.

Stein et al., "In vivo treatment of hemophilia A and mucopolysaccharidosis type VII using nonprimate lentiviral vectors," *Mol. Ther.*, 3: 850-856., 2001.

Tan et al., "Fusion proteins consisting of human immunodeficiency virus type 1 integrase and the designed polydactyl zinc finger protein E2C direct integration of viral DNA into specific sites," *J. Virol.*, 78: 1301-13, 2004.

Vigdal et al., "Common physical properties of DNA affecting target site selection of *sleeping beauty* and other Tc1/*mariner* transposable elements," *J. Mol. Biol.*, 323: 441-452., 2002.

Wang et al., "Feline immunodeficiency virus vectors persistently transduce nondividing airway epithelia and correct the cystic fibrosis defect," *J. Clin. Invest.*, 104: R55-R62, 1999.

Wu et al., "Transcription start regions in the human genome are favored targets for MLV integration," *Science*, 300: 1749-51, 2003.

Zhu et al., "Controlling integration specificity of a yeast retrotransposon," *Proc. Natl. Acad. Sci. USA*, 100: 5891-95, 2003.

\* cited by examiner

HIV-1 Integrase ...FKRKGGIGGYSAGE... SEQ ID NO.: 28
FIV Integrase ...FKRRGRIGGMAPYE... SEQ ID NO.: 29
FIV Integrase+BstEII ...FKRRGRLPGMAPYE... SEQ ID NO.: 30
FIV Integrase+NpwBP ...FKRKGRIPRLLPPPGPPPGRGMAPYE... SEQ ID NO.: 31
FIV Integrase+p53-BP ...FKRKGRIPEYPPYPPPPYPSGMAPYE... SEQ ID NO.: 32

```
                                      H12N
HIV                       - FLDGIDKAQEDHEKYHSNWRAMASDFNLPPIVAKEI   36
FIV                       SSWVDRIEEAELNHEKFHSDPQYLRTEFNLPRIVAEEI   38
                            ::* *::*: :***:**: : : ::**** ***:**
                                      H14N
HIV     VASCDKCQLKGEAMHGQVDCSPGIWQLDCTHLEGKIVLVAVHVASGYIEAEVIPAETGQE   96
FIV     KRKCPLCRIRGEQVGGQLKIRPGIWQMDCTHFNGKIIIVAVHVESGFLWAQIIPQETADC   98
          .*  *:::** : **:.  *****:****::***::***** **:: *::** **.:

HIV     TAYFILKLAGRWPVKTIHTDNGPNFISTTVKAACWWAGIKQEFGIPYNPQSQGVVESMNK 156
FIV     TVKALLQLICAHNVTELQTDNGPNFKNQKMEGLLNYMGIKHKLGIPGNPQSQALVENANN 158
        *.  :*:*     *. ::******* . .::.    : ***:::*** *****.:**. *:
           Q168A
HIV     ELKKIIGQVRDQAEHLKTAVQMAVFIHNFKRKGGIGGYTAGERIVDIIATDIQTKELQKQ 216
FIV     TLKVWIQKFLPETTSLDNALALALHCLNFKQRGRLGRMAPYELYIQQESLRIQD-YFSAI 218
         **  * :.  ::  *..*: :*:.  ***::* :*  :. *  ::  :  **   :.
           E170A
HIV     ITKIQNFRVYFRDNRDPLWKGPAKLLWKGEGAVVIQDNNE-IKVVPRRKAKIIRDYGKQM 276
FIV     PQKLMMQWLYYKDQKDKKWKGPMRVEYWGQGSVLLKDEEKGIFLVPRRHIRRVPEPCTLP 278
          *:    :*::*::*  **** :: : *:*:*:::*::: * :****: : : :  .

HIV     AGDDCVASGQDED 336
FIV     EGDE--------- 338
         **:
```

FIG. 10

COMPOSITIONS AND METHODS RELATED TO MODIFIED RETROVIRAL VECTORS FOR RESTRICTED, SITE SPECIFIC INTEGRATION

This application claims priority to U.S. Provisional Patent Application Ser. No. 60/638,590, filed on Dec. 22, 2004, which is incorporated in its entirety herein by reference.

The United States Government own rights in this invention pursuant to NIH contract number GM061657, HL075363-01 and HL-51670.

BACKGROUND OF THE INVENTION

I. Field of the Invention

The present invention concerns the fields of molecular medicine and virology. More specifically, the present invention relates to compositions and methods for site specific retroviral integration of therapeutic nucleic acids.

II. Description of Related Art

A prerequisite to persistent gene expression from a lentiviral vector is integration into the chromosome of a transduced cell. This property can be exploited for the long-term correction of genetic diseases; however, the integration reaction carries a potential for mutagenesis. Thus, the nonspecific nature of integration presents a potential drawback for introducing a transgene with lentiviral or other integrating vectors. Insertional mutagenesis may disrupt normal cell actions by inactivating an essential host gene or inappropriately causing overexpression of an undesirable gene. Recently, 3 of 11 children with X-linked SCID treated with ex vivo MuLV retroviral gene transfer of the IL-2 common γ chain into CD34+ cells (Cavazzana-Calvo et al., 2000; Hacein-Bey-Abina et al., 2002) developed a T cell leukemia-like illness, in 2 cases possibly related to a single insertional event in one LMO2 allele (Hacein-Bey-Abina et al., 2003). This incident has raised important issues that must be considered if integrating vectors are to be developed for somatic cell gene therapies.

Bushman and co-workers investigated the chromosomal targets for integration of HIV-1 and an HIV-based vector in a human T cell line (Schroder et al., 2002). The availability of the draft sequence of the human genome has aided the analysis of integration sites. A total of 524 sites of HIV integrations were mapped. It was discovered that transcriptionally active genes were favored as sites of integration. Additionally, hot spots for integration were noted within the genome, including one 2.4 kb region that contained 1% of all integration events (Schroder et al., 2002). Perhaps DNA may be more accessible to the vector pre-integration complex in transcriptionally active areas of the genome; alternatively, the transcription factors bound to trans-acting elements in promoters may interact with the pre-integration complex. In contrast, integration may be less likely in the more tightly constrained noncoding regions or near transcriptionally inactive genes. Furthermore, recent studies have found that the MLV vector has a different integration preference and favors integration in transcriptional start regions (Wu et al., 2003).

Given the described difficulties, additional compositions and methods are needed to develop a more controlled integration of DNA into the genome of a cell for therapy.

SUMMARY OF THE INVENTION

Embodiments of the invention include compositions comprising and methods utilizing a retroviral integrase complex comprising: a) a recombinant integrase having a domain comprising a non-native protein binding site; and b) a DNA binding protein comprising a DNA binding domain and a peptide binding domain, or a tethering protein comprising a peptide binding domain that binds the non-native protein binding site of the recombinant integrase. Typically, the tethering protein is able to interact with other proteins or cellular factors to localize the recombinant integrase to a position of interest within the genome of a cell. In certain embodiments, the integrase can have a carboxy-terminal domain comprising a non-native protein binding site. The integrase can be derived from a phage, retrovirus, or retrotransposon. In certain embodiments, the phage integrase is a tyrosine recombinase or a serine recombinase. In other embodiments, the retroviral integrase is a feline immunodeficiency virus (FIV) integrase, a MLV integrase, lentivirus integrase or other virally encoded integrase, or derivative thereof. In one aspect the integrase is a FIV integrase. Specific modifications of FIV IN can include a H14N and E170A modifications. A retrotransposon derived integrase may be introduced by site directed mutagenesis. The FIV modification can inhibit native interactions between FIV IN and host cell LEDGF/p75. This aspect of the invention creates more favorable conditions for the engineered recombinant FIV IN with a carboxy terminal domain comprising a non-native protein binding site (such as NpwBP) to direct the FIV preintegration complex to the engineered DNA binding protein. A retrotransposon derived integrase includes, but is not limited to a mariner or a sleeping beauty integrase. Aspects of the invention include a peptide binding domain. A non-limiting example of a peptide binding domain is a WW binding domain. A non-native protein binding site may be inserted in a an unstructured loop of the integrase. In a particular aspect, the loop corresponds to amino acids encoded by a viral central-polypurine tract region (cPPT). The non-native protein binding site may comprise, but is not limited to, a PY motif or a PGR motif. In certain aspects, the non-native protein binding site is at least 50, 40, 30, 20, 15, 12, 10 or 8 amino acid in length, and can include any amino acid length therebetween. In certain embodiments of the invention, the DNA binding domain is a zinc finger domain. The DNA binding domain can be a designed zinc finger comprising at least of 2, 3, 4 or 5 or more finger modules (see Porteus and Carroll, 2005, which is incorporated herein by reference). A non-limiting example includes a modified Zif268 or lac repressor DNA binding domain.

In still other embodiments, the invention includes a polynucleotide encoding a recombinant integrase having a domain operatively coupled to the integrase having a non-native protein binding site. Operatively couple includes, but is not limited to, covalent coupling and genetic fusions where the domain is encoded in the nucleic acid encoding the integrase. The polynucleotide is capable of being bound by the amino terminal domain of the encoded integrase. In one aspect, the polynucleotide comprises a transgene. The transgene may be a therapeutic gene, a diagnostic gene, or a therapeutic and diagnostic gene. The polynucleotide may be comprised in a polynucleotide delivery vehicle, such as a virus, a lipid, plasmid, or other polynucleotide delivery vehicle known in the art. A viral polynucleotide delivery vehicle may include, but is not limited to, a lentivirus, an adenovirus, a retrovirus, or an adeno-associated virus.

Yet another embodiment of the invention includes a polynucleotide encoding a recombinant DNA binding protein comprising at least a DNA binding domain and a peptide binding domain, wherein the peptide binding domain binds a protein binding site of a recombinant integrase. Such a polynucleotide may be comprised in a polynucleotide delivery vehicle. The polynucleotide delivery vehicle may be a virus, a liposome, a plasmid protein complex, a plasmid, or other polynucleotide delivery vehicle known in the art. A viral polynucleotide delivery vehicle may include, but is not limited to, an adenovirus, lentivirus, adeno-associated virus, MLV, or the like.

Certain embodiments of the invention include a cell comprising a first polynucleotide encoding a recombinant integrase having a domain comprising a non-native protein binding site and a second polynucleotide encoding a DNA binding protein comprising at least a DNA binding domain and a peptide binding domain that binds a protein binding site of a recombinant integrase. The cell may further comprise a third polynucleotide comprising a transgene. The transgene may be inserted into the genome of the cell. A non-limiting example of a transgene is CFTR, factor VIII, or factor IX. The cell may be comprised in a pharmaceutically acceptable formulation.

Other embodiments of the invention may include a method for controlled integration of a transgene comprising: a) contacting a cell with: i) a first polynucleotide encoding a recombinant integrase having a non-native protein binding site; ii) a second polynucleotide encoding a DNA binding protein that binds the recombinant retroviral integrase encoded by the first polynucleotide; and iii) a third polynucleotide that is bound by the recombinant retroviral integrase encoded by the first polynucleotide and encoding a transgene; and b) isolating a cell wherein the third polynucleotide is incorporated into the genome of the cell. The cell can be, but is not limited to, a stem cell, hematopoietic cell, neoplastic cell, lung cell, heart cell, liver cell, pancreas cell, kidney cell, muscle cell, neuron, or intestinal cell.

Still other embodiments include a method of controlling retroviral integration comprising contacting the genome of a cell with a) an integrase complex comprising i) a recombinant integrase having a carboxy terminal domain comprising a non-native protein binding site; and ii) a recombinant DNA binding protein comprising a DNA binding domain and a peptide binding domain that binds the non-native protein binding site of the recombinant integrase; and b) a polynucleotide that (i) is a substrate for the integrase complex; and (ii) encodes a transgene, wherein integration of the nucleic acid has a lower probability of mutagenizing the cell than random retroviral integration.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 8A) The crystal structure of HIV-1 integrase has recently been reported (Molteni et al., 2001). Of note, the structure contains an unstructured loop (indicated by arrow) that corresponds to the location of the cPPT in the primary sequence. (FIG. 8B) The amino acid sequence of the unstructured loop of HIV-1 has high homology to the cPPT region of FIV integrase. A BstEII restriction enzyme site was introduced into FIV integrase in the packaging plasmid resulting in a 2 amino acid substitution (underlined). Two individual proline rich 13 amino acid motifs (NpwBP (SEQ ID NO:8 and 9) and p53-bp (SEQ ID NO:10 and 11) were inserted in-frame into the BstEII site (SEQ ID NO:6 and 7).

FIG. 10. Alignment of HIV and FIV IN amino acid sequences. Mutations in HIV IN that ablate LEDGF/p75 interaction are shown. Mutations introduced into corresponding FIV residues are also shown (SEQ ID NO:27 and 28).

DESCRIPTION OF ILLUSTRATIVE EMBODIMENTS

Figure 1:
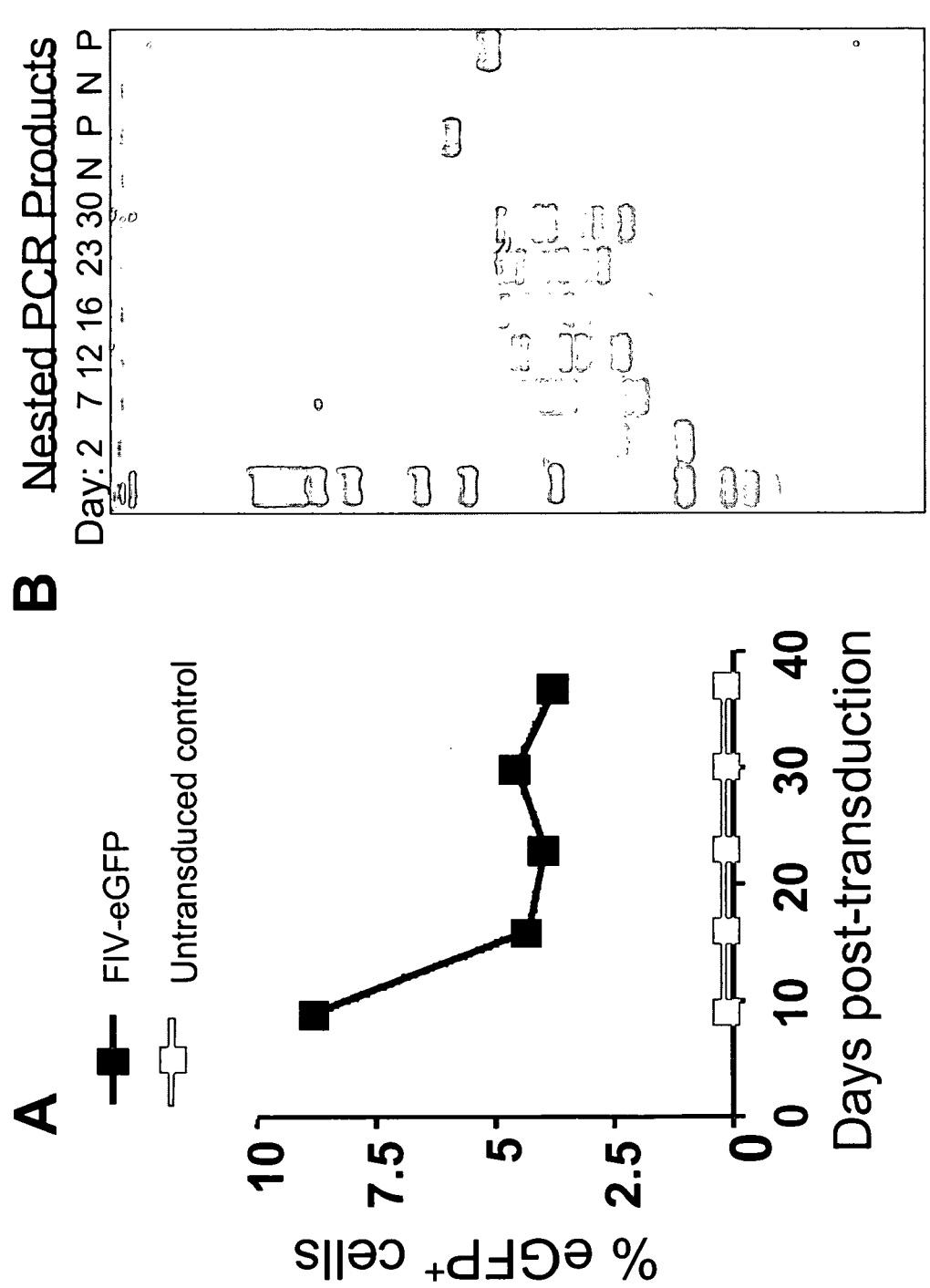
FIGS. 1A and 1B. Persistence of gene transfer and integration site analysis in HepG2 cells. HepG2 cells were transduced with FIV-eGFP and at the time-points indicated, eGFP expression was measured by FACS analysis (FIG. 1A) and the genomic DNA isolated for integration analysis (FIG. 1B). Following an initial decline, eGFP expression remained stable over a month. To analyze the FIV integration events, DNA was digested with either EcoRV or StuI enzymes and adaptor-ligated nested PCR performed as described herein. Panel B shows the nested PCR products from various time-points and demonstrates that integration occurred without emergence of a dominant clone. (P: positive control; N: negative control).

Retroviral vectors may be used to deliver DNA to human and other animal cells. However, their pattern of integration is largely random, and integration is sometimes deleterious in that it causes mutations due to the insertion of several kilobases of heterologous DNA into the genome of the cell. Furthermore, the effectiveness of therapeutic genes delivered by retrovirus vectors can be compromised due to integration into regions of the genome which are not conducive to gene expression.

With the teachings of the present disclosure, taken with what is well known to the art, the integration site specificity of retroviruses and/or retrotransposons can be altered by engineering integrase so that the engineered integrase is operatively coupled to a DNA binding protein component, which alters the integration characteristics of the integrase. The modification described herein results in integration wherever the DNA binding protein or a (tethering) protein locates on the chromosome. The engineering of an integrase is preferably carried out at the nucleic acid level, with the wild-type coding sequence of the integrase being modified by PCR mutagenesis, oligonucleotide site-directed mutagenesis, or endonuclease cutting and ligation to add or substitute a sequence encoding a peptide or portion (protein binding site) into an integrase. In one embodiment, the carboxyl terminus of integrase is engineered to contain the protein binding site. The engineered protein binding site, in conjunction with a complementary peptide or protein binding domain of the DNA binding protein or tethering protein, determines the desired interactions and characteristics by altering and/or producing a heterologous integrase complex. In one embodiment, the DNA binding protein is a recombinant protein that recognizes specific DNA sequences. The integrase complex may be directed to a desired portion or directed away from an undesired portion of genomic DNA, thus producing a desired integration site characteristic.

The current invention exemplifies compositions and related methods for the integration and expression of therapeutic nucleic acids with an associated reduction in the occurrence of detrimental integration events. The methods involve the use of one or more nucleic acid expression vectors encoding or harboring a recombinant retroviral integrase, a recombinant DNA binding protein or a tethering protein, a therapeutic polynucleotide, or a combination thereof. A recombinant integrase may be encoded by a polynucleotide delivered by a first nucleic acid expression vector. After infection, a recombinant DNA binding protein or a tethering protein, which may be encoded by a second nucleic acid expression vector and delivered by the first or a second delivery vehicle, interacts with the recombinant integrase of the invention and the vector coded reverse transcribed DNA to form a preintegration complex. The preintegration complex including the recombinant integrase binding to the desigend DNA binding protein then guides the integration of a target polynucleotide into a target genome. Moreover, an embodiment of the present invention involves the use of an integrase complex to integrate DNA sequences, with a lower probability of detrimental integration than random integration or the native integration specificity of an unmodified integrase, into the genome of cells. In certain aspects the modified cells are suitable for implantation in vivo. In other aspects, a polynucleotide that is integrated into the genome of a target cell will encode a therapeutic polynucleotide. A "therapeutic polynucleotide" or "therapeutic gene" refers to a nucleotide sequence that is capable, when transferred to an individual directly or via a delivery vector including a cell, of eliciting a prophylactic, curative or other beneficial effect in the individual. A therapeutic polynucleotide product may be produced as a result of transcription and/or translation of the therapeutic polynucleotide. Therapeutic polynucleotide products include transcription products (e.g., antisense mRNA, siRNA, and catalytic RNA), and translation products (e.g., proteins or peptides) of the therapeutic polynucleotide.

Expression constructs or vectors of the invention include nucleic acids that encode elements for integration of a polynucleotide as well as any therapeutic polynucleotide of the invention. Delivery vectors of the invention include the compositions necessary to introduce or deliver the expression constructs to a particular location. For example, delivery vectors may include cellular, viral, and non-viral means for the delivery of an expression vector to an individual or a cell. In particular aspects of the invention a first lentiviral expression vector may be delivered using a lentiviral delivery vector and a second expression vector may be delivered using an adenoviral or non-viral delivery vector.

With the teachings of the present disclosure, the specificity determining domain of an integrase complex can be modified resulting in the adoption of a modified insertion specificity directed by a DNA binding protein with which it interacts or is tethered. The interaction between the components is directed by a protein binding domain/peptide (protein binding site) pair. The protein binding domain will typically be included in or associated with the DNA binding component or a tethering protein that couples the integrase with a DNA binding function, whereas the peptide or protein binding site is engineered into an integrase of interest producing a non-native or heterologous protein binding site in the integrase. The protein binding site interacts with a protein binding domain of DNA binding protein or tethering proteins when both components are present in an appropriate context, such as both components being expressed in vitro or in vivo in the same cell.

Expression vectors suitable for use in certain aspects of the invention typically include sequences necessary for integrase-mediated processing and integration. In particular, inverted repeat regions of viral LTRs may be elements of the recombinant nucleic acid expression vectors (e.g., retroviral expression vectors) of the invention. For purposes of the present invention, the term "recombinant" refers to engineered biopolymers (e.g., polynucleotides or polypeptides), cells, or organisms of which any portion of the sequences or sequence organizations contained therein are not naturally occurring. The term non-native or heterologous may be used to describe a particular polynucleotide or polypeptide sequence that occurs in a position that is not typical in a non-recombinant or native cell or polymer.

Figure 7:
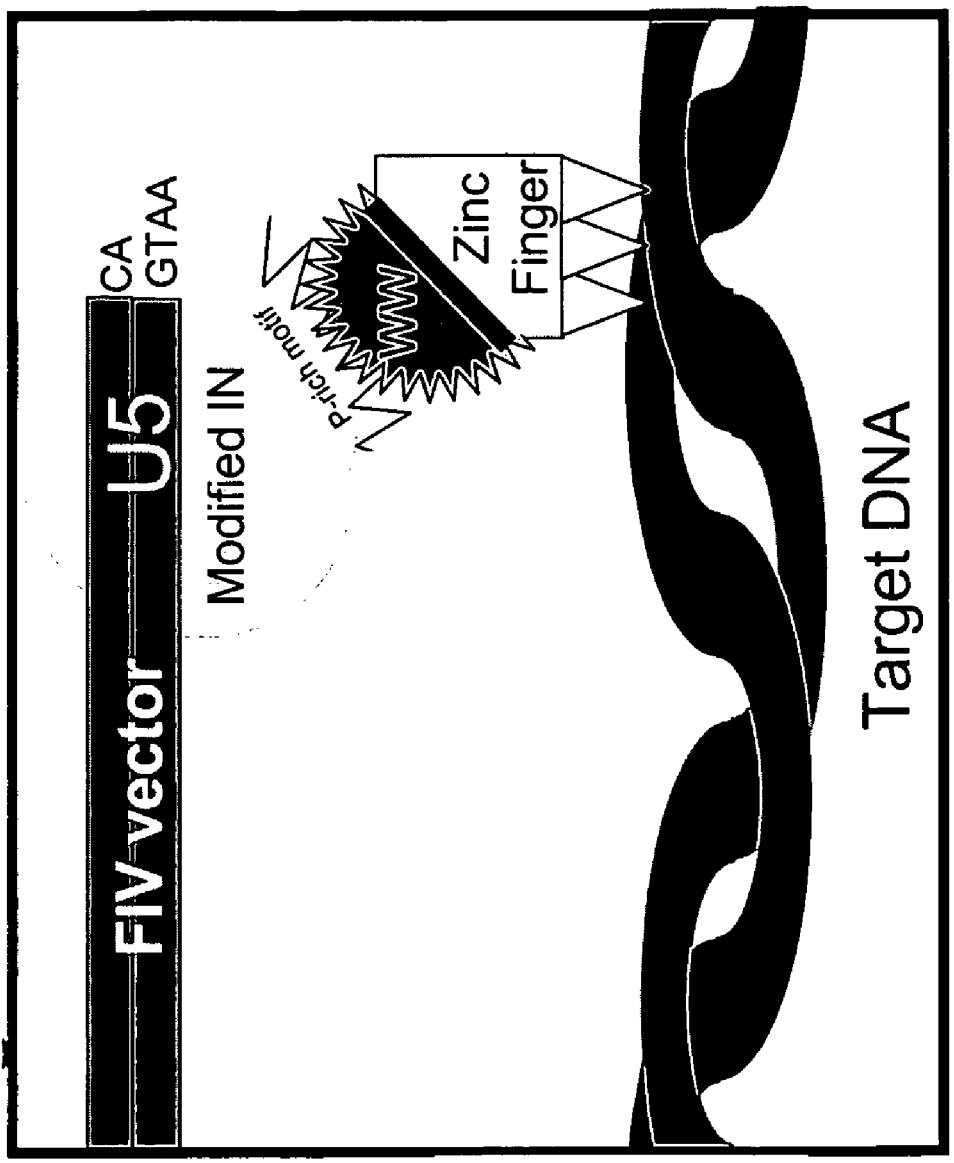
FIG. 7. Schematic representation of the proposed technique to direct integration of a FIV-based vector. FIV integrase is modified to contain a proline rich motif (SEQ ID NO:8 and 9) that binds its partnered WW domain (amino acids 31 to 66 of SEQ ID NO:23) contained on an engineered tethering protein (DNA binding protein, for example Zif268 (SEQ ID NO:20 and 21). The co-expressed DNA binding protein contains a designed zinc finger DNA binding domain that directs the integration complex to those genomic loci that contains its recognition sequence.

In the case of a retroviral expression vector, persistent expression of a therapeutic polynucleotide typically relies on the expression vector being reverse transcribed from RNA and integration of the newly transcribed cDNA into a host cell chromosome. This process makes lentiviral vectors an attractive tool to achieve life-long gene delivery. Then again, the nonspecific nature of retroviral integration presents inherent hazards and variations in gene expression as described herein. This issue was recently evinced by insertional mutagenesis in the French X-linked SCID trial (Hacein-Bey-Abina et al., 2003). The present disclosure exemplifies and describes a novel strategy to modify an integrase (IN), exemplified by an IN derived from a feline immunodeficiency virus (FIV)-based lentiviral vector, to achieve restricted and directed integration. In certain aspects, a minimal proline-rich peptide sequence may be inserted into a loop of FIV integrase. Proline-rich motifs may tether or operatively couple the FIV integration complex by high affinity binding to an engineered fusion protein consisting of a protein binding domain (e.g., WW protein binding domain) and a DNA binding domain (e.g., zinc finger domain) (FIG. 7). Typically, the DNA binding domain will direct integration to portions of the genome that contain the appropriate recognition sequence. The tethering or coupling of a modified IN protein to a DNA binding domain will direct the lentiviral vector integration complex to or away from sites on chromosomal DNA.

Modified expression vectors (e.g., FIV-based expression vectors) encoding a recombinant integrase of the invention maintain the ability to express an integrase activity. Preliminary studies show that an inserted proline-rich peptide motif does not disrupt the production of a functional polynucleotide. Typically, the expression vector may be assessed for integration activity, integration complex formation, genomic or integration profile, and ability to be packaged in a delivery vector to name a few exemplary characteristics. The catalytic and integrase activity of modified IN is typically assessed in vitro by a double-stranded oligo based 3'-end processing and 3'-end joining assay. Furthermore, various protein interaction assays, such as yeast two hybrid assays, may be used to assess high affinity protein-protein interactions between the modified INs and DNA binding proteins or tethering proteins. These studies will guide selection of an optimal protein binding domain and a peptide binding site. PCR based integration assays may also be used to demonstrate restricted integration into plasmids containing recognition sequences for the DNA binding proteins. Furthermore, sites of integration into the genome of cultured human cells may be mapped following gene transfer of an expression vector (e.g., retroviral nucleic acid encoding a therapeutic polynucleotide) to determine if integration patterns are altered.

In certain embodiments, the transient expression of the DNA binding protein or tethering protein is needed to direct integration. For in vivo studies, the DNA binding protein may be introduced in a variety of ways, for example co-administration or pre-treatment with a DNA binding protein expressing Ad, AAV or other delivery vector. Current technology exists for the production of designer zinc finger DNA binding proteins to target specific chromosomal loci (Kang and Kim, 2000; Jamison et al., 2003), which may provide a facile system for controlling vector integration specificity. In certain aspects, a bioinformatics approach may be used to choose unobtrusive yet accessible genomic loci.

I. Integrase Complex

Various aspects of the invention describe an integrase complex comprising a recombinant integrase operatively coupled to a recombinant DNA binding protein. In other aspects, an intermediary tethering protein can be used which binds both the integrase and the DNA binding protein to form a complex at a chromosomal location. Typically, this complex will direct the integration away from genomic sites that may prove detrimental to the cell or the organism harboring the cell.

A. Integrase

Integration of heterologous nucleic acid fragments into a chromosome may be mediated by a site-specific recombinase (integrase) that can catalyze the insertion or excision of nucleic acid fragments. These enzymes recognize relatively short unique nucleic acid sequences that serve for both recognition and recombination. Examples include Cre (Sternberg and Hamilton, 1981 Flp (Broach et al., 1982) and R (Matsuzaki et al., 1990). See Haren et al., (1999) for additional review.

In one aspect, a recombinant integrase (IN) is engineered to contain a peptide sequence to which a protein binding domain associates, i.e., a protein binding site, and provides for the association or tethering to a DNA binding protein of the invention. The IN plays a central role in the retrovirus lifecycle, hence extensive studies of its function and structure have been conducted (Shibagaki et al., 1997; Joag et al., 1996). Retroviral IN mediates a strand transfer of long terminal repeat (LTR) DNA 3' OH ends into the host DNA. IN has three physically distinct domains. (1) An N-terminal domain that includes three-helices and a zinc-binding motif. This domain has been implicated in dimerization and in binding the LTR ends. (2) The central domain that contains the conserved catalytic triad DDE. (3) The C-terminal domain that contributes to oligomerization and has nonspecific DNA-binding activity. In the case of lentivirus, there is a central polypurine tract (cPPT) in IN nucleic acids that provide a site of initiation for plus strand DNA synthesis from the negative strand RNA template. The cPPT is required for the replication of the wild-type virus. However, in the context of certain embodiments of the invention, such as a three plasmid production system of a FIV-based vector, a cPPT is not required within IN (Johnston et al., 1999). Recently, the crystal structure of HIV IN was reported (FIG. 8A) (Molteni et al., 2001). The cPPT region of IN encodes a loop in the IN protein (FIGS. 8A and 8B) and is not located within any of the three necessary domains. The cPPT region of FIV-IN or a homologous region in other viruses is an ideal location, but not the only location, to insert a protein binding site for the redirection of nucleic acid integration.

Studies using a naked DNA vector containing φC31 bacteriophage attB sites co-administered with a DNA vector expressing φC31 bacteriophage integrase, site restricted integration have been reported (Olivares et al., 2002; Ortiz-Urda et al., 2002). In this system, integration preferentially occurs at pseudo-attP sites in the genome. However, the efficiency of integration is prohibitively low for many in vivo applications (<0.1%).

Unlike naked DNA, the use of retroviral vectors to integrate vector encoded genes into target cells is highly efficient. Proofs of principle are established that describe techniques to overcome the problem of the non-specific nature of retroviral integrase (Bushman, 2002; Bushman and Miller, 1997). Recently, a construction of fusion proteins consisting of HIV-1 IN and E2C zinc finger DNA binding protein was reported (Tan et al., 2004). Importantly, it was demonstrated that the fusion protein had integrase activity, bound the E2C recognition sequence, and had a restricted integration pattern near E2C sites by an in vitro assay. These data suggest that if a lentiviral integrase complex contains a zinc finger DNA binding domain, site-specific integration can be achieved. However, it has not been demonstrated that such a fusion protein can be packaged into a functional lentiviral delivery vector. The ability to package a fusion protein as described is one consideration for targeted integration to be used in the practical application for gene therapy.

B. Nucleic Acid Binding Proteins

DNA binding proteins or tethering proteins of the invention are engineered to provide for the coupling of the DNA binding function to an integrase. Typically, the coupling capabilities are engineered by inclusion of a protein or peptide binding domain (protein-protein interaction domain), exemplified by a WW domain. Thus, a DNA binding domain is tethered or operatively coupled directly or indirectly to the integrase of interest. Direct coupling may entail the production of a fusion protein where the protein or peptide binding domain is part of the DNA binding polypeptide. Indirect coupling may be accomplished, for example, by a known crosslinker, wherein the protein binding domain is reversibly or irreversable crosslinked to a DNA binding domain. A cross linker may also be in the form of an intermediate protein capable of binding both an integrease and a DNA binding protein. The DNA binding protein can also be a native DNA binding protein that is produced by the target cell or ectopically expressed in the target cell. The tethering protein does not have to interact with DNA directly, but it can interact with other DNA binding proteins or proteins associated with DNA binding proteins.

Examples of protein domains having DNA binding activity include zinc fingers, leucine zippers, helix-turn-helix domains, and homeodomains. DNA binding proteins of the invention will typically bind a set of target sites. A "target site" is the nucleic acid sequence recognized by a DNA binding protein such as a zinc finger protein. The length of a target site varies with the characteristics of the DNA binding domain(s), and with the number of sequence specific bonds formed between the protein and the target site. Typically, a two-fingered zinc protein recognizes a four to seven base pair target site, a three-fingered zinc finger protein recognizes a six to ten base pair target site, and a six fingered zinc finger protein recognizes two adjacent nine to ten base pair target sites. A "subsite" or a "target subsite" is a subsequence of the target site, and corresponds to a portion of the target site recognized by a subunit of the DNA binding protein. Particular aspects of the invention DNA binding proteins that are $Cys_2$-$His_2$ zinc finger binding proteins which, as is well known in the art, bind to target nucleic acid sequences via α-helical zinc metal atom coordinated binding motifs known as zinc fingers. Each zinc finger in a zinc finger nucleic acid binding protein is responsible for determining binding to a nucleic acid triplet, or an overlapping quadruplet, in a nucleic acid binding sequence. Various zinc finger polypeptides are described in U.S. Patent Application 2004110923 or 20030119023, or WO 96/06166, WO 98/53058, WO 98/53057, or WO 98/53060, as well as the conserved domain database maintained by National Center for Biotechnology Information (NCBI), which are incorporated herein by reference in their entirety.

From a structural perspective, DNA-binding proteins containing domains suitable for use as polypeptide components of a composite DNA-binding region may be classified as DNA-binding proteins with a helix-turn-helix structural design, including, but not limited to, MAT 1, MAT 2, MAT a1, Antennapedia, Ultrabithorax, Engrailed, Paired, Fushi tarazu, HOX, Unc86, and the previously noted Oct1, Oct2 and Pit; zinc finger proteins, such as Zif268 (SEQ ID NO:21), SWI5, Kruppel and Hunchback; steroid receptors; DNA-binding proteins with the helix-loop-helix structural design, such as Daughterless, Achaete-scute (T3), MyoD, E12 and E47; and other helical motifs like the leucine-zipper, which includes GCN4, C/EBP, c-Fos/c-Jun and JunB. The amino acid sequences of the component DNA-binding domains may be naturally-occurring or non-naturally-occurring (or modified).

The choice of DNA-binding domains may be influenced by a number of considerations, including the species, system and ultimately the cell type in which the optimized DNA binding domain (DBD) is to be expressed; the feasibility of incorporation into a chimeric protein, as may be shown by modeling; and the desired application or utility. The choice of DNA-binding domains may also be influenced by the individual DNA sequence specificity of the domain and the ability of the domain to interact with other proteins or to be influenced by a particular cellular regulatory pathway. The DNA-binding domains can be isolated from a naturally-occurring protein, or may be a synthetic molecule based in whole or in part on a naturally-occurring domain.

A protein-protein interaction domain typically comprises an amino acid sequence which, under standard conditions utilized for cell culture, interacts with, that is, binds to, a peptide or polypeptide "partner." Such an interaction can be a homotypic or a heterotypic interaction. A homotypic interaction refers to an interaction in which the polypeptide partner is the same as the interacting portion of the protein-protein interaction domain. A heterotypic interaction refers to an interaction in which the polypeptide partner differs from the interacting portion of the protein-protein interaction domain.

The protein-protein interaction domains of the invention preferably form dimers, but may form trimers, tetramers, pentamers, hexamers or other oligomers or multimers with one or more polypeptide partners. As discussed above, such interactions can be homotypic or heterotypic. Therefore, the protein-protein interaction domains can form homodimers, homotrimers, etc., as well as heterodimers, heterotrimers, and the like. Typically, the protein-protein interaction domain forms a dimer between a recombinant IN protein and a recombinant DNA binding or tethering protein of the invention. U.S. Pat. No. 6,720,181 describes various methods for identifying and characterizing protein-protein interaction domains and is incorporated herein by reference in its entirety.

Examples of protein binding domains include, but are not limited to sequence specific binding domains such as WW domains, PTB domains, SH3 domains, and FHA domains. Recognition of a ligand by some of these domains, for example, SH3, is regulated by a kinase in the sense that the domain will recognize the ligand when the ligand is not phosphorylated, and will not bind the ligand only when it is phosphorylated.

C. Expression Vectors

The process of proviral establishment via the proper integration of retroviral DNA into the host genome has been well documented (Varmus, 1988). In addition, the functional domains of retroviral integrase (IN) have been identified (Khan et al., 1990). The retroviral integrase protein consists of an amino terminal DNA binding domain characterized by a "zinc-finger" like motif thought to be involved in binding of viral LTRs prior to and during genomic integration. A centrally located catalytic domain contains three acidic residues that are highly conserved among the retroviral and retrotransposon families. This region of IN has been shown to possess both exonuclease and joining activities.

Several groups have demonstrated that the lack of specificity in DNA binding by retroviral integrase may be biased to occur at engineered sites for DNA binding proteins in vitro (Bushman, 1994; Goulaouic and Chow, 1996; Bushman, 1995, see also WO 97/2003, which are herein incorporated by reference). The site-directed integration observed in these in vitro studies was catalyzed by fusion proteins that combined a retroviral IN protein with a prokaryotic DNA binding protein. The results of the in vitro biochemical assays indicated that the chimeric IN proteins could direct integration into naked (e.g., non-chromatinized) target DNA sequences comprising engineered target sequences. The bacterial or phage DNA binding protein component of chimeric integrase proved capable of biasing in vitro integration reactions to regions within the 30-50 nucleotides flanking the engineered DNA target sequence.

Typically, the expression vectors (DNA or RNA versions) are to be packaged into infectious viral (e.g., retroviral) particles (i.e., viral delivery vectors). Where these viral delivery vectors are retroviral delivery vectors incorporating expression vectors for an integrase or DNA binding protein of the invention, the vector will typically encode a Psi packaging sequence. For the purposes of the present disclosure, the term "infectious virus" shall mean that an assembled virus, or the genetic complement packaged within an assembled virus, is capable of infecting a target cell where the virally encoded material is directly (in the case of a DNA virus), or indirectly (as in the case of a retrovirus) expressed by the infected cell. Although infectious virus may be replication competent, for the purposes of the present invention a virus need not be replication competent to be considered "infectious."

Retrovirus package an RNA genome that serves as a template for the production of a DNA genome (via reverse transcription) that goes on to form the integrated proviral genome during retroviral infection. Accordingly, for the purposes of the present invention, it is to be understood that a retroviral RNA genome comprises a relevant polynucleotide sequence element (e.g., promoter, intron, gene, splicing signals, polyadenylation site, etc.) when the corresponding proviral DNA sequence has the relevant sequence elements. Similarly, a retroviral genome comprises the relevant order, position, or organization of sequence elements when the corresponding integrated provirus manifests the relevant order, position, or organization of sequence elements.

One of the vectors specifically contemplated by the present invention is a vector designed to allow for selection and identification of cells into which the vector has integrated. This vector contains a constitutively active promoter located 5' to a selectable or screenable marker which has a polyadenylation site located at its 3' terminus of the polynucleotide encoding the marker. Other aspects of the invention include a vector containing a therapeutic nucleic acid to be expressed in a cell of interest.

D. Delivery Vectors

Although the delivery vectors specifically described in the present invention are derived from the FIV virus, the present invention is not limited to this particular virus. For example, the presently described technology may be adapted to a wide variety of both DNA and RNA delivery vector systems including, but not limited to, adenovirus; Moloney murine leukemia virus; mouse mammary tumor virus; adeno-associated virus; lentivirus, e.g., simian/human immunodeficiency virus, human T-cell leukemia virus, simian virus (SV40), feline leukemia virus, Friend leukemia virus, bovine leukemia virus, herpesvirus (including Epstein-Barr virus); polyomavirus; papillomavirus; liposomes; naked DNA; and other viral and non-viral delivery vectors. The present technology can also be adapted to both transposable and retrotransposable elements of prokaryotic or eukaryotic origin, examples of which include the bacterial transposons such as Tn5, the yeast Ty retrotransposons and *Drosophila* P-elements. The presently described invention is in no way limited to the above listed transposable elements.

Similarly, preferred target cells for the present invention include, but are not limited to, cells derived from both human and non human origins including vertebrates and mammals, bovine, ovine, porcine, canine, feline, avian, bony and cartilaginous fish, rodents including mice (*Mus musculus*) and rats, primates including man (*Homo sapiens*), and monkeys, ferrets, sheep, rabbits and guinea pigs. The target cells can also be plant cells.

Viral vectors have long been used to deliver genes to animals, including humans, and animal cells. More recently, retroviruses have been identified in plants suggesting that they can be used to deliver DNA to plant cells. (Wright and Voytas, 1998). Potential retroviruses in plants: Tat1 belongs to a lineage of *Arabidopsis thaliana* retrotransposons that encode envelope-like proteins).

In particular, engineered retrovirus have been used in a wide variety of in vitro and in vivo gene delivery applications. Given the widespread use of retroviral vectors, it is clear that the presently described methods of directing viral integration will materially enhance retrovirally mediated gene delivery and minimize gene disruption.

Yet another embodiment of the present invention includes methods and tools for effecting both ex vivo and in vivo gene therapy. For example, U.S. Pat. No. 5,399,346 teaches methods of practicing ex vivo gene therapy in humans and is incorporated by reference. For the purposes of this application, the terms "treatment," "therapeutic use," or "medicinal use" used herein shall refer to any and all uses which remedy a disease state or symptoms, or otherwise prevent, hinder, retard, or reverse the progression of disease or other undesirable symptoms in any way whatsoever.

Gene therapy applications usually involve the delivery of one or more genes to a target cells which subsequently express the delivered genes. Expression can be transient, stable, or regulated (using appropriate promoter elements). When expressed, the product encoded by the delivered gene will directly or indirectly provide the desired benefit to a cell or an individual being treated.

Although gene delivery often involves enhancing the amount of the delivered polynucleotide/protein in the target cell, the presently described methods and tools can be used to reduce the amount of endogenous gene expression in a cell or animal by inactivating or "knocking out" the targeted gene or its promoter by use of interfering RNAs or the like (e.g., ribozymes, siRNA, etc.).

Animal cells and tissue are amenable to genetic manipulation and introduction heterologous DNA according to well known methods, including but not limited to electroporation, particle bombardment, liposomes, receptor-mediated endocytosis, polyethylene glycol mediated transformation and other methods for transfection and transformation. Selection techniques and markers, where desired, are also well known to the skilled artisan.

Except as noted, standard techniques for cloning, DNA isolation, amplification and purification, for enzymatic reactions involving DNA ligase, DNA polymerase, restriction endonucleases and the like, and various separation techniques are those known and commonly employed by those skilled in the art A number of standard techniques are described in Sambrook et al. (2001); DNA Cloning Vol. I and II, IRL Press, Oxford, UK; Hames and Higgins (eds.) (1985); Nucleic Acid Hybridization, IRL Press, Oxford, UK; and Setlow and Hollaender (1979); and Genetic Engineering: Principles and Methods, Vols. 1-4, Plenum Press, New York. Abbreviations and nomenclature, where employed, are deemed standard in the field and commonly used in professional journals such as those cited herein. All references cited are incorporated by reference in their entirety.

Gene transfer development for treatment or prevention of cystic fibrosis lung disease has been limited by the inability of vectors to efficiently and persistently transduce airway epithelia. Influenza A is an enveloped virus with natural lung tropism; however, pseudotyping feline immunodeficiency virus (FIV)-based lentiviral vector with the hemagglutinin envelope protein proved unsuccessful. Conversely, pseudotyping FIV with the envelope protein from influenza D (Thogoto virus GP75) resulted in titers of $10^6$ transducing units (TU)/ml and conferred apical entry into well-differentiated human airway epithelial cells. Baculovirus GP64 envelope glycoproteins share sequence identity with influenza D GP75 envelope glycoproteins. Pseudotyping FIV with GP64 from three species of baculovirus resulted in titers of $10^7$ to $10^9$ TU/ml. Of note, GP64 from *Autographa californica* multicapsid nucleopolyhedrovirus resulted in high-titer FIV preparations (approximately $10^9$ TU/ml) and conferred apical entry into polarized primary cultures of human airway epithelia. Using a luciferase reporter gene and bioluminescence imaging, persistent gene expression was observed from in vivo gene transfer in the mouse nose with *A. californica* GP64-pseudotyped FIV (AcGP64-FIV).

Longitudinal bioluminescence analysis documented persistent expression in nasal epithelia for approximately 1 year without significant decline. According to histological analysis using a LacZ reporter gene, olfactory and respiratory epithelial cells were transduced. In addition, methylcellulose-formulated AcGP64-FIV transduced mouse nasal epithelia with much greater efficiency than similarly formulated vesicular stomatitis virus glycoprotein-pseudotyped FIV. These data suggest that AcGP64-FIV efficiently transduces and persistently expresses a transgene in nasal epithelia in the absence of agents that disrupt the cellular tight junction integrity.

II. Proteins and Peptides

In certain embodiments, the present invention concerns novel compositions comprising at least one protein or peptide, which may be encoded by expression cassettes, or expression vectors of the invention. As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide are used interchangeably herein.

In certain embodiments the size of at least one protein or peptide may comprise, but is not limited to, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties. Accordingly, the term protein or peptide encompasses amino acid sequences comprising at least one of the 20 common amino acids found in naturally occurring proteins, or at least one modified or unusual amino acid, including, but not limited to, 2-Aminoadipic acid (Aad), N-Ethylasparagine (EtAsn), 3-Aminoadipic acid (Baad), Hydroxylysine (Hyl), β alanine, β Amino propionic acid (Bala), allo Hydroxylysine (AHyl), 2-Aminobutyric acid (Abu), 3-Hydroxyproline (3Hyp), 4-Aminobutyric acid (4Abu), 4-Hydroxyproline (4Hyp), 6-Aminocaproic acid (Acp), Isodesmosine (Ide), 2-Aminoheptanoic acid (Ahe), allo Isoleucine (AIle), 2-Aminoisobutyric acid (Aib), N-Methylglycine (MeGly), 3-Aminoisobutyric acid (Baib), N-Methylisoleucine (MeIle), 2-Aminopimelic acid (Apm), 6-N-Methyllysine (MeLys), 2,4-Diaminobutyric acid (Dbu), N-Methylvaline (MeVal), Desmosine (Des), Norvaline (Nva), 2,2'-Diaminopimelic acid (Dpm), Norleucine (Nle), 2,3-Diaminopropionic acid (Dpr), Ornithine (Orn), or N-Ethylglycine (EtGly).

Proteins or peptides may be made by any technique known to those of skill in the art, including the expression of proteins, polypeptides or peptides through standard molecular biological techniques. Coding regions for known genes may be amplified and/or expressed using the techniques disclosed herein or as would be know to those of ordinary skill in the art. Alternatively, various commercial preparations of proteins, polypeptides and peptides are known to those of skill in the art. All or part of the amino acids or amino acids encoded by Genbank Accession numbers NM_00520, NM_005426, NM_138473, NM_001964, and NM_144495 are incorporated herein by reference.

A. Fusion Proteins

Another embodiment of the present invention concern fusion proteins. These molecules generally have all or a substantial portion of a peptide or polypeptide, linked at the N- or C-terminus, to all or a portion of a second polypeptide or protein. Other embodiments of the invention include the insertion of a domain within a polypeptide, thus fusion protein also includes other non-amino or carboxy terminal insertions of amino acid sequence. For example, fusions may employ leader sequences from other species to permit the recombinant expression of a protein in a heterologous host. Another useful fusion includes the addition of a functional domain, such as a DNA binding domain, protein interaction domain, or an antibody epitope (to facilitate purification of the fusion protein). In certain aspects, a cleavage site may be included at or near a fusion junction will facilitate removal of the extraneous polypeptide after purification. Other useful fusions include linking of functional domains, such as active sites from enzymes, glycosylation domains, cellular targeting signals or transmembrane regions. In other embodiments, the fusion proteins of the instant invention comprise a DNA binding protein fused to a protein interaction domain. These examples are not meant to be limiting.

Methods of generating fusion proteins are well known to those of skill in the art. Such proteins can be produced, for example, by chemical attachment using bifunctional cross-linking reagents or proteins, by de novo synthesis of the complete fusion protein, or by attachment of a DNA sequence encoding a first domain or peptide to a DNA sequence encoding a second peptide or protein, followed by expression of the intact fusion protein.

B. Protein Purification

In certain embodiments, a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or peptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the protein or peptide in the composition.

Various methods for quantifying the degree of purification of the protein or peptide are known to those of skill in the art in light of the present disclosure. These include, for example, determining the specific activity of an active fraction, or assessing the amount of protein or peptide within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing some other chromatography systems. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, and temperature). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Smaller peptides of the invention can be synthesized in solution or on a solid support in accordance with conventional techniques. Various automatic synthesizers are commercially available and can be used in accordance with known protocols (see, for example, Stewart and Young, 1984; Tam et al., 1983; Merrifield, 1986; or Barany and Merrifield, 1979, each incorporated herein by reference). Short peptide sequences, usually from about 6 up to about 35 to 50 amino acids, can be readily synthesized by such methods. Alternatively, recombinant DNA technology may be employed wherein a nucleotide sequence which encodes a peptide of the invention is inserted into an expression vector, transformed or transfected into an appropriate host cell, and cultivated under conditions suitable for expression.

C. Cross-Linkers

Bifunctional cross-linking reagents have been extensively used for a variety of purposes including production of fusion protein complexes, preparation of affinity matrices, modification and stabilization of diverse structures, identification of ligand and receptor binding sites, and structural studies. Cross-linkers can also include bifunctional protein binding domains. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities or affinities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking peptides or polypeptides to liposomes are described in U.S. Pat. Nos. 5,603,872 and 5,401,511, each specifically incorporated herein by reference in its entirety. Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites are dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups.

III. Nucleic Acids

Nucleic acids according to the present invention may encode a targeting peptide, a receptor protein, a fusion protein, or other protein or peptide. The nucleic acid may be derived from genomic DNA, complementary DNA (cDNA), synthetic DNA or the like. Where incorporation into an expression vector is desired, the nucleic acid may also comprise a natural intron or an intron derived from another gene. Such engineered molecules are sometime referred to as "mini-genes."

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide.

It is contemplated that targeting peptides, fusion proteins and receptors may be encoded by any nucleic acid sequence that encodes the appropriate amino acid sequence. The design and production of nucleic acids encoding a desired amino acid sequence is well known to those of skill in the art, using standardized codon tables. In preferred embodiments, the codons selected for encoding each amino acid may be modified to optimize expression of the nucleic acid in the host cell of interest. Codon preferences for various species of host cell are well known in the art.

In addition to nucleic acids encoding the desired peptide or protein, the present invention encompasses complementary nucleic acids that hybridize under high stringency conditions with such coding nucleic acid sequences. High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture.

A. Vectors for Cloning, Gene Transfer and Expression

In certain embodiments, expression vectors are employed to express the recombinant IN, recombinant DNA binding protein, fusion proteins, and/or therapeutic nucleic acids. In other embodiments, the expression vectors are used in gene therapy. Expression requires that appropriate signals be provided in the vectors, which include various regulatory elements, such as enhancers/promoters from both viral and mammalian sources that drive expression of the genes of interest in host cells. Elements designed to optimize messenger RNA stability and translatability in host cells also are known.

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Ridgeway, 1988; Nicolas and Rubinstein, 1988; Baichwal and Sugden, 1986; Temin, 1986). Preferred gene therapy vectors are generally viral vectors.

In using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

DNA viruses used as gene vectors include the papovaviruses (e.g., simian virus 40, bovine papilloma virus, and polyoma) (Ridgeway, 1988; Baichwal and Sugden, 1986) and adenoviruses (Ridgeway, 1988; Baichwal and Sugden, 1986).

One of the preferred methods for in vivo delivery involves the use of an adenovirus expression vector. Although adenovirus vectors are known to have a low capacity for integration into genomic DNA, this feature is counterbalanced by the high efficiency of gene transfer afforded by these vectors.

Generation and propagation of adenovirus vectors that are replication deficient depend on a unique helper cell line, designated 293, which is transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3, or both regions (Graham and Prevec, 1991).

Helper cell lines may be derived from human cells such as human embryonic kidney cells, muscle cells, hematopoietic cells or human embryonic mesenchymal or epithelial cells. Alternatively, the helper cells may be derived from the cells of other mammalian species that are permissive for human adenovirus. Such cells include, for example, Vero cells or other monkey embryonic mesenchymal or epithelial cells. As discussed, the preferred helper cell line is 293. Racher et al. (1995) disclose improved methods for culturing 293 cells and propagating adenovirus.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include tracheal instillation (Rosenfeld et al., 1991; Rosenfeld et al., 1992), muscle injection (Ragot et al., 1993), peripheral intravenous injections (Herz and Gerard, 1993) and stereotactic innoculation into the brain (Le Gal La Salle et al., 1993).

Other gene transfer vectors may be constructed from retroviruses (Coffin, 1990). The retroviral genome contains three genes, gag, pol, and env. that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences, and also are required for integration in the host cell genome (Coffin, 1990).

In order to construct a retroviral vector, a nucleic acid encoding a protein of interest is inserted into the viral genome in the place of certain viral sequences to produce a virus that is replication-defective. In order to produce virions, a packaging cell line containing the gag, pol, and env genes, but without the LTR and packaging components, is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., 1975).

Other viral vectors may be employed as expression constructs. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984), and herpes viruses may be employed. They offer several attractive features for various mammalian cells (Friedmann, 1989; Ridgeway, 1988; Baichwal and Sugden, 1986; Coupar et al., 1988; Horwich et al., 1990).

Several non-viral methods for the transfer of expression constructs into cultured mammalian cells also are contemplated by the present invention. These include calcium phosphate precipitation (Graham and van der Eb, 1973; Chen and Okayama, 1987; Rippe et al., 1990; DEAE dextran (Gopal, et al., 1985), electroporation (Tur-Kaspa et al., 1986; Potter et al., 1984), direct microinjection, DNA-loaded liposomes and lipofectamine-DNA complexes, cell sonication, gene bombardment using high velocity microprojectiles, and receptor-mediated transfection (Wu and Wu, 1987; Wu and Wu, 1988). Some of these techniques may be successfully adapted for in vivo or ex vivo use.

In a further embodiment of the invention, the expression construct may be entrapped in a liposome. Liposome-mediated nucleic acid delivery and expression of foreign DNA in vitro has been very successful. Wong et al. (1980) demonstrates the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection.

1. Regulatory Elements

The terms "expression construct" or "expression vector" are meant to include any type of genetic construct containing a nucleic acid coding for a gene product in which part or all of the nucleic acid coding sequence is capable of being transcribed. In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent and under the control of a promoter that transcriptionally active in human cells. Generally speaking, such a promoter might include either a human or viral promoter.

In various embodiments, the human cytomegalovirus (CMV) immediate early gene promoter, the SV40 early promoter, the Rouse sarcoma virus long terminal repeat, rat insulin promoter, and glyceraldehyde-3-phosphate dehydrogenase promoter can be used to obtain high-level expression of the coding sequence of interest. The use of other viral or mammalian cellular or bacterial phage promoters that are well-known in the art to achieve expression of a coding sequence of interest is contemplated as well, provided that the levels of expression are sufficient for a given purpose.

Where a cDNA insert is employed, one will typically include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression construct is a terminator. These elements can serve to enhance message levels and to minimize read through from the construct into other sequences.

2. Selectable Markers

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin, and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

B. Ex Vivo Transformation

Methods for transfecting cells and tissues removed from an organism in an ex vivo setting are known to those of skill in the art. For example, canine endothelial cells have been genetically altered by retrovial gene tranfer in vitro and transplanted into a canine (Wilson et al., 1989). In another example, yucatan minipig endothelial cells were transfecteded by retrovirus in vitro and transplated into an artery using a double-balloon catheter (Nabel et al., 1989). Thus, it is contemplated that cells or tissues may be removed and transfected ex vivo using the nucleic acids of the present invention. In particular aspects, the transplanted cells or tissues may be placed into an organism. In preferred facets, a nucleic acid is expressed in the transplated cells or tissues.

IV. Therapeutic Gene

The term "gene" is used for simplicity to refer to a functional protein-, polypeptide-, or peptide-encoding unit. "Therapeutic gene" is a gene which can be administered to a subject for the purpose of treating or preventing a disease. For example, a therapeutic gene can be a gene administered to a subject for treatment or prevention of cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, α-1 antitrypsin, glucose-6-phosphatase, low-density-lipoprotein receptor, porphobilinogen deaminase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

As will be understood by those in the art, the term "therapeutic gene" includes genomic sequences, cDNA sequences, and smaller engineered gene segments that express, or may be adapted to express, proteins, polypeptides, domains, peptides, fusion proteins, and mutants. The nucleic acid molecule encoding a therapeutic gene may comprise a contiguous nucleic acid sequence of the following lengths or at least the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

Encompassed within the definition of "therapeutic gene" is a "biologically functional equivalent" therapeutic gene. Accordingly, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of the therapeutic gene will be sequences that are biologically functional equivalents provided the biological activity of the protein is maintained.

In particular embodiments, the invention concerns isolated nucleic acid segments and recombinant vectors incorporating DNA sequences that encode one or more therapeutic genes. Vectors of the present invention are designed, primarily, to transform cells with a therapeutic gene under the control of regulated eukaryotic promoters (i.e., inducible, repressable, tissue specific). Also, the vectors may contain a selectable marker if, for no other reason, to facilitate their manipulation in vitro. However, selectable markers may play an important role in producing recombinant cells.

V. Pharmaceutical Compositions

Where clinical applications are contemplated, it may be necessary to prepare pharmaceutical compositions—expression vectors, virus stocks, cells, and the like—in a form appropriate for the intended application. Generally, this will entail preparing compositions that are essentially free of impurities that could be harmful to humans or animals.

One generally will desire to employ appropriate salts and buffers to render delivery vectors stable and allow for uptake by target cells. Buffers also are employed when recombinant cells are introduced into a patient. Aqueous compositions of the present invention may comprise an effective amount of a cell, protein, peptide, antibody, fusion protein, recombinant phage and/or expression vector, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the proteins or peptides of the present invention, its use in therapeutic compositions is contemplated. Supplementary active ingredients also can be incorporated into the compositions.

Administration of compositions described herein may be via any common route so long as the target tissue is available via that route. This includes oral, nasal, buccal, rectal, vaginal or topical. Alternatively, administration may be by orthotopic, intradermal, subcutaneous, intramuscular, intraperitoneal, intraarterial or intravenous injection. Such compositions normally would be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and may be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compositions in the required amount in the appropriate solvent with various other ingredients enumerated above, as required, followed by filtered sterilization were applicable. Generally, dispersions are prepared by incorporating the various sterilized active ingredients into a sterile vehicle which contains the basic dispersion medium and the required other ingredients from those enumerated above.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Analysis of Feline Immunodeficiency Virus Vector Integration

A. Materials and Methods

FIV vector constructs and particle production. Vesicular stomatitis virus G protein (VSV-G)- or *Autographa californica* multinuclear polyhedrosis baculovirus (AcMNPV) GP64-pseudotyped FIV vector particles were produced using a three-plasmid expression system as described (Johnston et al., 1999; Kumar et al., 2003; Wang et al., 1999; Sinn, et al., 2005). The vector constructs encoding enhanced green fluorescence protein (eGFP) or nuclear targeted β-galactosidase driven by a CMV promoter/enhancer were used as indicated. FIV viral particles were generated by transient transfection of 293T cells with packaging, envelope, and vector plasmids, followed by collection of supernatants and particle concentration by centrifugation as previously reported (Johnston et al., 1999; Wang et al., 1999). Transduction titers were determined by measurement of eGFP or β-galactosidase positive cells in transduced HT-1080 target cells, and expressed as transducing units (TU)/ml.

FIV transduction of human HepG2 hepatoma cell line in vitro. HepG2 cells (HB-8065, ATCC, Rockville, Md.) were cultured in EMEM supplemented with 10% FBS, 100 U/ml penicillin, 100 mg/ml streptomycin, 1.5 g/L sodium bicarbonate, 1 mM sodium pyruvate, and 0.1 mM non-essential amino acids. The cells were transduced with VSV-G/FIV-eGFP vector at multiplicity of infection (MOI) of 0.1-1. At the time-points indicated, the eGFP transgene expression was measured by FACS analysis and the genomic DNA isolated using the DNeasy Tissue Kit (Qiagen, Valencia, Calif.) following the manufacturer's protocol.

FIV transduction of mouse hepatocytes in vivo. To investigate the sites of FIV integration in vivo, one-month old C57B1/6 mice were injected via tail vein over two consecutive days with $2.4 \times 10^8$ TU of GP64/FIV vector expressing nuclear-targeted β-galactosidase under the RSV promoter. Three weeks post injection, the mice were sacrificed and the liver isolated for DNA extraction, restriction enzyme digestion, and adaptor-ligated, nested PCR to map integration sites as described below. DNA from four different mice was analyzed.

Construction of GenomeWalker™ DNA libraries. To construct a library of DNA fragments containing the host genomic DNA sequences adjacent to the FIV viral LTR, an adaptor-ligated, nested PCR technique was used per the manufacturer's instructions (GenomeWalker™ kit, BD Biosciences, Palo Alto, Calif.). Briefly, the HepG2 cell or mouse liver genomic DNA isolated following FUV transduction was digested with either EcoRV or StuI restriction enzymes. The enzyme digestion products were then ligated with the GenomeWalker™ adaptor at 16° C. overnight, and subsequently underwent two rounds of PCR with GenomeWalker™ adaptor (AP)- and FUV viral gag (GSP)-specific primers. The first or primary PCR used the outer adaptor primer (AP1) provided in the kit and an outer, FIV gag-specific primer (GSP1,5'-CCCTCGGCGAATCTCCTG-GCTTGAA-3', SEQ ID NO: 1). The secondary or nested PCR used the nested AP2 primer and a nested FIV-specific primer (GSP2,5'-GCGTCTGCTACTGCTTCCCTATTT-3', SEQ ID NO:2). The nested PCR products were visualized on a 1.5% agarose, ethidium bromide stained gel.

Cloning and sequencing of FIV integration sites. To map FIV integration sites in HepG2 cells, genomic DNA isolated from 16 days after transduction was used. Genomic DNA isolated from the liver three weeks after FUV gene transfer was used in the mouse mapping studies. The resultant pool of nested GenomeWalker™ PCR products was cloned into pCR2.1-TOPO vector (Invitrogen, Carlsbad, Calif.) and transformed into One Shot® chemically competent *E. coli* (Invitrogen). Individual transformed clones were picked and DNA plasmids isolated using the Qiagen™ mini prep kit (Qiagen). The GenomeWalker™ PCR products were then sequenced using M13 forward and reverse primers.

Bioinformatic Analysis of FIV Integration Sites.

Mapping. All insert sequences were obtained from the University of Iowa DNA sequencing core (dna-9.int-med.uiowa.edu/) and transferred to a UNIX file server in the University of Iowa Coordinated Laboratory for Computational Biology. Each sequence was then processed, so that all insert sequences were equivalent. First, each sequence was BLASTed (Altschul et al., 1990) versus a database containing the FUV construct. Only those insert sequences that aligned to the 3' TG of the FIV LTR were accepted. To ensure high sequence quality, the sequences were trimmed such that only the subsequence between the FIV LTR and the first N (non-specific nucleotide) was used as the insert sequence. If the viral LTR was observed 3' of the genomic insert, the sequence was reverse complemented. Thus, the first base of every sequence represents the base immediately adjacent to the integration site.

The sequences were then searched against the current assembly of the human or mouse genomes using BLAT (BLAST-like alignment tool (Kent, 2002)). Three criteria were applied to validate putative integration sites. These were that every sequence: 1) begins at the junction with the FIV terminal LTR sequence (5' TG 3'), 2) matches the draft human or mouse genome sequence for >98% of the length of a good quality sequence read, and 3) yields a unique best hit within the genome. When identical sequences were obtained from different clones, they were judged to represent multiple isolates of a single integration event. The human and mouse genome RefSeq (Pruitt and Maglott, 2001) tracks in the human and mouse versions of the UCSC genome database were used to determine whether integration events occurred within genes. The distribution of the integration sites within the genome was compared to randomly selected sites to determine if there was a systematic bias or preference in the specific locations of integration.

Expression analysis. To investigate whether FIV-targeted genes were transcriptionally active, publicly available HepG2 cDNA array (Stanford University) and C57BL/6 mouse liver Affymetrix array (GEO data set GDS279; C57BL/6 on low fat diet only (GSM5406, GSM5407, GSM540); (Recinos et al, 2004)) expression sets were analyzed. The probe corresponding to the FIV-targeted genes on the arrays were determined based on genome location, and their expression values were contrasted with those of all genes on the array. Analysis of the microarray expression data was performed as described by Bushman et al. (2002). The mean expression values were used to compare the expression of genes containing integrations with the set of probes on the array. In addition, FIV-targeted genes were identified based upon integrations within UniGene (Schuler et al., 1997) and TIGR Tentative Consensus (Quakenbush et al., 2001) tracks at the UCSC genome database. Expression in the liver was then assessed using the annotated tissue for the constituent ESTs.

Identification of integration hot-spots. Local integration "hot spots" were identified as described in Bushman et al. (2002). Briefly, regions containing more than 1% of the integrations within 2.5 kb were identified as hot spots. Because a single integration in mouse is greater than 1%, at least two integrations within 2.5 kb were required in either mouse or human.

Gene density. Correlation of integration with gene density was investigated using 1 Mb regions flanking each site of integration (500 kb up- and down-stream from the integration site). The number of RefSeqs overlapping or contained within this regions were used to compute the gene density. These results were compared to the average number of RefSeqs per Mb in the entire genome for non-overlapping 1 Mb intervals. RefSeq positions were obtained from the UCSC genome database (Karolchik et al., 2003).

Integration orientation. The orientation of the integrated vector DNA within the genome and its orientation (strand) to associated RefSeq genes were assessed using the previously computed BLAT alignment (Kent, 2002) and the RefSeq orientation as annotated in the UCSC genome databases (Karolchik et al., 2003).

Correlation with repetitive elements. The correlation of the integration sites with repetitive elements was evaluated using the chromosome-specific RepeatMasker (Smit and Green, ftp.genome.washington.edu/RM/RepeatMasker.html) annotation in the UCSC human and mouse genome databases (Karolchik et al., 2003). Repeats were categorized by "repeat class" as SINE, LINE, LTR, DNA or low complexity.

Gene classification. To annotate the molecular functions of the FIV-targeted human and mouse RefSeq genes, GeneOntology (GO; (Ashbumer et al., 2000)) terms were used. The GO terms were determined using the DAVID (Database for Annotation, Visualization and Integrated Discovery) system ((Dennis et al., 2003); apps1.niaid.nih.gov/david).

Physical properties of DNA at integration sites. B-DNA twist, A-philicity, DNA bendability and protein-induced deformability were measured as previously described by Voytas and colleagues (Vigdal et al., 2002). The genomic sequence flanking the point of integration 20 bp up- and down-stream were used in this analysis. All calculations were done using a two or three base-pair sliding window to incorporate effects of adjacent nucleotides on the various biological properties. These properties of FIV insertion sites were compared to three randomly selected controls. These controls utilized a randomly selected set of sequences from the human (or mouse) genome assembly. This set was constructed such that the number of random regions selected from a particular chromosome is equal to the number of integrations in that chromosome.

Free Energy Calculation. A second computational approach was used to calculate the free energy required for DNA strand opening in the region adjacent to the sites of integration. The free energy $G(x)$ required by the base pair at position x in a superhelically stressed DNA sequence to separate to single stands was calculated. This was done for each base pair in the sequence using previously reported methods (Benham, 1992; Benham, 1993).

Each available state of this system contributes to the equilibrium distribution in inverse proportion to the exponential of its energy G. From the calculated equilibrium distribution the value of $G(x)$ was evaluated for each base pair. All the conformational and energy parameters are assigned their experimentally measured values. Here the inventors use energy parameters appropriate to T=37° C. and $[Na^+]$=0.01M, the conditions of the Kowalski nuclease digestion procedure by which superhelical denaturation is most accurately evaluated (Kowalski et al., 1988). The inventors assumed a superhelix density of $\sigma$=-0.055, a moderate physiological value. Although there are no free parameters in these calculations, they accurately determine how destabilization varies along the sequence (Benham, 1992; Potaman et al., 2003). Many sites that these methods had previously calculated to open under stress have subsequently been experimentally shown to separate under these conditions, both in vitro and in vivo (Benham, 1993; Sheridan et al., 1998; Fye and Benham, 1999).

Here the inventors used these methods to calculate the destabilization energy $G(x)$ for each base pair within 5,000 base pairs centered on each insertion site. For comparison the inventor calculated the destabilization experienced by control regions of the same length, selected as described above. The stability characteristics of the 20 bp centered on the integration site were also considered. Specifically, the minimum value of the free energy $G(x)$ among these 20 bp was identified. In this way a single minimum free energy value Gmin was associated with each insertion site. The inventors compared these with the similarly obtained Gmin values for the central base pair in each control region.

B. Results

FIV mediates stable integration into the genome along the length of genes. The inventors previously reported that gene transfer with FIV vectors confers sustained transgene expression in vitro and in vivo (Brooks et al., 2002, Derksen et al., 2002, Hughes et al., 2002; Johnston et al., 1999; Kang et al., 2002; Lotery et al., 2002, Stein et al., 2001; Wang et al., 1999; Sinn et al. 2005), and assumed from these findings that integration occurred. However, FIV proviral integration was not formally documented in these studies. The inventors assayed eGFP expression in HepG2 cells by FACS at intervals post transduction, and when expression was stable (~2 weeks), isolated genomic DNA, and investigated the patterns of FIV integration. As shown in FIG. 1, following an initial decline after transduction, eGFP expression in the HepG2 cells stablized and persisted over a one month period of observation. Vector integration was detected two days post transduction, the earliest time-point examined, and was present throughout the experimental period. No particular clonal selection was observed.

To map the FIV integration sites, the secondary PCR products were cloned and randomly selected and sequenced the clones. HepG2 cell integration sites were analyzed 16 days post transduction to minimize sequencing of non-integrated, circular DNA intermediates that may transiently persist as episomes (Saenz, 2004). Two blunt-end restriction enzymes, EcoRV and StuI, were used to minimize a selection bias that might occur from using a single enzyme digestion. Mouse liver integration sites were similarly cloned three weeks post gene transfer in four animals.

Figure 2A:
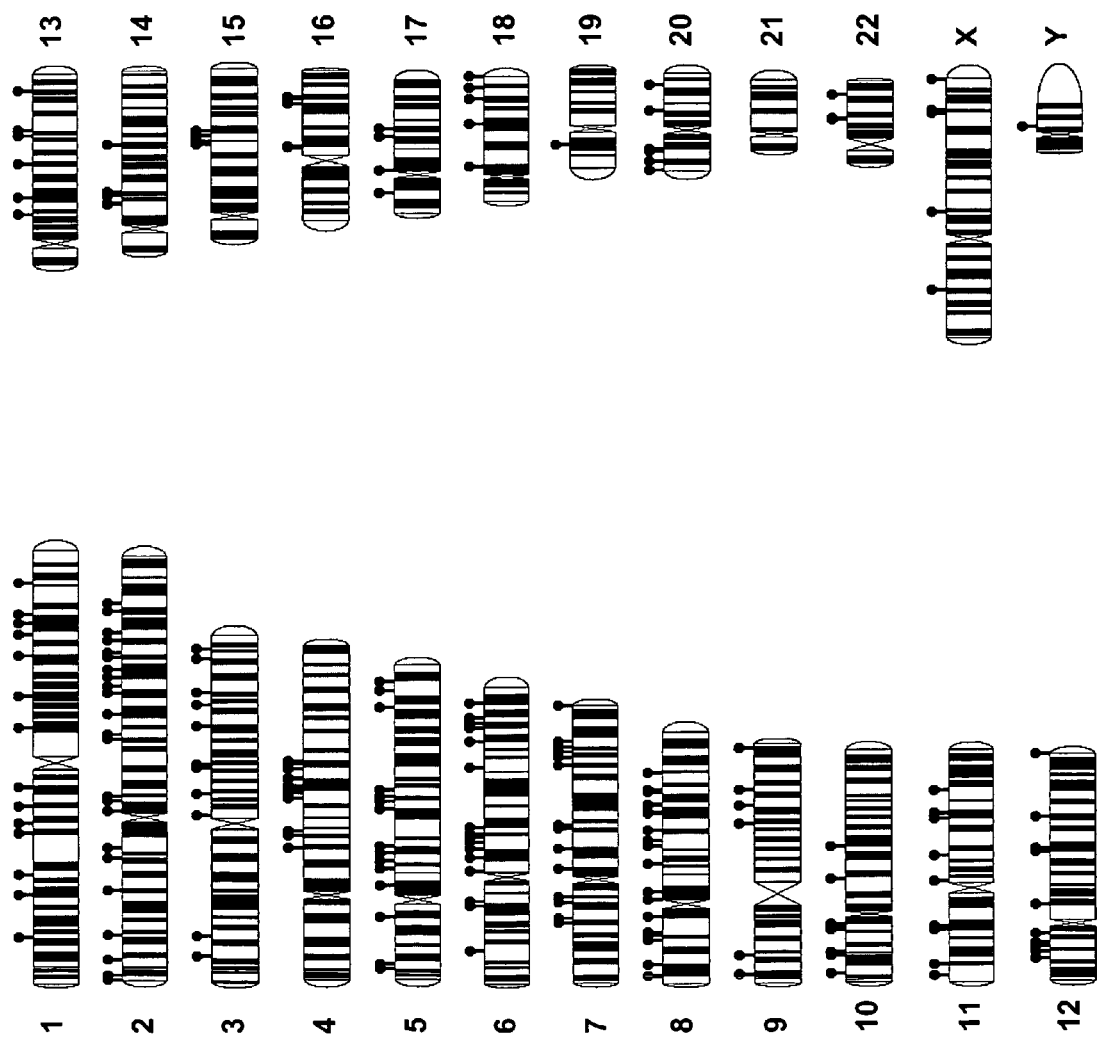
FIGS. 2A and 2B. FIV integration sites on human and mouse chromosomes. The unique FIV integration sites in all human (FIG. 2A) and mouse (FIG. 2B) chromosomes are shown. For the human chromosomes, each black dot represents one unique integration site. The on the mouse chromosomes indicate the integration sites for the four individual mice studied. Some distinct integration sites appear to overlap due to their close proximity in the genome.

For HepG2 cells, 226 distinct FIV integration sites were available for mapping. Additionally, 54 distinct integration sites were the inventors obtained in mouse liver. The distributions of FIV integration in the human and mouse genomes was first analyzed by mapping the insertion sites to individual chromosomes. As shown in FIG. 2A, HepG2 cell integration events mapped to all chromosomes except chromosome 21. Integration sites were collectively noted on all chromosomes for the four mice studied.

Thus From

Figure 2B:
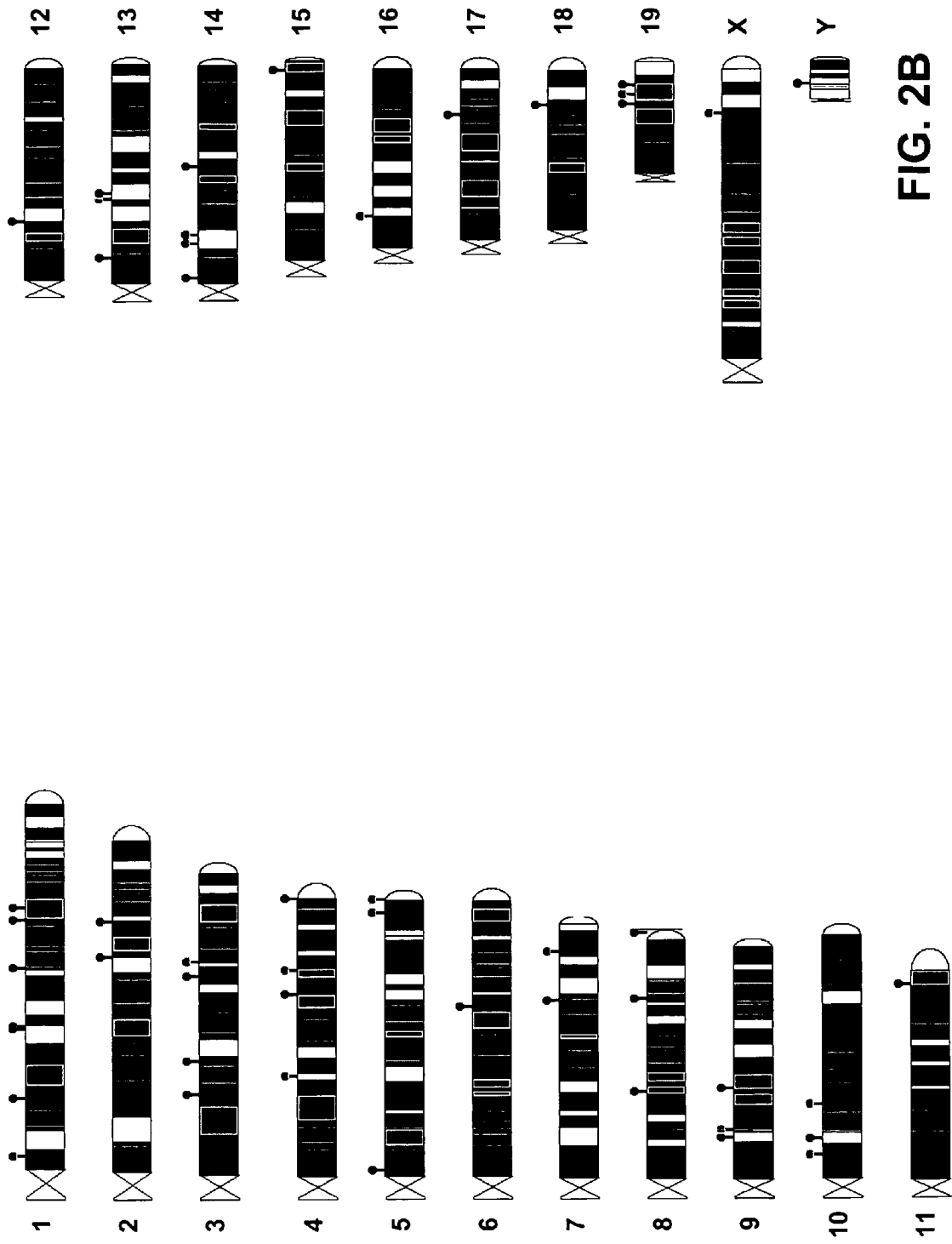

The distribution of FIV integration in the human and mouse genomes was first analyzed by mapping the insertion sites to individual chromosomes. As shown in FIG. 2A, HepG2 cell integration events mapped to all chromosomes except chromosome 21. Karyotyping demonstrated only one copy of chromosome 21 in this cell line. Integration sites were collectively noted on all chromosomes for the four mice studied (FIG. 2B).

The inventors next asked whether FIV integration favored transcriptional units. An integration site was defined as residing within a gene if it occurred between the transcriptional start site and transcriptional stop site of one of the 19,979 human or 17,078 mouse RefSeq genes as annotated in the UCSC genome database. By this definition, it was found that 168/226 distinct HepG2 cell integration sites occurred in genes (68%) and 21 of the 54 mouse liver integration sites localized to a gene (42%). Note that four of the mouse integrations fell within incomplete portions of the assembly, and were not included in this analysis. On average for both human and mouse, ~61% of FIV integration events occurred in a RefSeq. This increases to 82% if all mRNAs are used (83% in human; 80% in mouse). These percentages are similar to that reported for HIV integration (69%) (Schroder et al., 2002) and higher than those for MLV integration (34%), ASLV (Mitchell et al., see Table 1) and random integration (22.4%) (Wu et al., 2003) (Table 1). As expected, due to the relative difference in the length between introns and exons, the inventors also observed FIV integration more prevalently in introns rather than exons. Out of 168 integration sites occurring in human RefSeq genes, 163 were in introns and 5 in exons/open reading frames. Similarly, of 21 mouse liver integration sites localizing to a RefSeq gene, all occurred within intronic sequence (Table 1). The human genes with integration events occurring in exons are summarized in Table 2. It is important to note a greater fraction of the genome is covered by RefSeqs in human (28.6%) than in the mouse (23%).

TABLE 1

| | # Integration landed on a RefSeq gene | | | | | FIV integration | |
|---|---|---|---|---|---|---|---|
| | FIV | HIV[a] | MLV[b] | ASLV[c] | Random[a] | Intron | Exon |
| Human: | 168/226 | | | | | 163/168 | 5/168 |
| Mouse: | 21/54 | | | | | 21/21 | 0/21 |
| Total: | 67.5% | 69% | 34% | 38% | 22.4% | 97.43% | 2.6% |

[a]Schroder et al.
[b]Wu et al.,
[c]Mitchell et al.,

TABLE 2

Human genes with FIV exons present within exons

| Refseq | Gene name | Gene ontology |
|---|---|---|
| NM_004194 | Homo sapiens a disintegrin and metalloproteinase domain 22 (ADAM22), transcript variant 4, mRNA | integral to membrane; integrin binding; metalloendopeptidase activity; negative regulation of cell adhesion; proteolysis and peptidolysis |
| NM_014614 | proteasome (prosome, macropain) activator subunit 4 | |
| NM_015386 | component of oligomeric golgi complex 4mitofusin 1 | Golgi apparatus; intracellular protein transport; membrane; protein transporter activityGTPase activity |
| NM_017927 | mitofusin 1 | GTPase activity; biological process unknown; integral to membrane |
| NM_021931 | DEAH (Asp-Glu-Ala-His) box polypeptide 35 | ATP binding; ATP-dependent helicase activity; hydrolase activity; nucleic acid binding |

In a previous report several hot spots for HIV integration were observed in the SupT1 human T cell line (Schroder et al., 2002). These regions localized to the short arms of chromosome 1 and 6, 11 q 13, and chromosomes 16, 17 and 19. In this study, a hot spot in the human genome was defined using previously published criteria (Schroder et al., 2002); 1% of integrations within 2.5 kb. The criteria of 2 or more integration events occurring within 2.5 kb was used for both human and mouse, as a single integration in mouse represented more than 1% of all integration events. Using these criteria the inventors identified a single hot spot with two integration events in the human genome on chromosome 4 at position 123.54 Mb.MB. No hot spots were identified in mouse using these criteria, nor were any integration events localized to the mouse regions syntenic to the human hot spot. Of interest, the inventors detected a singleno FIV integration events on gene-rich chromosome 19, which had significant affinity for HIV integration. A karyotype of the HepG2 cell line revealed that chromosomes 19 was and Y were present and of normal size and banding pattern, however, one copy of chromosome 21 was missing (data not shown). This is similar to the karyotype of SupT1, except that SupT1 does not have a Y chromosome. Furthermore, three integrations occurred within the COH1 gene in human. Finally, 5three integrations were identified that occurred within exonic sequence. A description of these integrations and the genes they are associated with are included in Table 23.

Figure 3:
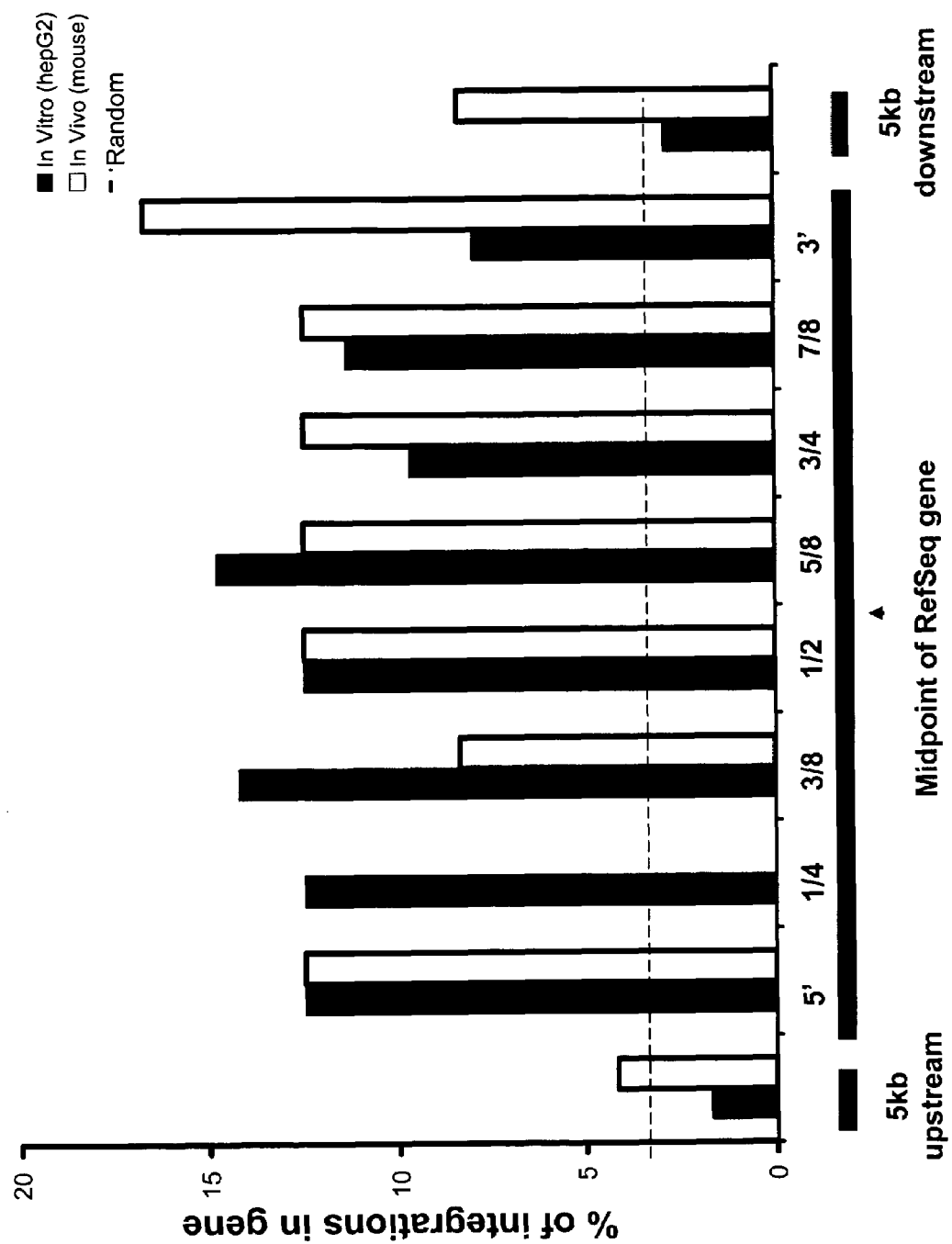
FIG. 3. Relationship of FIV integration to RefSeq genes. The cloned sequences from human and mouse cells were analyzed as described herein. The RefSeq genes with FIV integration events were divided into eight equal portions regardless of size. The percentage of integrations occurring in each portion is shown. Integration events occurring within 5 kb upstream and 5 kb downstream of the gene are also shown. Y axis=% of total integrations.

To determine if FIV integration demonstrated a preference for particular regions of genes (transcription start, intron, exon, flanking sequence, etc.), the number of FIV integration events occurring within RefSeq transcripts (exon or intron) or the adjacent 5 kb flanking regions immediately up or downstream were analyzed. For this analysis, the inventors divided the RefSeq genes into eight equal portions regardless of the size of the transcript. As shown in FIG. 3, FIV integration in HepG2 cells occurred along the entire length of RefSeq transcripts and transcriptional start regions were not favored targets for integration. The distribution pattern for integration sites in mouse liver showed a similar pattern, with no noticeable preference for any sub-region of the RefSeq transcripts (FIG. 3). The orientation of the integrations occurring within RefSeqs was also compared relative to the direction of the RefSeq's transcription. This analysis revealed no significant correlation between the orientation of viral integration and the orientation of gene transcription. Of the 149 non-redundant integrations in the human and mouse genomes that localized within a transcribed gene, 64 were in the same orientation, and 76 were in the opposite orientation with respect to the gene they were integrated within. The remaining 9 integrations occurred in regions of bi-directional transcription.

Figure 4:
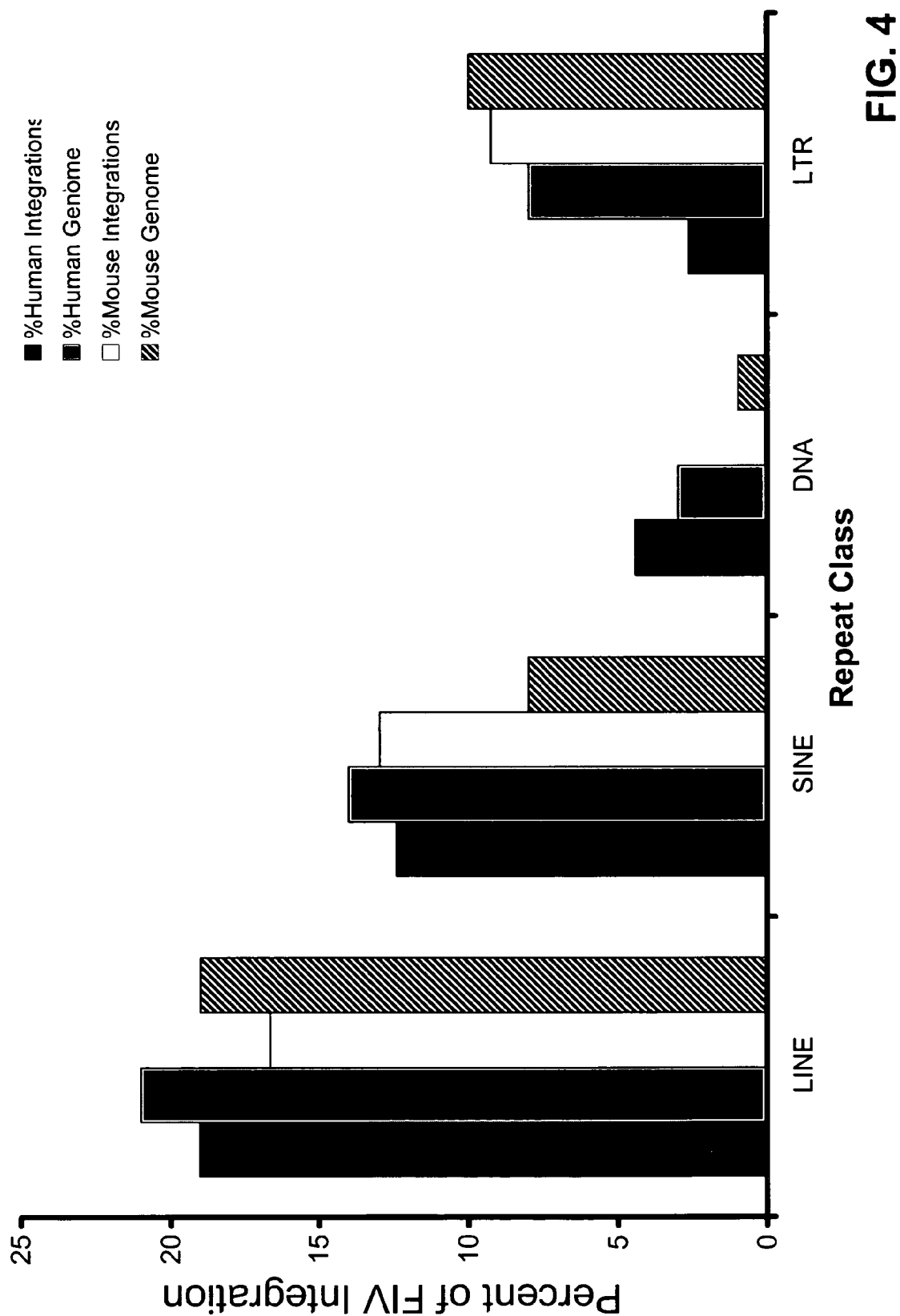
FIG. 4. Integration of FIV within regions of repetitive human and mouse genomic DNA. Sites of integration in human and mouse genomes were classified by their locations in LINE, SINE, low complexity DNA, and LTR elements.

In addition to identifying genes as preferred sites for FIV integration, the inventors asked whether regions of repetitive genomic DNA were preferentially targeted for integration. This analysis quantified integration in SINE (short interspersed nuclear element), LINE (long interspersed nuclear element), LTR (long terminal repeat), DNA class repeats (e.g., the Mer and Mariner repeat families), and low complexity (simple) repeats as annotated in the UCSC genome database. As shown in FIG. 4, for both human and mouse events, integration sites were present in SINE, LINE, and LTR repeats. While 13 human integrations occurred in DNA class repeats, no mouse integration events were found in this class of repeat (likely because it is less prevalent in the mouse). Few integrations occurred in low complexity repeats for either human or mouse. In general, the frequency of integration events in these regions reflects the frequency of representation of these elements in the genome.

To examine whether functional classes of genes were preferentially targeted by the FIV vector in human or mouse cells, the RefSeq genes with integration events were categorized using gene ontology terms (GO terms). Gene ontology divides genes into several main classes according to their molecular functions and each class is further subdivided into several subclasses (www.geneontology.org/). This analysis revealed that FIV integration occurred within human or mouse RefSeq genes representing a variety of gene classes including those involved in molecular binding, catalytic activity, cell signaling, transmembrane transporter, and transcription/translation regulation. However, the pattern of gene classes targeted was very similar to the distribution of all RefSeq genes, suggesting no preferential targeting of particular gene classes (data not shown).

Gene density was also assessed to determine if the association with transcribed regions reflected a bias towards gene-rich regions. This analysis was performed on 1 MbMB intervals flanking the viral integration sites, compared to all non-overlapping 1 MbMB regions in the human or mouse genomes. However, no such bias was observed with nearly identical numbers of transcripts in either the human or mouse data (data not shown).

Sites of integration correlate with transcriptional activity. The inventors analyzed the transcriptional profile of HepG2 cells and mouse liver using publicly available gene expression data sets. The microarray data for HepG2 cells consisted of cDNA array data for 12,356 genes. Of the 16890 RefSeq genes that were targeted by FIV in HepG2 cells, 50 were represented on the microarray data set. The median expression level for these 50 genes was 246, and was 6.3-fold higher than that of all the genes on the array (median expression levels for all genes on the array was 39). Similarly, for the 21 mouse RefSeq genes with evidence of integration, 14 were represented on the U74 version 2 Affymentrix array probe set. A similar increase in the median expression level (2.8 fold) was observed in those probes with integration versus all probes. These results support the notion that the FIV vector integrates into regions of chromatin that are transcriptionally active. Expression was also analyzed using the collection of ESTs in the human and mouse UniGene sets to determine which genes are transcribed in liver. This analysis demonstrated that, of the genes that could be correlated to NCBI's UniGene, approximately 90% (94/104) of human genes, and 72% (28/39) mouse genes exhibited some level of expression in liver.

Correlations between LEDGF/p75 regulated genes and FIV integration. LEDGF/p75 (PSIP 1) interacts with the pre-integration complexes of HIV and FIV IN (but not MLV) directing the complex to specific regions of chromosomal DNA and acting as a tethering protein (Busschots, 2005; Llano, 2004). Interestingly, sites of HIV integration correlate with LEDGF/p75 regulated genes and genetic manipulation of cells to knock down PSIP1 expression changed the HIV integration pattern away from LEDGF/p75 regulated genes (Ciuffi, 2005). This approach identified 1,849 LEDGF/p75 regulated Entrez genes on the Affymetrix U133 Plus2 genechip. It is unknown whether the sites of FIV integration correlate with LEDGF/p75 regulated genes. Using this same microarray data set to identify LEDGF/p75 regulated genes (Ciuffi, 2005), the inventors then assessed for correlations between FIV integration sites and genes regulated by this transcriptional coactivator. Strikingly, ~22% (37/168) of the FIV integrations occurred in LEDGF/p75 regulated genes (p=0.000006 by Fisher's Exact Test vs random integration). This contrasts with 14% of HIV integrations localizing to LEDGF/p75 regulated genes in 293T cells (Ciuffi, 2005). Recently, the solution structure of HIV IN interacting with the LEDGF/p75 IN binding domain was solved (Cherepanov, 2005). These studies showed that LEDGF residues essential for the interaction with IN were localized to inter-helical loop regions of the bundle structure. These structural studies showed that for HIV, IN residues H12N and Q168A were important in mediating interactions with LEDGF/p75. FIG. 10 shows an alignment of the primary amino acid sequences of the HIV and FIV integrase proteins. Based on this alignment, the inventors deduced that in FIV, residues H14 and E170 are critical in mediating high affinity interactions with LEDGF/p75. Furthermore, based on the discovery that a very significant proportion of FIV integration events occur in LEDGF/p75 regulated genes, the present invention also includes introduction of specific modifications in the FIV IN (H14N and E170A, see FIG. 10) by site directed mutagenesis to inhibit native interactions between FIV IN and host cell LEDGF/p75. This aspect of the invention creates more favorable conditions for the engineered recombinant FIV IN with a carboxy terminal domain comprising a non-native protein binding site (such as NpwBP) to direct a retroviral preintegration complex to the engineered DNA binding protein.

DNA Structural Correlates of FIV Integration.

Sequence composition. The specific composition of the integration sites was assessed using standard techniques to assess for nucleotide bias as well as to determine if there were any sequence-specific motifs at or near the site of integration. This analysis revealed no specific DNA motif preferred for FIV integration as measured with Gibb's sampler (Thompson et al., 2003).

DNA structural features in regions of integration. The inventors examined the structural properties of the human and mouse DNA sequences containing the FIV integration sites. Regions consisting of 20 bases flanking either side of the FIV insertion site were analyzed for physical properties including B-DNA twist, A-philicity, DNA bending and protein-induced deformability using previously reported methods (Vigdal et al., 2002). B-DNA twist reflects the tightness of the DNA structure while A-philicity indicates the ability of DNA to form an A-DNA-like double helix. DNA bending models the ability of DNA to modify the depth and width of the major and minor grooves, and may correlate with accessibility of DNA for binding by proteins or protein/DNA complexes. Protein-induced deformability indicates the capacity of DNA structure to change upon interaction with a protein.

Figure 5:
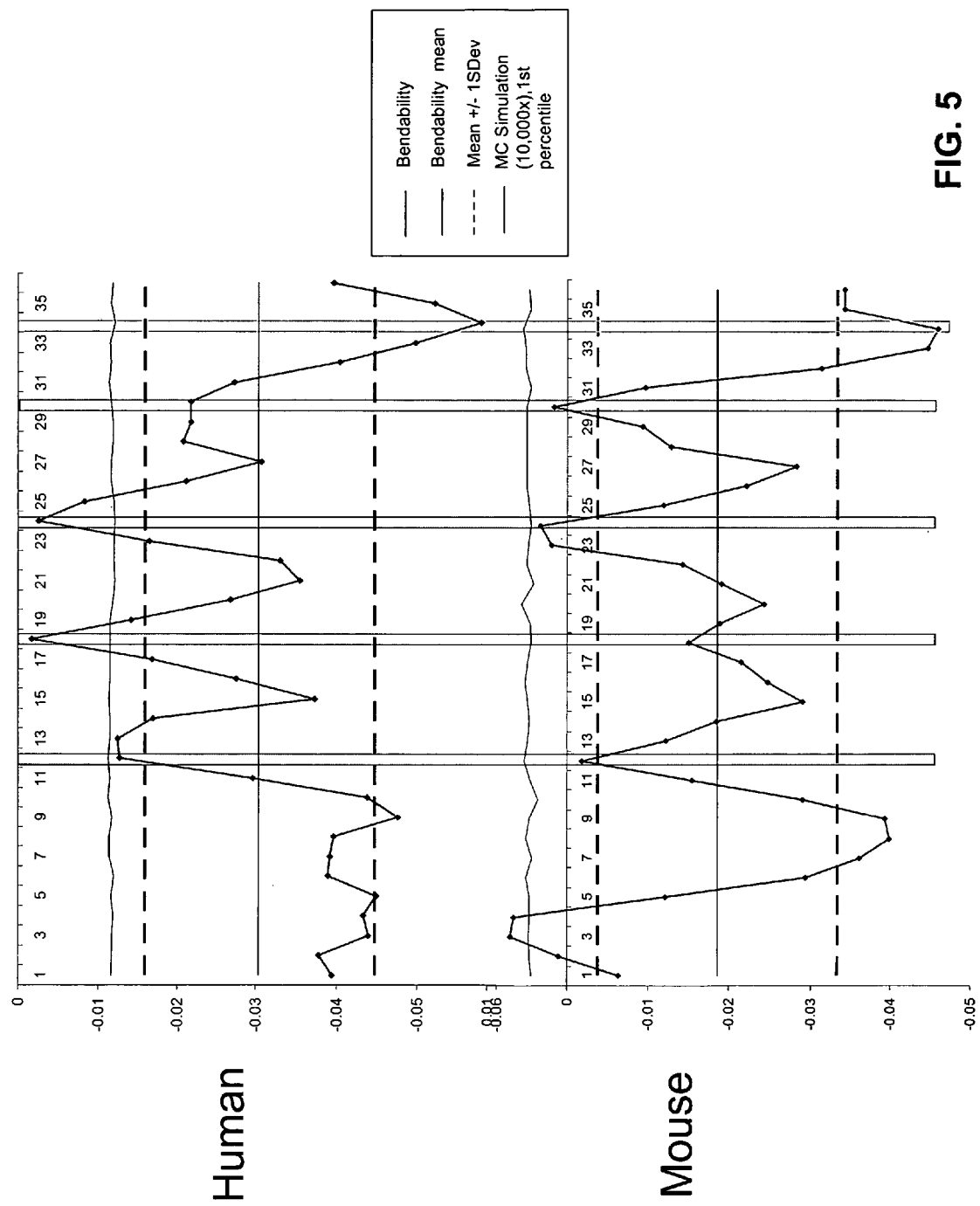
FIG. 5. Bendability of DNA near sites of FIV integration. DNA flanking the point of integration 20 bp up- and downstream of the FIV insertion sites were analyzed and compared to means as indicated and described herein. Base position 20 corresponds to the FIV insertion site. The boxes denote regions of similarity for both mouse and human flanking DNA sequence.

Three sets of randomly selected control sequences were similarly analyzed and contrasted with FIV integration regions. In addition, a set of repeatedly shuffled FIV integration site sequences was also utilized, providing an identical per-site nucleotide composition, while varying the dinucleotide and trinucleotide composition (data not shown). No significant differences were observed in the physical properties of B-DNA twist, A-philicity or protein-induced deformability between the area of FIV integration sites and controls (data not shown). In contrast, for both human and mouse sequences, predicted DNA bendability significantly deviated from the controls in the immediate vicinity of the insertion sites (FIG. 5, position 2418). In addition, peaks were observed at 6 bp intervals in both the human and/or mouse data, specifically at positions 12, 18, 24, and 30. These were consistently increased in both the human and mouse integrations sets. These results suggest that FIV integration sites demonstrate distinct physical properties.

Figure 6:
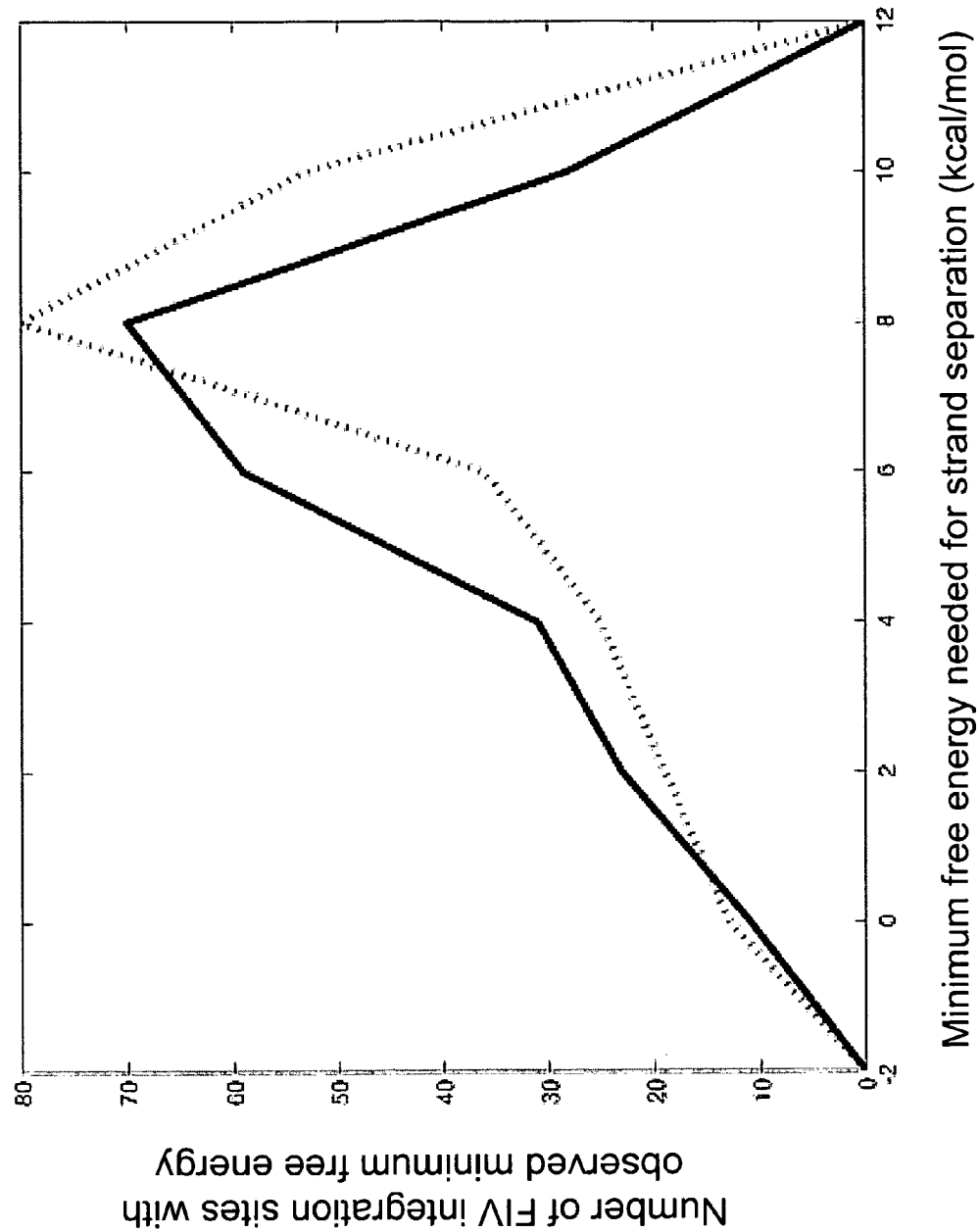
FIG. 6. Histograms of the minimum free energy $G_{min}$ needed for strand separation at the FIV insertion sites (solid line) and control sites (dashed line). The two distributions differ in the medians by 1.4 kcal/mol, which makes strand separation at the insertion sites 9.5 times more frequent at equilibrium. The probability of this pattern arising by chance is p=0.009. Y axis=Number of FIV integration sites with observed minimum free energy.

Free Energy. An additional analysis of physical properties was performed, comparing the free energy at the integration site. The distributions of Grin values for the insertion and the control sites were compared. Specifically, they were assessed for statistical significance in two ways, using first the Wilcoxon rank sum test (DeGroot, 1975) for the difference in medians and second the Kolmogorov Smirnoff test (Chakravarti et al., 1967). Both are non-parametric tests that are not sensitive to the nature of the distributions. As such, they are applicable to distributions that are not Gaussian, as in the present case. The inventors assessed the differences at a 0.05 significance level, and obtain a p-value for each test. This analysis revealed that a significantly destabilized region (p-values in the range of $10^{-3}$ to $10^{-4}$) occurs roughly within 150 bp to either side of the insertion points, and a second destabilized region occurs 600-800 bp to the 5'end of the insertion site. The distribution of sites based upon minimum free energy calculated over an N bp window is show in FIG. 6.

Example 2

Controlling Integration Specificity of a Yeast Retrotransposon

Like retroviruses, retrotransposons integrate nonrandomly into eukaryotic genomes. For the yeast retrotransposon Ty5, integration preferentially occurs within domains of heterochromatin. Targeting to these locations is determined by interactions between an amino acid sequence motif at the C terminus of Ty5 ININT called the targeting domain, and the heterochromatin protein Sir4p. Ty5 target specificity has been altered by replacing the ININT targeting domain with other peptide motifs that interact with known protein partners. Integration occurred at high efficiency and in close proximity to DNA sites where the protein partners were tethered (Zhu et al., 2003; Sandmeyer, 2003). These recent novel findings define a mechanism by which retrotransposons shape their host genomes and suggest ways in which retroviral integration can be controlled.

Figure 8:
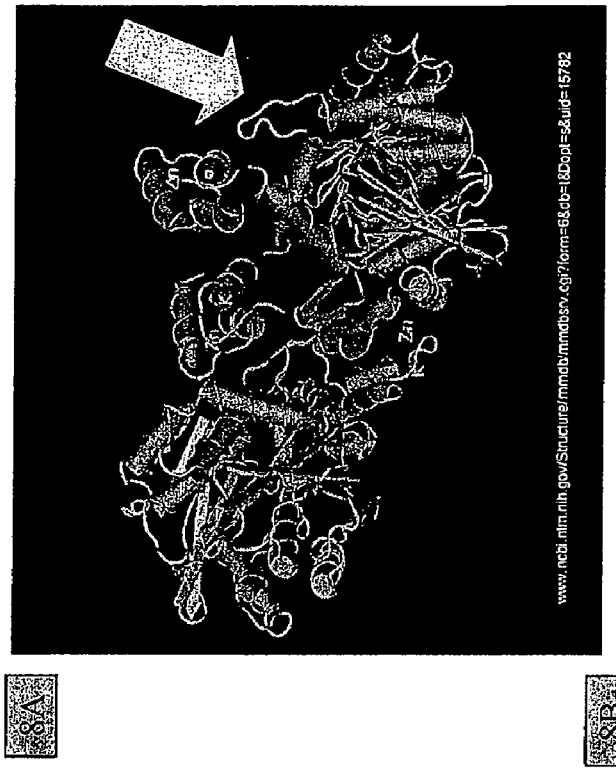
FIGS. 8A-8B. The structure of HIV-1 integrase and the proposed modifications to FIV integrase.

A similar strategy to modify and target, for example, FIV IN is described herein. In this example, FIV is modified to carry short proline rich peptides that interacts with known proteins or protein domains (WW domains). Initial studies used the well-characterized proline rich PY motif from p53-binding protein (Espanel and Sudol, 2001) and the PGR motif from human NpwBP (Komuro et al., 1999) (FIG. 8B). Yeast two-hybrid assay are used to ensure that modified integrases interact with the appropriate partner. The protein partners will be fused to the zinc-finger DNA binding domain of the mouse transcription factor Zif268 (SEQ ID NO:20). Alternatively one could use lac repressor or other DNA binding domains known in the art. The vector sequences should recognize and integrate adjacent to DNA sites occupied by Zif268 both in vitro and in vivo. Initially the zinc finger DNA binding domain of Zif268 was chosen because it is readily accessible and has been well-characterized both in vitro and in vivo. However, one advantage of using zinc finger DNA binding proteins is that they can be engineered to recognize any DNA sequence, as described above. Designed zinc fingers can be employed to direct the modified gene transfer elements to integrate into safe regions of the genome.

Example 3

ModificationModifcation of FIV Integrase (FIV-IN) to Insert a High-Affinity Protein Binding Motif The modification process involves introducing a cloning site in the region encoding the unstructured loop in the integrase protein (FIG. 8B). Using site directed mutagenesis, a BstEII restriction enzyme site was introduced into the center of the unstructured loop resulting in two amino acid substitutions (FIG. 8B). This modified packaging construct was used to generate a preparation of VSV-G pseudotyped FIV vector expressing nuclear target β-galactosidase and was titered on HT1080 cells. The titer of this preparation following the standard 250-fold centrifuge concentration was remarkably high: $1.7 \times 10^7$ TU/ml. The average titer of this vector formulation using a packaging construct with wild-type IN is approximately $5 \times 10^8$ TU/ml following 250-fold centrifuge concentration.

The next step in the IN modification process is the insertion of proline-rich peptide motifs (protein binding site). For the initial studies, the 12 amino acid proline-rich motifs from NpwBP (SEQ ID NO: 8 and 9) and p53-BP(SEQ ID NO: 10 and 11) (Espanel and Sudol, 2001; Komuro et al., 1999) were cloned into the engineered BstEII site (FIG. 8B). The titers of FIV-vector with the NpwBP and p53-BP domains inserted into IN protein were $1.3 \times 10^8$ and $7 \times 10^6$ TU/ml, respectively. This is an important and novel finding because the successful packaging of a modified IN protein into a functional viral vector has not been reported. For further in vitro and in vivo studies these titers are quite acceptable.

The portion of the exemplary FIV integrase modified extends from 13 amino acids downstream of the E residue (part of the DDE domain that defines the catalytic site) to the end of integrase (FLPETTSLDNALSLAVHSLNFKRR-GRIGGMAPYELLAQQESLRIQDYFSAIPQKL QAQWIYYKDQKDKKWKGPMRVEWGQGSV-LLKDEEKGYFLIPRRHIRRVPEPCALPEGDE QAQW YYKDQKDKKWKGPMRVEWGQGSV-LLKDEEKGYFLIPRRHIRRVPEPCALPEGDES SEQ ID NO:3). Reasons to pick this region include (1) it starts from the first coiled region after the DDE catalytic; (2) it is the first coiled region before the coiled region in the central flap; (3) it includes the end of integrase domain.

Example 4

Retention of Modified FIV-Based Vector Integrase (IN) Activity

In preliminary studies, the inventors have not observed significant reductions in vector titer with proline-rich peptides inserted into IN. However, this is, at best, an indirect indication of integrase activity. For the purposes of developing site-specific vectors, it is important to determine whether integrase catalytic activity is negatively affected by the manipulations. As a measure of integrase activity, an in vitro integrase activity assay is performed.

Methods: Integrase typically carries out two reactions: (1) it removes two bases from the 3'-end of the viral cDNA, and (2) it carries out an end joining reaction between the cDNA and the chromosomal target. Both the 3'-end processing and 3'-end joining reactions can be measured using a $^{32}$P labeled double-stranded oligonucleotide substrate containing the terminal U5 portion of the FIV LTR sequence (Tan et al., 2004). Modified IN, substrate DNA, and target DNA (unlabeled double-stranded oligos) will be incubated together. The reaction is stopped and the mixture is separated by PAGE and visualized by phosphorimaging. Functional 3'-end processing results in a band 2 bp smaller than the full length labeled oligo. Functional 3'-end joining results in the production of strand transfer products that appear as a ladder of bands greater in size than the labeled oligo.

The unmodified FIV-IN will serve as the positive control in such studies. Results will provide an indication of which, if any, modifications to IN significantly alter integrase function. Because suitable vector titers are an indication of functional integrase, it is not anticipated that measurable activity will be completely lost. However, an indication of relative activities and how those activities correlate to titer will provide information as to how well the packaged vector will tolerate modification.

Example 5

Tether Modified FIV-IN to WW/Zif268 Hybrid Protein

Modification of FIV-IN and successful vector packaging is an important and novel first step. However, for the success of directed integration, it must be demonstrated that modified FIV IN can recognize (be operatively coupled to) its DNA-binding partner. This was assessed by yeast two-hybrid system (Xie et al. 2001).

Figure 9:
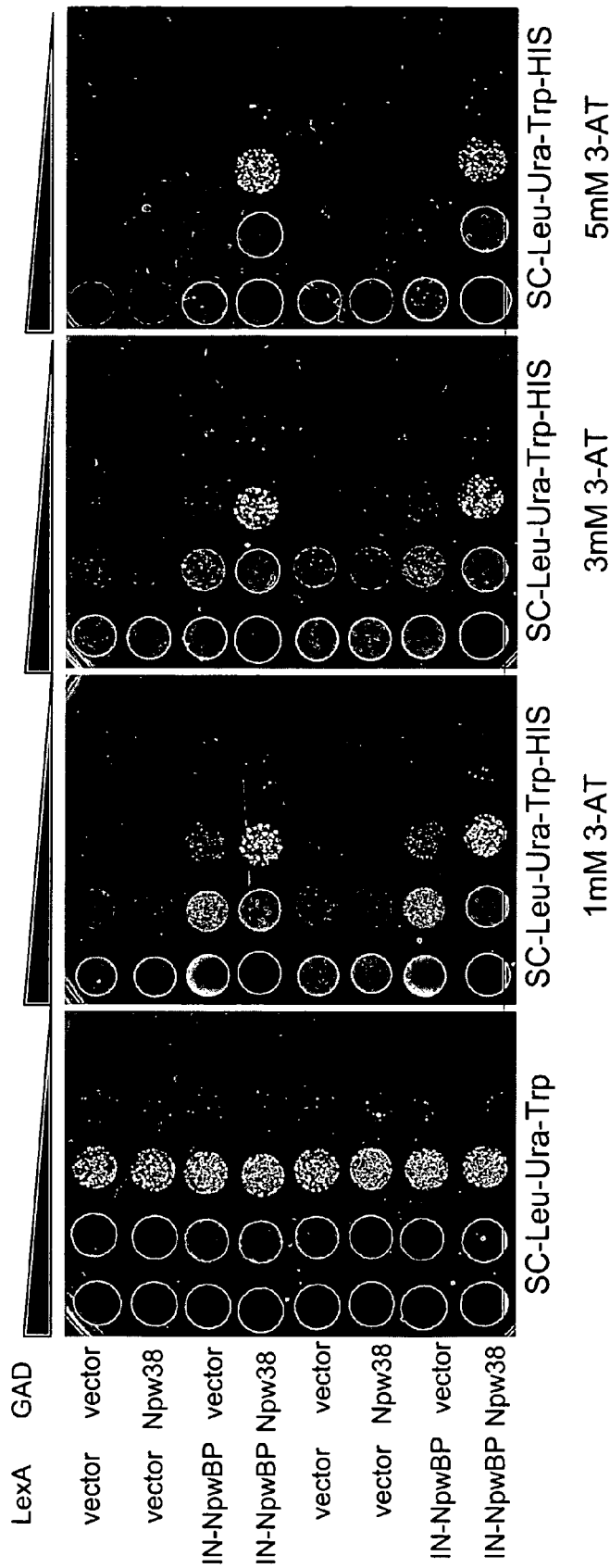
FIG. 9. Illustrates an exemplary yeast two hybrid study. The portion of FIV integrase used in this experiment extends from 13 amino acids downstream of the E residue (part of the DDE domain that defines the catalytic site) to the end of integrase (FLPETTSLDNALSLAVHSLNFKRRGRIG-GMAPYELLAQQESLRIQDYFSAIPQKL QAQWIYYKDQKDKKWKGPMRVEYWGQGS-VLLKDEEKGYFLIPRRHIRRVPEPC ALPEGDE (SEQ ID NO. 3). This region was selected in part, because it starts from the first coiled region after the DDE catalytic domain, it is the first coiled region before the coiled region in the central flap, and it includes the end of integrase. Two independent colonies were picked for each yeast transformation and two-hybrid interactions were tested for both colonies (upper four and lower four rows). Serial dilutions of cultures were spotted onto non-selective media to control for cell number (panel 1) or onto selective media with varying concentrations of 3-AT (remaining panels) to test for interactions. The only significant interaction is between IN-NpwBP and Npw38.

Methods: A region of FIV integrase carrying the Npw binding protein modification was cloned as a fusion to the Gal4p activation domain (GAD). The integrase:GAD fusions was tested for their ability to bind to the Npw38 protein partner fused to LexA. A positive interaction activates transcription of a yeast marker gene and allows growth on selective media. Controls included GAD fused to wild-type integrase, as well as GAD and LexA alone. As shown in FIG. 9, this experiment verifies that the modified integrase can interact with its binding partner on a DNA binding protein. Protein levels can also be measured by western blot analysis to ensure that all fusion constructs are expressed at comparable levels.

These studies assess whether the conformation and/or positioning of the interacting peptides to recognize the protein partner is proper, and will be used to evaluate all potential binding partners. New constructs will be generated and tested wherein the peptides are flanked by additional linker sequence or inserted into other unstructured loops. This will also necessitate testing such constructs for their effects on vector titer and activity of the modified integrases.

All of the compositions and methods disclosed and claimed herein can be made and executed without undue experimentation in light of the present disclosure. While the compositions and methods of this invention have been described in terms of preferred embodiments, it is apparent to those of skill in the art that variations maybe applied to the compositions and methods, and in the steps or in the sequence of steps of the methods described herein without departing from the concept, spirit and scope of the invention. More specifically, it is apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,206,347
U.S. Pat. No. 5,399,346
U.S. Pat. No. 5,401,511
U.S. Pat. No. 5,603,872
U.S. Pat. No. 5,889,155
U.S. Pat. No. 6,720,181
U.S. Patent Appln. 20030119023
U.S. Patent Appln. 2004110923
Altschul et al., *J. Mol. Biol.*, 215: 403-410, 1990.
Appa et al., *J. Biol. Chem.*, 276: 45848-45855, 2001.
Ashburner et al., *Nat. Genet.*, 25: 25-29, 2000.
Baichwal and Sugden, In: *Gene Transfer*, Kucherlapati (Ed.), NY, Plenum Press, 117-148, 1986.
Barany and Merrifield, In: *The Peptides*, Gross and Meienhofer (Eds.), Academic Press, NY, 1-284, 1979.
Bell et al., *Science*, 291: 447-450, 2001.
Benham, *J. Mol. Biol.*, 225: 835-847, 1992.
Benham, *Proc. Natl. Acad. Sci. USA*, 90: 2999-3003, 1993.
Broach et al., *Cell*, 29: 227-234, 1982
Brooks et al., *Proc. Natl. Acad. Sci. USA*, 99: 6216-6221, 2002.
Bushman and Miller, *J. Virol.*, 71: 458-464, 1997.
Bushman, *Current Topics in Microbiology & Immunology*, 261: 165-77, 2002.
Bushman, *Proc. Natl. Acad. Sci. USA*, 91(20):9233-92337, 1994.
Bushman, *Science*, 267(5203):1443-1444, 1995.
Busschots et al., *J. Biol. Chem.*, 280:17841-7, 2005.
Cavazzana-Calvo et al., *Science*, 288: 669-72, 2000.
Chakravarti et al., *Handbook of Methods of Applied Statistics*. In: Handbook of Methods of Applied Statistics: John Wiley and Sons, 1967, p. 392-394.
Chen and Okayama, *Mol. Cell Biol.*, 7(8):2745-2752, 1987.
Cherepanov et al., *Nat. Struct. Mol. Biol.*, 12:526-32, 2005.

Ciuffi et al., *Nat. Med.*, 11: 1287-9, 2005.
Coffin et al., *Retroviruses*. Plainview: Cold Spring Harbor Press, 2000.
Coffin, In: *Virology*, Fields et al. (Eds.), Raven Press, NY, 1437-1500, 1990.
Coupar et al., *Gene*, 68:1-10, 1988.
Curran et al., *Mol. Ther.*, 1: 31-38, 2000.
DeGroot, *Probability and Statistics*. In: Probability and Statistics, edited by Wesley A-: Addision-Wesley, 1975, p. 483-486.
Dennis et al., *Genome Biol.*, 4: 3, 2003.
Derksen et al., *J Gene Med.*, 4: 463-469, 2002.
Donaldson et al., *Lancet.*, 344: 971-972, 1994.
Espanel and Sudol, *J. Biol. Chem.*, 276: 14514-23, 2001.
Friedmann, *Science*, 244:1275-1281, 1989.
Fye and Benham, *Phys E E*, 59: 3408-3426, 1999.
Gomez-Foix et al., *J. Biol. Chem.*, 267:25129-25134, 1992.
Gopal, *Mol. Cell Biol.*, 5:1188-1190, 1985.
Goulaouic and Chow, *J. Virol.*, 70(1):37-46, 1996.
Graham and Prevec, In: *Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al., *J. Gen. Virl.*, 36(1):59-74, 1977.
Grunhaus and Horwitz, *Seminar in Virology*, 3:237-252, 1992.
Hacein-Bey-Abina et al., *N. Engl. J. Med.*, 348: 255-256, 2003.
Hacein-Bey-Abina et al., *Science*, 302: 415-19, 2003.
Hahn and Weinberg, *Nat. Rev. Cancer*, 2: 331-341, 2002.
Haren et al., *Annu. Rev. Microbiol.*, 53:245-281 1999.
Hermonat and Muzycska, *Proc. Natl. Acad. Sci. USA*, 81:6466-6470, 1984.
Herz and Gerard, *Proc. Natl. Acad. Sci. USA*, 90:2812-2816, 1993.
Horwich et al., *Virol*, 64:642-650, 1990.
Hughes et al., *Mol. Ther.*, 5: 16-24, 2002.
Jamieson et al., *Nat. Rev. Drug Discov.*, 2: 361-68, 2003.
Joag et al., *Lentiviruses*. In: Fields B N, Knipe D M, Howley P M (eds.) Fields Virology. Lippincott-Raven Publishers, Philadelphia, pp. 1977-96, 1996.
Johnston et al., *J. Virol.*, 73: 4991-5000, 1999.
Jones and Shenk, *Cell*, 13:181-188, 1978.
Kang and Kim, *J. Biol. Chem.*, 275: 8742-48, 2000.
Kang et al., *J. Virol.*, 76: 9378-9388, 2002.
Karolchik et al., *Nucleic Acids Res.*, 31: 51-54, 2003.
Kent, *Genome Res.*, 12: 656-664, 2002.
Khan et al., *Nuc. Acids Res.*, 19: 851-60, 1990.
Kiem et al., *Mol. Ther.*, 9:389-395, 2004.
Komuro et al., *Nucleic Acid Research*, 27: 1957-65, 1999.
Kowalski et al., *Proc. Natl. Acad. Sci. USA*, 85: 9464-9468, 1988.
Kumar et al., *Hum. Gene Ther.*, 14: 67-77, 2003.
Kylkosky et al., *Virology*, 206: 448-56, 1995.
Le Gal La Salle et al., *Science*, 259:988-990, 1993.
Levrero et al., *Gene*, 101: 195-202, 1991.
Llano et al., *J. Virol.*, 78:9524-37, 2004.
Loewen et al., *Hum. Gene Ther.*, 12: 2109-2119, 2001.
Lotery et al., *Hum. Gene Ther.*, 13: 689-696, 2002.
Lutz, *Vet. Microbiol.*, 23: 131-146, 1990.
Mann et al., *Cell*, 33:153-159, 1983.
Matsuzaki et al., *J. Bact.*, 172: 610-618, 1990
Merrifield, *Science*, 232(4748):341-347, 1986.
Mitchell et al., *PLoS Biol* 2: E234, 2004.
Molteni et al., *Acta Crystallographica Section D-Biological Crystallography.* 57: 536-44, 2001.
Nabel et al., *Science*, 244(4910):1342-1344, 1989.
Nicolas and Rubinstein, In: *Vectors: A survey of molecular cloning vectors and their uses*, Rodriguez and Denhardt, eds., Stoneham: Butterworth, pp. 494-513, 1988.
Nicolau et al., *Methods Enzymol.*, 149:157-176, 1987.
Nowotny et al., *Lancet.*, 346: 252-253, 1995.
Olivares et al., *Nature Biotechnology*, 20: 1124-28, 2002.
Ortiz-Urda et al., *Nature Med* 8: 1166-70, 2002.
Paskind et al., *Virology*, 67:242-248, 1975.
PCT Appln. WO 96/06166
PCT Appln. WO 98/53057
PCT Appln. WO 98/53058
PCT Appln. WO 98/53060
Poeschla et al., *Nature Med.*, 4: 354-357, 1998.
Porteus and Carroll, *Nature Biotechnology*, 23(8):967-973, 2005.
Potaman et al, *J. Mol. Biol.*, 326: 1095-1111, 2003.
Potter et al., *Proc. Natl. Acad. Sci. USA*, 81:7161-7165, 1984.
Pruitt and Maglott, *Nucleic Acids Res.*, 29: 137-140, 2001.
Quackenbush et al., *Nucleic Acids Res.*, 29: 159-164, 2001.
Racher et al., *Biotechnology Techniques*, 9:169-174, 1995.
Ragot et al., *Nature*, 361:647-650, 1993.
Recinos et al., *Physiol Genomics*, 6: 6, 2004.
Rich et al., *Hum. Gene Ther.*, 4:461-476, 1993.
Ridgeway, In: *Vectors: A survey of molecular cloning vectors and their uses*, Stoneham: Butterworth, pp. 467-492, 1988.
Rippe, et al., *Mol. Cell Biol.*, 10:689-695, 1990.
Rosenfeld et al., *Science*, 252:431-434, 1991.
Rosenfeld, et al., *Cell*, 68:143-155, 1992.
Saenz et al., *J. Virol.*, 78: 2906-2920, 2004.
Sambrook et al., In: *Molecular cloning*, Cold Spring Harbor Laboratory Press, Cold Spring Harbor, N.Y., 2001.
Sandmeyer, *Proc. Natl. Acad. Sci.* USA, 100: 5586-88, 2003.
Schroder et al., *Cell*, 110: 521-529, 2002.
Schuler, *J. Mol. Med.*, 75: 694-698, 1997.
Sheridan et al., *J. Biol. Chem.*, 273: 21298-21308, 1998.
Shibagaki et al., *Virology*, 230: 1-10, 1997.
Sinn et al., *J Virol.*, 79(20):12818-27, 2005.
Stein et al., *Mol. Ther.*, 3: 850-856, 2001.
Sternberg and Hamilton, *J. Mol. Biol.*, 150: 467-486, 1981
Stewart and Young, In: *Solid Phase Peptide Synthesis*, 2d. ed., Pierce Chemical Co., 1984.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Tam et al., *J. Am. Chem. Soc.*, 105:6442, 1983.
Tan et al., *J. Virol.*, 78: 1301-13, 2004.
Temin, In: *Gene Transfer*, Kucherlapati (Ed.), NY, Plenum Press, 149-188, 1986.
Thompson et al., *Nucleic Acids Res.*, 31: 3580-3585, 2003.
Trono, *Science*, 300: 1670-1671, 2003.
Tur-Kaspa et al., *Mol. Cell Biol.*, 6:716-718, 1986.
Varmus, *Science*, 240: 1427-1435, 1988.
Vigdal et al., *J. Mol. Biol.*, 323: 441-452, 2002.
Wang et al., *J. Clin. Invest.*, 104: R49-R56, 1999.
Wilson et al., *Science*, 244:1344-1346, 1989.
WO 97/2003
Wong et al., *Gene*, 10:87-94, 1980.
Wright and Voytas, *Genetics*, 149:703-715, 1998.
Wu and Wu, *Biochemistry*, 27: 887-892, 1988.
Wu and Wu, *J. Biol. Chem.*, 262:4429-4432, 1987.
Wu et al., *Science*, 300: 1749-51, 2003.
Xie et al., *Molecular & Cellular Biology*, 21: 6606-14, 2001.
Zhu et al., *Proc. Natl. Acad. Sci. USA*, 100: 5891-95, 2003.
Zufferey et al., *J. Virol.*, 72: 9873-9880, 1998.

What is claimed is:

1. A retroviral integrase complex comprising:
   a) a recombinant retroviral integrase having a domain comprising a non-native protein binding site inserted in an exposed unstructured loop of said integrase; and
   b) a DNA binding protein comprising a DNA binding domain and a peptide binding domain that binds the non-native protein binding site of the recombinant integrase.

2. The complex of claim 1, wherein the retroviral integrase is a FIV integrase, a MLV integrase, or lentivirus integrase.

3. The complex of claim 2, wherein the retroviral integrase is a FIV integrase.

4. The complex of claim 3, wherein the FIV integrase comprises an amino acid modification of H14N, E170A, or both H14N and E170A.

5. The complex of claim 1, wherein the peptide binding domain is a WW binding domain.

6. The complex of claim 1, wherein the exposed unstructed loop corresponds to amino acids encoded by a viral central-polypurine tract region (cPPT).

7. The complex of claim 1, wherein the non-native protein binding site comprises a PY motif or a PGR motif.

8. The complex of claim 1, wherein the non-native protein binding site is at least 20 amino acid in length.

9. The complex of claim 1, wherein the non-native protein binding site is at least 15 amino acids in length.

10. The complex of claim 9, wherein the non-native protein binding site is at least 12 amino acids in length.

11. The complex of claim 10, wherein the non-native protein binding site is at least 10 amino acids in length.

12. The complex of claim 1, wherein the DNA binding domain is a designed zinc finger comprising at least 2 finger modules.

13. The complex of claim 12, wherein the zinc-finger domain is Zif268.

* * * * *

SEQUENCE LISTING

<160> NUMBER OF SEQ ID NOS: 27

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ccctcggcga atctcctggc ttgaa                                              25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
gcgtctgcta ctgcttccct attt                                               24

<210> SEQ ID NO 3
<211> LENGTH: 115
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Phe Leu Pro Glu Thr Thr Ser Leu Asp Asn Ala Leu Ser Leu Ala Val
 1               5                  10                  15

His Ser Leu Asn Phe Lys Arg Arg Gly Arg Ile Gly Met Ala Pro
            20                  25                  30

Tyr Glu Leu Leu Ala Gln Gln Glu Ser Leu Arg Ile Gln Asp Tyr Phe
        35                  40                  45

Ser Ala Ile Pro Gln Lys Leu Gln Ala Gln Trp Ile Tyr Tyr Lys Asp
    50                  55                  60

Gln Lys Asp Lys Lys Trp Lys Gly Pro Met Arg Val Glu Tyr Trp Gly
65                  70                  75                  80

Gln Gly Ser Val Leu Leu Lys Asp Glu Gly Lys Gly Tyr Phe Leu Ile
                85                  90                  95

Pro Arg Arg His Ile Arg Arg Val Pro Glu Pro Cys Ala Leu Pro Glu
            100                 105                 110

Gly Asp Glu
        115

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
tttaaaagaa gaggtaggat aggagggatg gcccccttatg aa                          42

```
<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Phe Lys Arg Arg Gly Arg Ile Gly Gly Met Ala Pro Tyr Glu
 1               5                  10

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tttaaaagaa gaggtaggtt accagggatg gcccttatg aa                          42

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Phe Lys Arg Arg Gly Arg Leu Pro Gly Met Ala Pro Tyr Glu
 1               5                  10

<210> SEQ ID NO 8
<211> LENGTH: 75
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
tttaaaagaa gaggtaggtt accacgactt ttacctccag gaccaccacc aggcagaggg      60 atggccccctt atgaa                                                     75

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Phe Lys Arg Lys Gly Arg Leu Pro Arg Leu Leu Pro Pro Gly Pro Pro
 1               5                  10                  15

Pro Gly Arg Gly Met Ala Pro Tyr Glu
            20                  25

<210> SEQ ID NO 10
<211> LENGTH: 78
<212> TYPE: DNA
<213> ORGANISM: Artificial Sequence
<220> FEATURE:
<223> OTHER INFORMATION: Description of Artificial Sequence: Synthetic
```

-continued

```
      Primer

<400> SEQUENCE: 10
tttaaaagaa gaggtaggtt accagagtac cctccatacc caccccacc ataccatct    60 gggatggccc cttatgaa                                                 78

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Phe Lys Arg Lys Gly Arg Leu Pro Glu Tyr Pro Pro Tyr Pro Pro Pro
 1               5                  10                  15

Pro Tyr Pro Ser Gly Met Ala Pro Tyr Glu
            20                  25

<210> SEQ ID NO 12
<211> LENGTH: 1082
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: CDS
<222> LOCATION: (190)..(987)

<400> SEQUENCE: 12
tgcctcctga gcgtagtcca gttactttca ggctcgggga gtgaaggcct cgttgagaga    60
aggtctcatt cggtgttttg ggaagagagt cgtgtgggcc caggtatcgt agcggcgaca   120
cgagagagac gggcggtgtg acagccttcc actacctgca cgagtgtatt ggtctgtctg   180 ctatcagct atg ccg ctg ccc gtt gcg ctg cag acc cgc ttg gcc aag aga   231
           Met Pro Leu Pro Val Ala Leu Gln Thr Arg Leu Ala Lys Arg
             1               5                  10 ggc atc ctc aaa cat ctg gag cct gaa cca gag gaa gag atc att gcc    279
Gly Ile Leu Lys His Leu Glu Pro Glu Pro Glu Glu Glu Ile Ile Ala
 15                  20                  25                  30 gag gac tat gac gat gat cct gtg gac tac gag gcc acc agg ttg gag    327
Glu Asp Tyr Asp Asp Asp Pro Val Asp Tyr Glu Ala Thr Arg Leu Glu
                 35                  40                  45 ggc cta cca cca agc tgg tac aag gtg ttc gac cct tcc tgc ggg ctc    375
Gly Leu Pro Pro Ser Trp Tyr Lys Val Phe Asp Pro Ser Cys Gly Leu
             50                  55                  60 cct tac tac tgg aat gca gac aca gac ctt gta tcc tgg ctc tcc cca    423
Pro Tyr Tyr Trp Asn Ala Asp Thr Asp Leu Val Ser Trp Leu Ser Pro
         65                  70                  75 cat gac ccc aac tcc gtg gtt acc aaa tcg gcc aag aag ctc aga agc    471
His Asp Pro Asn Ser Val Val Thr Lys Ser Ala Lys Lys Leu Arg Ser
     80                  85                  90 agt aat gca gat gct gaa gaa aag ttg gac cgg agc cat gac aag tcg    519
Ser Asn Ala Asp Ala Glu Glu Lys Leu Asp Arg Ser His Asp Lys Ser
 95                 100                 105                 110 gac agg ggc cat gac aag tcg gac cgc agc cat gag aaa cta gac agg    567
Asp Arg Gly His Asp Lys Ser Asp Arg Ser His Glu Lys Leu Asp Arg
                115                 120                 125 ggc cac gac aag tca gac cgg ggc cac gac aag tct gac agg gat cga    615
Gly His Asp Lys Ser Asp Arg Gly His Asp Lys Ser Asp Arg Asp Arg
```

```
                   130                 135                 140
gag cgt ggc tat gac aag gta gac aga gag aga gag cga gac agg gaa    663
Glu Arg Gly Tyr Asp Lys Val Asp Arg Glu Arg Glu Arg Asp Arg Glu
        145                 150                 155 cgg gat cgg gac cgc ggg tat gac aag gca gac cgg gaa gag ggc aaa    711
Arg Asp Arg Asp Arg Gly Tyr Asp Lys Ala Asp Arg Glu Glu Gly Lys
160                 165                 170 gaa cgg cgc cac cat cgc cgg gag gag ctg gct ccc tat ccc aag agc    759
Glu Arg Arg His His Arg Arg Glu Glu Leu Ala Pro Tyr Pro Lys Ser
175                 180                 185                 190 aag aag gca gta agc cga aag gat gaa gag tta gac ccc atg gac cct    807
Lys Lys Ala Val Ser Arg Lys Asp Glu Glu Leu Asp Pro Met Asp Pro
                195                 200                 205 agc tca tac tca gac gcc ccc cgg ggc acg tgg tca aca gga ctc ccc    855
Ser Ser Tyr Ser Asp Ala Pro Arg Gly Thr Trp Ser Thr Gly Leu Pro
            210                 215                 220 aag cgg aat gag gcc aag act ggc gct gac acc aca gca gct ggg ccc    903
Lys Arg Asn Glu Ala Lys Thr Gly Ala Asp Thr Thr Ala Ala Gly Pro
        225                 230                 235 ctc ttc cag cag cgg ccg tat cca tcc cca ggg gct gtg ctc cgg gcc    951
Leu Phe Gln Gln Arg Pro Tyr Pro Ser Pro Gly Ala Val Leu Arg Ala
    240                 245                 250 aat gca gag gcc tcc cga acc aag cag cag gat tga agcttcggcc         997
Asn Ala Glu Ala Ser Arg Thr Lys Gln Gln Asp
255                 260                 265 tccctggccc tgggttaaaa taaaagcttt ctggtgatcc tgcccaccaa aaaaaaaaa   1057 aaaaaaaaaa aaaaaaaaaa aaaaa                                        1082

<210> SEQ ID NO 13
<211> LENGTH: 265
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Met Pro Leu Pro Val Ala Leu Gln Thr Arg Leu Ala Lys Arg Gly Ile
1               5                   10                  15

Leu Lys His Leu Glu Pro Glu Pro Glu Glu Ile Ile Ala Glu Asp
            20                  25                  30

Tyr Asp Asp Asp Pro Val Asp Tyr Glu Ala Thr Arg Leu Glu Gly Leu
        35                  40                  45

Pro Pro Ser Trp Tyr Lys Val Phe Asp Pro Ser Cys Gly Leu Pro Tyr
    50                  55                  60

Tyr Trp Asn Ala Asp Thr Asp Leu Val Ser Trp Leu Ser Pro His Asp
65                  70                  75                  80

Pro Asn Ser Val Val Thr Lys Ser Ala Lys Leu Arg Ser Ser Asn
                85                  90                  95

Ala Asp Ala Glu Glu Lys Leu Asp Arg Ser His Asp Lys Ser Asp Arg
            100                 105                 110

Gly His Asp Lys Ser Asp Arg Ser His Glu Lys Leu Asp Arg Gly His
        115                 120                 125

Asp Lys Ser Asp Arg Gly His Asp Lys Ser Asp Arg Asp Arg Glu Arg
    130                 135                 140

Gly Tyr Asp Lys Val Asp Arg Glu Arg Glu Arg Asp Arg Glu Arg Asp
145                 150                 155                 160
```

```
            Arg Asp Arg Gly Tyr Asp Lys Ala Asp Arg Glu Glu Gly Lys Glu Arg
                        165                 170                 175

Arg His His Arg Arg Glu Glu Leu Ala Pro Tyr Pro Lys Ser Lys Lys
                        180                 185                 190

Ala Val Ser Arg Lys Asp Glu Glu Leu Asp Pro Met Asp Pro Ser Ser
                        195                 200                 205

Tyr Ser Asp Ala Pro Arg Gly Thr Trp Ser Thr Gly Leu Pro Lys Arg
                        210                 215                 220

Asn Glu Ala Lys Thr Gly Ala Asp Thr Thr Ala Ala Gly Pro Leu Phe
            225                 230                 235                 240

Gln Gln Arg Pro Tyr Pro Ser Pro Gly Ala Val Leu Arg Ala Asn Ala
                        245                 250                 255

Glu Ala Ser Arg Thr Lys Gln Gln Asp
                        260                 265

<210> SEQ ID NO 14
<211> LENGTH: 1805
<212> TYPE: DNA
<213> ORGANISM: Homo sapiens
<220> FEATURE:
<221> NAME/KEY: CDS
<222> LOCATION: (114)..(998)

<400> SEQUENCE: 14
caaatgcaga agtggttctc atctttttt gcagcttaag atctgccttg gtatttgaag       60
agatataaac tagatcaatt tctttcacag gatcaactaa acagtgtacc aca atg        116
                                                           Met
                                                             1 aat tct gaa ctt gac tat tat gaa aag ttt gaa gaa gtc cat ggg att       164
Asn Ser Glu Leu Asp Tyr Tyr Glu Lys Phe Glu Glu Val His Gly Ile
         5                  10                  15 cta atg tat aaa gat ttt gtc aaa tat tgg gat aat gtg gaa gcg ttc       212
Leu Met Tyr Lys Asp Phe Val Lys Tyr Trp Asp Asn Val Glu Ala Phe
     20                  25                  30 cag gca aga cca gat gat ctt gtc att gcc acc tac cct aaa tct ggt       260
Gln Ala Arg Pro Asp Asp Leu Val Ile Ala Thr Tyr Pro Lys Ser Gly
 35                  40                  45 aca acc tgg gtt agt gaa att gtg tat atg atc tat aaa gag ggt gat       308
Thr Thr Trp Val Ser Glu Ile Val Tyr Met Ile Tyr Lys Glu Gly Asp
 50                  55                  60                  65 gtg gaa aag tgc aaa gaa gat gta att ttt aat cga ata cct ttc ctg       356
Val Glu Lys Cys Lys Glu Asp Val Ile Phe Asn Arg Ile Pro Phe Leu
                 70                  75                  80 gaa tgc aga aaa gaa aac ctc atg aat gga gta aaa caa tta gat gag       404
Glu Cys Arg Lys Glu Asn Leu Met Asn Gly Val Lys Gln Leu Asp Glu
             85                  90                  95 atg aat tct cct aga att gtg aag act cat ttg cca cct gaa ctt ctt       452
Met Asn Ser Pro Arg Ile Val Lys Thr His Leu Pro Pro Glu Leu Leu
         100                 105                 110 cct gcc tca ttt tgg gaa aag gat tgt aag ata atc tat ctt tgc cgg       500
Pro Ala Ser Phe Trp Glu Lys Asp Cys Lys Ile Ile Tyr Leu Cys Arg
     115                 120                 125 aat gca aag gat gtg gct gtt tcc ttt tat tat ttc ttt cta atg gtg       548
Asn Ala Lys Asp Val Ala Val Ser Phe Tyr Tyr Phe Phe Leu Met Val
 130                 135                 140                 145 gct ggt cat cca aat cct gga tcc ttt cca gag ttt gtg gag aaa ttc       596
Ala Gly His Pro Asn Pro Gly Ser Phe Pro Glu Phe Val Glu Lys Phe
                 150                 155                 160 atg caa gga cag gtt cct tat ggt tcc tgg tat aaa cat gta aaa tct       644
```

```
            Met Gln Gly Gln Val Pro Tyr Gly Ser Trp Tyr Lys His Val Lys Ser
                            165                 170                 175 tgg tgg gaa aag gga aag agt cca cgt gta cta ttt ctt ttc tac gaa          692
Trp Trp Glu Lys Gly Lys Ser Pro Arg Val Leu Phe Leu Phe Tyr Glu
            180                 185                 190 gac ctg aaa gag gat atc aga aaa gag gtg ata aaa ttg ata cat ttc          740
Asp Leu Lys Glu Asp Ile Arg Lys Glu Val Ile Lys Leu Ile His Phe
        195                 200                 205 ctg gaa agg aag cca tca gag gag ctt gtg gac agg att ata cat cat          788
Leu Glu Arg Lys Pro Ser Glu Glu Leu Val Asp Arg Ile Ile His His
210                 215                 220                 225 act tcg ttc caa gag atg aag aac aat cca tcc aca aat tac aca aca          836
Thr Ser Phe Gln Glu Met Lys Asn Asn Pro Ser Thr Asn Tyr Thr Thr
                230                 235                 240 ctg cca gac gaa att atg aac cag aaa ttg tcg ccc ttc atg aga aag          884
Leu Pro Asp Glu Ile Met Asn Gln Lys Leu Ser Pro Phe Met Arg Lys
            245                 250                 255 gga att aca gga gac tgg aaa aat cac ttt aca gta gcc ctg aat gaa          932
Gly Ile Thr Gly Asp Trp Lys Asn His Phe Thr Val Ala Leu Asn Glu
        260                 265                 270 aaa ttt gat aaa cat tat gag cag caa atg aag gaa tct aca ctg aag          980
Lys Phe Asp Lys His Tyr Glu Gln Gln Met Lys Glu Ser Thr Leu Lys
275                 280                 285 ttt cga act gag atc taa gaaggtcttt ctttacttaa catatctgat                 1028
Phe Arg Thr Glu Ile
290 attaaagatt tcttttcatt attctccact ttttcttatt ttagattgct agaaaagaca       1088 taatcatgga ttatgttgac attttctttt taaattttg tttaactttt ttttttttt         1148 tttgagacag agtctcactc tgttgcctag gctggaggac agtggcacaa tcatggctga       1208 ttgcagcctt gacctccttg actcaattga tcctcccatc tcagcctccc aagtagctag       1268 gactacagac atgtgcaacc atgtttggct aatttttta atgttttttt gtagagatga       1328 ggtcttatta tattgtccag gctggtcttg aattcctggg ctcaagcttc ccaagtagct       1388 gcaacaacag gcacacacca ccatgctcaa ctaattttat ttctattttt tgtatagaca       1448 ggggcttgct atagtgtcca ggctggtctg aaacccttga gctcaagtga tcttcccaca       1508 ccagcctccc aaaatactgg gattacaggc ttgagcctcc atgcctggcc caggtaacat       1568 gtttattgag ctgtacatgc atatgagaaa taagaaactt ttttttccta ctatcatctc       1628 ttaaattttg ttttcttttt cttttgcttc ctcttcttct tttctatttt ttataaatat       1688 catgcacaac tataacctat gggaatgatg tagtaacaca gattattcat cttgttagag       1748 ttgtattaaa aataaacaag catttcaaat taaaaaaaaa aaaaaaaaaa aaaaaaa         1805

<210> SEQ ID NO 15
<211> LENGTH: 294
<212> TYPE: PRT
<213> ORGANISM: Homo sapiens

<400> SEQUENCE: 15

Met Asn Ser Glu Leu Asp Tyr Tyr Glu Lys Phe Glu Glu Val His Gly
 1               5                  10                  15

Ile Leu Met Tyr Lys Asp Phe Val Lys Tyr Trp Asp Asn Val Glu Ala
            20                  25                  30

Phe Gln Ala Arg Pro Asp Asp Leu Val Ile Ala Thr Tyr Pro Lys Ser
        35                  40                  45

Gly Thr Thr Trp Val Ser Glu Ile Val Tyr Met Ile Tyr Lys Glu Gly
```

```
                50                   55                   60
Asp Val Glu Lys Cys Lys Glu Asp Val Ile Phe Asn Arg Ile Pro Phe
 65                   70                   75                   80

Leu Glu Cys Arg Lys Glu Asn Leu Met Asn Gly Val Lys Gln Leu Asp
                 85                   90                   95

Glu Met Asn Ser Pro Arg Ile Val Lys Thr His Leu Pro Pro Glu Leu
            100                  105                  110

Leu Pro Ala Ser Phe Trp Lys Asp Cys Lys Ile Ile Tyr Leu Cys
        115                  120                  125

Arg Asn Ala Lys Asp Val Ala Val Ser Phe Tyr Tyr Phe Leu Met
130                  135                  140

Val Ala Gly His Pro Asn Pro Gly Ser Phe Pro Glu Phe Val Glu Lys
145                  150                  155                  160

Phe Met Gln Gly Gln Val Pro Tyr Gly Ser Trp Tyr Lys His Val Lys
                 165                  170                  175

Ser Trp Trp Glu Lys Gly Lys Ser Pro Arg Val Leu Phe Leu Phe Tyr
            180                  185                  190

Glu Asp Leu Lys Glu Asp Ile Arg Lys Glu Val Ile Lys Leu Ile His
        195                  200                  205

Phe Leu Glu Arg Lys Pro Ser Glu Glu Leu Val Asp Arg Ile Ile His
    210                  215                  220

His Thr Ser Phe Gln Glu Met Lys Asn Asn Pro Ser Thr Asn Tyr Thr
225                  230                  235                  240

Thr Leu Pro Asp Glu Ile Met Asn Gln Lys Leu Ser Pro Phe Met Arg
                 245                  250                  255

Lys Gly Ile Thr Gly Asp Trp Lys Asn His Phe Thr Val Ala Leu Asn
            260                  265                  270

Glu Lys Phe Asp Lys His Tyr Glu Gln Gln Met Lys Glu Ser Thr Leu
        275                  280                  285

Lys Phe Arg Thr Glu Ile
    290

<210> SEQ ID NO 16
<211> LENGTH: 4496
<212> TYPE: DNA
<213> ORGANISM: Homo sapiens
<220> FEATURE:
<221> NAME/KEY: CDS
<222> LOCATION: (272)..(3655)

<400> SEQUENCE: 16
gggagccccg accgtcacga gcgtcgaaga gacaaagccg cgtcaggggg cccggccggg      60 gcggggagc ccggggcttg ttggtgcccc agcccgcgcg gagggcccct cggaccccgcg     120 cgccgccgct gccgccgccg ccgcctcgca acaggtccgg gcggcctcgc tctccgctcc    180 cctccccgc atccgcgacc ctccggggca cctcagctcg gccggggccg cagtctggcc    240
acccgcttcc atgcggttcg ggtccaagat g atg ccg atg ttt ctt acc gtg       292
                                   Met Pro Met Phe Leu Thr Val
                                     1               5 tat ctc agt aac aat gag cag cac ttc aca gaa gtt cca gtt act cca     340
Tyr Leu Ser Asn Asn Glu Gln His Phe Thr Glu Val Pro Val Thr Pro
         10                  15                  20 gaa aca ata tgc aga gac gtg gtg gat ctg tgc aaa gaa ccc ggc gag     388
Glu Thr Ile Cys Arg Asp Val Val Asp Leu Cys Lys Glu Pro Gly Glu
     25                  30                  35 agt gat tgc cat ttg gct gaa gtg tgg tgt ggc tct gaa cgt cca gtt     436
```

```
                Ser Asp Cys His Leu Ala Glu Val Trp Cys Gly Ser Glu Arg Pro Val
                40              45                  50                  55 gcg gat aat gag cga atg ttt gat gtt ctt caa cga ttt gga agt cag        484
Ala Asp Asn Glu Arg Met Phe Asp Val Leu Gln Arg Phe Gly Ser Gln
                60                  65                  70 agg aac gaa gtt cgc ttc ttc ctt cgt cat gaa cgc ccc cct ggc agg        532
Arg Asn Glu Val Arg Phe Phe Leu Arg His Glu Arg Pro Pro Gly Arg
                    75                  80                  85 gac att gtg agt gga cca aga tct cag gat cca agt tta aaa aga aat        580
Asp Ile Val Ser Gly Pro Arg Ser Gln Asp Pro Ser Leu Lys Arg Asn
                90                  95                  100 ggt gta aaa gtt cct ggt gaa tat cga aga aag gag aac ggt gtt aat        628
Gly Val Lys Val Pro Gly Glu Tyr Arg Arg Lys Glu Asn Gly Val Asn
    105                 110                 115 agt cct agg atg gat ctg act ctt gct gaa ctt cag gaa atg gca tct        676
Ser Pro Arg Met Asp Leu Thr Leu Ala Glu Leu Gln Glu Met Ala Ser
120                 125                 130                 135 cgc cag cag caa cag att gaa gcc cag caa caa ttg ctg gca act aag        724
Arg Gln Gln Gln Gln Ile Glu Ala Gln Gln Gln Leu Leu Ala Thr Lys
                    140                 145                 150 gaa cag cgc tta aag ttt ttg aaa caa caa gat cag cga caa cag caa        772
Glu Gln Arg Leu Lys Phe Leu Lys Gln Gln Asp Gln Arg Gln Gln Gln
                155                 160                 165 caa gtt gct gag cag gag aaa ctt aaa agg cta aaa gaa ata gct gag        820
Gln Val Ala Glu Gln Glu Lys Leu Lys Arg Leu Lys Glu Ile Ala Glu
            170                 175                 180 aat cag gaa gct aag cta aaa aaa gtg aga gca ctt aaa ggc cac gtg        868
Asn Gln Glu Ala Lys Leu Lys Lys Val Arg Ala Leu Lys Gly His Val
185                 190                 195 gaa cag aag aga cta agc aat ggg aaa ctt gtg gag gaa att gaa cag        916
Glu Gln Lys Arg Leu Ser Asn Gly Lys Leu Val Glu Glu Ile Glu Gln
200                 205                 210                 215 atg aat aat ttg ttc cag caa aaa cag agg gag ctc gtc ctg gct gtg        964
Met Asn Asn Leu Phe Gln Gln Lys Gln Arg Glu Leu Val Leu Ala Val
                    220                 225                 230 tca aaa gta gaa gaa ctg acc agg cag cta gag atg ctc aag aac ggc       1012
Ser Lys Val Glu Glu Leu Thr Arg Gln Leu Glu Met Leu Lys Asn Gly
                235                 240                 245 agg atc gac agc cac cat gac aat cag tct gca gtg gct gag ctt gat       1060
Arg Ile Asp Ser His His Asp Asn Gln Ser Ala Val Ala Glu Leu Asp
            250                 255                 260 cgc ctc tat aag gag ctg cag cta aga aac aaa ttg aat caa gag cag       1108
Arg Leu Tyr Lys Glu Leu Gln Leu Arg Asn Lys Leu Asn Gln Glu Gln
265                 270                 275 aat gcc aag cta caa caa cag agg gag tgt ttg aat aag cgt aat tca       1156
Asn Ala Lys Leu Gln Gln Gln Arg Glu Cys Leu Asn Lys Arg Asn Ser
280                 285                 290                 295 gaa gtg gca gtc atg gat aag cgt gtt aat gag ctg agg gac cgg ctg       1204
Glu Val Ala Val Met Asp Lys Arg Val Asn Glu Leu Arg Asp Arg Leu
                    300                 305                 310 tgg aag aag aag gca gct cta cag caa aaa gaa aat cta cca gtt tca       1252
Trp Lys Lys Lys Ala Ala Leu Gln Gln Lys Glu Asn Leu Pro Val Ser
                315                 320                 325 tct gat gga aat ctt ccc cag caa gcc gcg tca gcc cca agc cgt gtg       1300
Ser Asp Gly Asn Leu Pro Gln Gln Ala Ala Ser Ala Pro Ser Arg Val
            330                 335                 340 gct gca gta ggt ccc tat atc cag tcg tct act atg cct cgg atg ccc       1348
Ala Ala Val Gly Pro Tyr Ile Gln Ser Ser Thr Met Pro Arg Met Pro
345                 350                 355
```

```
tca agg cct gaa ttg ctg gtg aag cca gcc ctg ccg gat ggt tcc ttg    1396
Ser Arg Pro Glu Leu Leu Val Lys Pro Ala Leu Pro Asp Gly Ser Leu
360             365                 370                 375 gtc att cag gct tca gag ggg ccg atg aaa ata cag aca ctg ccc aac    1444
Val Ile Gln Ala Ser Glu Gly Pro Met Lys Ile Gln Thr Leu Pro Asn
                380                 385                 390 atg aga tct ggg gct gct tca caa act aaa ggc tct aaa atc cat cca    1492
Met Arg Ser Gly Ala Ala Ser Gln Thr Lys Gly Ser Lys Ile His Pro
            395                 400                 405 gtt ggc cct gat tgg agt cct tca aat gca gat ctt ttc cca agc caa    1540
Val Gly Pro Asp Trp Ser Pro Ser Asn Ala Asp Leu Phe Pro Ser Gln
        410                 415                 420 ggc tct gct tct gta cct caa agc act ggg aat gct ctg gat caa gtt    1588
Gly Ser Ala Ser Val Pro Gln Ser Thr Gly Asn Ala Leu Asp Gln Val
    425                 430                 435 gat gat gga gag gtt ccg ctg agg gag aaa gag aag aaa gtg cgt ccg    1636
Asp Asp Gly Glu Val Pro Leu Arg Glu Lys Glu Lys Lys Val Arg Pro
440                 445                 450                 455 ttc tca atg ttt gat gca gta gac cag tcc aat gcc cca cct tcc ttt    1684
Phe Ser Met Phe Asp Ala Val Asp Gln Ser Asn Ala Pro Pro Ser Phe
                460                 465                 470 ggt act ctg agg aag aac cag agc agt gaa gat atc ttg cgg gat gct    1732
Gly Thr Leu Arg Lys Asn Gln Ser Ser Glu Asp Ile Leu Arg Asp Ala
            475                 480                 485 cag gtt gca aat aaa aat gtg gct aaa gta cca cct cct gtt cct aca    1780
Gln Val Ala Asn Lys Asn Val Ala Lys Val Pro Pro Pro Val Pro Thr
        490                 495                 500 aaa cca aaa cag att aat ttg cct tat ttt gga caa act aat cag cca    1828
Lys Pro Lys Gln Ile Asn Leu Pro Tyr Phe Gly Gln Thr Asn Gln Pro
    505                 510                 515 cct tca gac att aag cca gac gga agt tct cag cag ttg tca aca gtt    1876
Pro Ser Asp Ile Lys Pro Asp Gly Ser Ser Gln Gln Leu Ser Thr Val
520                 525                 530                 535 gtt ccg tcc atg gga act aaa cca aaa cca gca ggg cag cag ccg aga    1924
Val Pro Ser Met Gly Thr Lys Pro Lys Pro Ala Gly Gln Gln Pro Arg
                540                 545                 550 gtg ctg cta tct ccc agc ata cct tcg gtt ggc caa gac cag acc ctt    1972
Val Leu Leu Ser Pro Ser Ile Pro Ser Val Gly Gln Asp Gln Thr Leu
            555                 560                 565 tct cca ggt tct aag caa gaa agt cca cct gct gct gcc gtc cgg ccc    2020
Ser Pro Gly Ser Lys Gln Glu Ser Pro Pro Ala Ala Ala Val Arg Pro
        570                 575                 580 ttt act ccc cag cct tcc aaa gac acc tta ctt cca ccc ttc aga aaa    2068
Phe Thr Pro Gln Pro Ser Lys Asp Thr Leu Leu Pro Pro Phe Arg Lys
    585                 590                 595 ccc cag acc gtg gca gca agt tca ata tat tcc atg tat acg caa cag    2116
Pro Gln Thr Val Ala Ala Ser Ser Ile Tyr Ser Met Tyr Thr Gln Gln
600                 605                 610                 615 cag gcg cca gga aaa aac ttc cag cag gct gtg cag agc gcg ttg acc    2164
Gln Ala Pro Gly Lys Asn Phe Gln Gln Ala Val Gln Ser Ala Leu Thr
                620                 625                 630 aag act cat acc aga ggg cca cac ttt tca agt gta tat ggt aag cct    2212
Lys Thr His Thr Arg Gly Pro His Phe Ser Ser Val Tyr Gly Lys Pro
            635                 640                 645 gta att gct gct gcc cag aat caa cag cag cac cca gag aac att tat    2260
Val Ile Ala Ala Ala Gln Asn Gln Gln Gln His Pro Glu Asn Ile Tyr
        650                 655                 660 tcc aat agc cag ggc aag cct ggc agt cca gaa cct gaa aca gag cct    2308
Ser Asn Ser Gln Gly Lys Pro Gly Ser Pro Glu Pro Glu Thr Glu Pro
    665                 670                 675
```

```
gtt tct tca gtt cag gag aac cat gaa aac gaa aga att cct cgg cca    2356
Val Ser Ser Val Gln Glu Asn His Glu Asn Glu Arg Ile Pro Arg Pro
680             685                 690                 695 ctc agc cca act aaa tta ctg cct ttc tta tct aat cct tac cga aac    2404
Leu Ser Pro Thr Lys Leu Leu Pro Phe Leu Ser Asn Pro Tyr Arg Asn
            700                 705                 710 cag agt gat gct gac cta gaa gcc tta cga aag aaa ctg tct aac gca    2452
Gln Ser Asp Ala Asp Leu Glu Ala Leu Arg Lys Lys Leu Ser Asn Ala
        715                 720                 725 cca agg cct cta aag aaa cgt agt tct att aca gag cca gag ggt cct    2500
Pro Arg Pro Leu Lys Lys Arg Ser Ser Ile Thr Glu Pro Glu Gly Pro
    730                 735                 740 aat ggg cca aat att cag aag ctt tta tat cag agg acc acc ata gcg    2548
Asn Gly Pro Asn Ile Gln Lys Leu Leu Tyr Gln Arg Thr Thr Ile Ala
745                 750                 755 gcc atg gag acc atc tct gtc cca tca tac cca tcc aag tca gct tct    2596
Ala Met Glu Thr Ile Ser Val Pro Ser Tyr Pro Ser Lys Ser Ala Ser
760                 765                 770                 775 gtg act gcc agc tca gaa agc cca gta gaa atc cag aat cca tat tta    2644
Val Thr Ala Ser Ser Glu Ser Pro Val Glu Ile Gln Asn Pro Tyr Leu
            780                 785                 790 cat gtg gag ccc gaa aag gag gtg gtc tct ctg gtt cct gaa tca ttg    2692
His Val Glu Pro Glu Lys Glu Val Val Ser Leu Val Pro Glu Ser Leu
        795                 800                 805 tcc cca gag gat gtg ggg aat gcc agt aca gag aac agt gac atg cca    2740
Ser Pro Glu Asp Val Gly Asn Ala Ser Thr Glu Asn Ser Asp Met Pro
    810                 815                 820 gct cct tct cca ggc ctt gat tat gag cct gag gga gtc cca gac aac    2788
Ala Pro Ser Pro Gly Leu Asp Tyr Glu Pro Glu Gly Val Pro Asp Asn
825                 830                 835 agc cca aat ctc cag aat aac cca gaa gaa cca aat cca gag gct cca    2836
Ser Pro Asn Leu Gln Asn Asn Pro Glu Glu Pro Asn Pro Glu Ala Pro
840                 845                 850                 855 cat gtg ctt gat gtg tac ctg gag gag tac cct cca tac cca ccc cca    2884
His Val Leu Asp Val Tyr Leu Glu Glu Tyr Pro Pro Tyr Pro Pro Pro
            860                 865                 870 cca tac cca tct ggg gag cct gaa ggg ccc gga gaa gac tcg gtg agc    2932
Pro Tyr Pro Ser Gly Glu Pro Glu Gly Pro Gly Glu Asp Ser Val Ser
        875                 880                 885 atg cgc ccg cct gaa atc acc ggg cag gtc tct ctg cct cct ggt aaa    2980
Met Arg Pro Pro Glu Ile Thr Gly Gln Val Ser Leu Pro Pro Gly Lys
    890                 895                 900 agg aca aac ttg cgt aaa act ggc tca gag cgt atc gct cat gga atg    3028
Arg Thr Asn Leu Arg Lys Thr Gly Ser Glu Arg Ile Ala His Gly Met
905                 910                 915 agg gtg aaa ttc aac ccc ctt gct tta ctg cta gat tcg tct ttg gag    3076
Arg Val Lys Phe Asn Pro Leu Ala Leu Leu Leu Asp Ser Ser Leu Glu
920                 925                 930                 935 gga gaa ttt gac ctt gta cag aga att att tat gag gtt gat gac cca    3124
Gly Glu Phe Asp Leu Val Gln Arg Ile Ile Tyr Glu Val Asp Asp Pro
            940                 945                 950 agc ctc ccc aat gat gaa ggc atc acg gct ctt cac aat gct gtg tgt    3172
Ser Leu Pro Asn Asp Glu Gly Ile Thr Ala Leu His Asn Ala Val Cys
        955                 960                 965 gca ggc cac aca gaa atc gtt aag ttc ctg gta cag ttt ggt gta aat    3220
Ala Gly His Thr Glu Ile Val Lys Phe Leu Val Gln Phe Gly Val Asn
    970                 975                 980 gta aat gct gct gat agt gat gga tgg act cca tta cat tgt gct gcc    3268
Val Asn Ala Ala Asp Ser Asp Gly Trp Thr Pro Leu His Cys Ala Ala
```

-continued

```
                        985                 990                 995
tca tgt aac aac gtc caa gtg tgt aag ttt ttg gtg gag tca gga gcc      3316
Ser Cys Asn Asn Val Gln Val Cys Lys Phe Leu Val Glu Ser Gly Ala
1000                1005                1010                1015 gct gtg ttt gcc atg acc tac agt gac atg cag act gct gca gat aag      3364
Ala Val Phe Ala Met Thr Tyr Ser Asp Met Gln Thr Ala Ala Asp Lys
            1020                1025                1030 tgc gag gaa atg gag gaa ggc tac act cag tgc tcc caa ttt ctt tat      3412
Cys Glu Glu Met Glu Glu Gly Tyr Thr Gln Cys Ser Gln Phe Leu Tyr
        1035                1040                1045 gga gtt cag gag aag atg ggc ata atg aat aaa gga gtc att tat gcg      3460
Gly Val Gln Glu Lys Met Gly Ile Met Asn Lys Gly Val Ile Tyr Ala
    1050                1055                1060 ctt tgg gat tat gaa cct cag aat gat gat gag ctg ccc atg aaa gaa      3508
Leu Trp Asp Tyr Glu Pro Gln Asn Asp Asp Glu Leu Pro Met Lys Glu
1065                1070                1075 gga gac tgc atg aca atc atc cac agg gaa gac gaa gat gaa atc gaa      3556
Gly Asp Cys Met Thr Ile Ile His Arg Glu Asp Glu Asp Glu Ile Glu
1080                1085                1090                1095 tgg tgg tgg gcg cgc ctt aat gat aag gag gga tat gtt cca cgt aac      3604
Trp Trp Trp Ala Arg Leu Asn Asp Lys Glu Gly Tyr Val Pro Arg Asn
            1100                1105                1110 ttg ctg gga ctg tac cca aga att aaa cca aga caa agg agc ttg gcc      3652
Leu Leu Gly Leu Tyr Pro Arg Ile Lys Pro Arg Gln Arg Ser Leu Ala
        1115                1120                1125 tga aacttccaca cagaattttta gtcaatgaag aattaatctc tgttaagaag           3705
aagtaatacg attattttttg gcaaaaattt cacaagactt attttaatga caatgtagct    3765
tgaaagcgat gaagaatgtc tctagaagag aatgaaggat tgaagaattc accattagag    3825
gacatttagc gtgatgaaat aaagcatcta cgtcagcagg ccatactgtg ttggggcaaa    3885
ggtgtcccgt gtagcactca gataagtata cagcgacaat cctgttttct acaagaatcc    3945
tgtctagtaa ataggatcat ttattgggca gttgggaaat cagctctctg tcctgttgag    4005
tgttttcagc agctgctcct aaaccagtcc tcctgccaga aaggaccagt gccgtcacat    4065
cgctgtctct gattgtcccc ggcaccagca ggcccttggg gggctcacct gaaggctcga    4125
aggcactgca cacttgtata ttgtcagtga agaactgtta gttggttgtc agtgaacaat    4185
aactttatta tatgagtttt tgtagcatct taagaattat acatatgttt gaaatattga    4245
aactaagcta cggtaccagt aattagatgt agaatcttgt ttgtaggctg aattttaatc    4305
tgtatttatt gtcttttgta tctcagaaat tagaaacttg ctacagactt acccgtaata    4365
tttgtcaaga tcatagctga ctttaaaaac agttgtaata aacttttttga tgctaaaaaa    4425 aaaaaaaaaa aaaaaaaaaa aaaaaaaaaa aaaaaaaaaa aaaaaaaaaa aaaaaaaaaa    4485
aaaaaaaaaa a                                                         4496
```

<210> SEQ ID NO 17
<211> LENGTH: 1127
<212> TYPE: PRT
<213> ORGANISM: Homo sapiens

<400> SEQUENCE: 17

```
Met Pro Met Phe Leu Thr Val Tyr Leu Ser Asn Asn Glu Gln His Phe
 1               5                  10                  15

Thr Glu Val Pro Val Thr Pro Glu Thr Ile Cys Arg Asp Val Val Asp
            20                  25                  30

Leu Cys Lys Glu Pro Gly Glu Ser Asp Cys His Leu Ala Glu Val Trp
```

-continued

```
                35                  40                  45
Cys Gly Ser Glu Arg Pro Val Ala Asp Asn Glu Arg Met Phe Asp Val
 50                  55                  60
Leu Gln Arg Phe Gly Ser Gln Arg Asn Glu Val Arg Phe Phe Leu Arg
 65                  70                  75                  80
His Glu Arg Pro Pro Gly Arg Asp Ile Val Ser Gly Pro Arg Ser Gln
                 85                  90                  95
Asp Pro Ser Leu Lys Arg Asn Gly Val Lys Val Pro Gly Glu Tyr Arg
                100                 105                 110
Arg Lys Glu Asn Gly Val Asn Ser Pro Arg Met Asp Leu Thr Leu Ala
                115                 120                 125
Glu Leu Gln Glu Met Ala Ser Arg Gln Gln Gln Ile Glu Ala Gln
130                 135                 140
Gln Gln Leu Leu Ala Thr Lys Glu Gln Arg Leu Lys Phe Leu Lys Gln
145                 150                 155                 160
Gln Asp Gln Arg Gln Gln Gln Val Ala Glu Gln Glu Lys Leu Lys
                165                 170                 175
Arg Leu Lys Glu Ile Ala Glu Asn Gln Glu Ala Lys Leu Lys Lys Val
                180                 185                 190
Arg Ala Leu Lys Gly His Val Glu Gln Lys Arg Leu Ser Asn Gly Lys
                195                 200                 205
Leu Val Glu Glu Ile Glu Gln Met Asn Asn Leu Phe Gln Gln Lys Gln
                210                 215                 220
Arg Glu Leu Val Leu Ala Val Ser Lys Val Glu Glu Leu Thr Arg Gln
225                 230                 235                 240
Leu Glu Met Leu Lys Asn Gly Arg Ile Asp Ser His His Asp Asn Gln
                245                 250                 255
Ser Ala Val Ala Glu Leu Asp Arg Leu Tyr Lys Glu Leu Gln Leu Arg
                260                 265                 270
Asn Lys Leu Asn Gln Glu Gln Asn Ala Lys Leu Gln Gln Arg Glu
                275                 280                 285
Cys Leu Asn Lys Arg Asn Ser Glu Val Ala Val Met Asp Lys Arg Val
290                 295                 300
Asn Glu Leu Arg Asp Arg Leu Trp Lys Lys Ala Ala Leu Gln Gln
305                 310                 315                 320
Lys Glu Asn Leu Pro Val Ser Asp Gly Asn Leu Pro Gln Gln Ala
                325                 330                 335
Ala Ser Ala Pro Ser Arg Val Ala Val Gly Pro Tyr Ile Gln Ser
                340                 345                 350
Ser Thr Met Pro Arg Met Pro Ser Arg Pro Glu Leu Leu Val Lys Pro
                355                 360                 365
Ala Leu Pro Asp Gly Ser Leu Val Ile Gln Ala Ser Glu Gly Pro Met
                370                 375                 380
Lys Ile Gln Thr Leu Pro Asn Met Arg Ser Gly Ala Ala Ser Gln Thr
385                 390                 395                 400
Lys Gly Ser Lys Ile His Pro Val Gly Pro Asp Trp Ser Pro Ser Asn
                405                 410                 415
Ala Asp Leu Phe Pro Ser Gln Gly Ser Ala Ser Val Pro Gln Ser Thr
                420                 425                 430
Gly Asn Ala Leu Asp Gln Val Asp Asp Gly Glu Val Pro Leu Arg Glu
                435                 440                 445
Lys Glu Lys Lys Val Arg Pro Phe Ser Met Phe Asp Ala Val Asp Gln
450                 455                 460
```

-continued

```
Ser Asn Ala Pro Pro Ser Phe Gly Thr Leu Arg Lys Asn Gln Ser Ser
465                 470                 475                 480

Glu Asp Ile Leu Arg Asp Ala Gln Val Ala Asn Lys Asn Val Ala Lys
            485                 490                 495

Val Pro Pro Val Pro Thr Lys Pro Lys Gln Ile Asn Leu Pro Tyr
        500                 505                 510

Phe Gly Gln Thr Asn Gln Pro Ser Asp Ile Lys Pro Asp Gly Ser
        515                 520                 525

Ser Gln Gln Leu Ser Thr Val Val Pro Ser Met Gly Thr Lys Pro Lys
530                 535                 540

Pro Ala Gly Gln Gln Pro Arg Val Leu Leu Ser Pro Ser Ile Pro Ser
545                 550                 555                 560

Val Gly Gln Asp Gln Thr Leu Ser Pro Gly Ser Lys Gln Glu Ser Pro
                565                 570                 575

Pro Ala Ala Ala Val Arg Pro Phe Thr Pro Gln Pro Ser Lys Asp Thr
                580                 585                 590

Leu Leu Pro Pro Phe Arg Lys Pro Gln Thr Val Ala Ala Ser Ser Ile
            595                 600                 605

Tyr Ser Met Tyr Thr Gln Gln Ala Pro Gly Lys Asn Phe Gln Gln
            610                 615                 620

Ala Val Gln Ser Ala Leu Thr Lys Thr His Thr Arg Gly Pro His Phe
625                 630                 635                 640

Ser Ser Val Tyr Gly Lys Pro Val Ile Ala Ala Gln Asn Gln Gln
                645                 650                 655

Gln His Pro Glu Asn Ile Tyr Ser Asn Ser Gln Gly Lys Pro Gly Ser
        660                 665                 670

Pro Glu Pro Glu Thr Glu Pro Val Ser Ser Val Gln Glu Asn His Glu
            675                 680                 685

Asn Glu Arg Ile Pro Arg Pro Leu Ser Pro Thr Lys Leu Leu Pro Phe
690                 695                 700

Leu Ser Asn Pro Tyr Arg Asn Gln Ser Asp Ala Asp Leu Glu Ala Leu
705                 710                 715                 720

Arg Lys Lys Leu Ser Asn Ala Pro Arg Pro Leu Lys Lys Arg Ser Ser
                725                 730                 735

Ile Thr Glu Pro Glu Gly Pro Asn Gly Pro Asn Ile Gln Lys Leu Leu
            740                 745                 750

Tyr Gln Arg Thr Thr Ile Ala Ala Met Glu Thr Ile Ser Val Pro Ser
            755                 760                 765

Tyr Pro Ser Lys Ser Ala Ser Val Thr Ala Ser Ser Glu Ser Pro Val
    770                 775                 780

Glu Ile Gln Asn Pro Tyr Leu His Val Glu Pro Lys Glu Val Val
785                 790                 795                 800

Ser Leu Val Pro Glu Ser Leu Ser Pro Glu Asp Val Gly Asn Ala Ser
                805                 810                 815

Thr Glu Asn Ser Asp Met Pro Ala Pro Ser Pro Gly Leu Asp Tyr Glu
            820                 825                 830

Pro Glu Gly Val Pro Asp Asn Ser Pro Asn Leu Gln Asn Asn Pro Glu
        835                 840                 845

Glu Pro Asn Pro Glu Ala Pro His Val Leu Asp Val Tyr Leu Glu Glu
850                 855                 860

Tyr Pro Pro Tyr Pro Pro Pro Tyr Pro Ser Gly Glu Pro Glu Gly
865                 870                 875                 880
```

Pro Gly Glu Asp Ser Val Ser Met Arg Pro Glu Ile Thr Gly Gln
           885                 890                 895

Val Ser Leu Pro Pro Gly Lys Arg Thr Asn Leu Arg Lys Thr Gly Ser
       900                 905                 910

Glu Arg Ile Ala His Gly Met Arg Val Lys Phe Asn Pro Leu Ala Leu
       915                 920                 925

Leu Leu Asp Ser Ser Leu Glu Gly Glu Phe Asp Leu Val Gln Arg Ile
   930                 935                 940

Ile Tyr Glu Val Asp Asp Pro Ser Leu Pro Asn Asp Glu Gly Ile Thr
945                 950                 955                 960

Ala Leu His Asn Ala Val Cys Ala Gly His Thr Glu Ile Val Lys Phe
               965                 970                 975

Leu Val Gln Phe Gly Val Asn Val Asn Ala Ala Asp Ser Asp Gly Trp
           980                 985                 990

Thr Pro Leu His Cys Ala Ala Ser Cys Asn Asn Val Gln Val Cys Lys
       995                 1000                1005

Phe Leu Val Glu Ser Gly Ala Ala Val Phe Ala Met Thr Tyr Ser Asp
   1010                1015                1020

Met Gln Thr Ala Ala Asp Lys Cys Glu Glu Met Glu Glu Gly Tyr Thr
1025                1030                1035                1040

Gln Cys Ser Gln Phe Leu Tyr Gly Val Gln Glu Lys Met Gly Ile Met
           1045                1050                1055

Asn Lys Gly Val Ile Tyr Ala Leu Trp Asp Tyr Glu Pro Gln Asn Asp
               1060                1065                1070

Asp Glu Leu Pro Met Lys Glu Gly Asp Cys Met Thr Ile Ile His Arg
       1075                1080                1085

Glu Asp Glu Asp Glu Ile Glu Trp Trp Trp Ala Arg Leu Asn Asp Lys
   1090                1095                1100

Glu Gly Tyr Val Pro Arg Asn Leu Leu Gly Leu Tyr Pro Arg Ile Lys
1105                1110                1115                1120

Pro Arg Gln Arg Ser Leu Ala
           1125

<210> SEQ ID NO 18
<211> LENGTH: 7667
<212> TYPE: DNA
<213> ORGANISM: Homo sapiens
<220> FEATURE:
<221> NAME/KEY: CDS
<222> LOCATION: (98)..(2455)

<400> SEQUENCE: 18
gtccgggttc gcttgcctcg tcagcgtccg cgttttttccc ggcccccccc aaccccccg      60 gacaggaccc ccttgagctt gtccctcagc tgccacc atg agc gac caa gat cac     115
                                        Met Ser Asp Gln Asp His
                                          1               5 tcc atg gat gaa atg aca gct gtg gtg aaa att gaa aaa gga gtt ggt     163
Ser Met Asp Glu Met Thr Ala Val Val Lys Ile Glu Lys Gly Val Gly
       10                  15                  20 ggc aat aat ggg ggc aat ggt aat ggt ggt ggt gcc ttt tca cag gct     211
Gly Asn Asn Gly Gly Asn Gly Asn Gly Gly Gly Ala Phe Ser Gln Ala
   25                  30                  35 cga agt agc agc aca ggc agt agc agc act gga gga gga ggg cag        259
Arg Ser Ser Ser Thr Gly Ser Ser Ser Thr Gly Gly Gly Gln
40                  45                  50 gag tcc cag cca tcc cct ttg gct ctg ctg gca gca act tgc agc aga     307
Glu Ser Gln Pro Ser Pro Leu Ala Leu Leu Ala Ala Thr Cys Ser Arg

```
                55                      60                      65                      70
att gag tca ccc aat gag aac agc aac aac tcc cag ggc ccg agt cag        355
Ile Glu Ser Pro Asn Glu Asn Ser Asn Asn Ser Gln Gly Pro Ser Gln
                    75                      80                      85 tca ggg gga aca ggt gag ctt gac ctc aca gcc aca caa ctt tca cag        403
Ser Gly Gly Thr Gly Glu Leu Asp Leu Thr Ala Thr Gln Leu Ser Gln
                    90                      95                     100 ggt gcc aat ggc tgg cag atc atc tct tcc tcc tct ggg gct acc cct        451
Gly Ala Asn Gly Trp Gln Ile Ile Ser Ser Ser Ser Gly Ala Thr Pro
                   105                     110                     115 acc tca aag gaa cag agt ggc agc agt acc aat ggc agc aat ggc agt        499
Thr Ser Lys Glu Gln Ser Gly Ser Ser Thr Asn Gly Ser Asn Gly Ser
                   120                     125                     130 gag tct tcc aag aat cgc aca gtc tct ggt ggg cag tat gtt gtg gct        547
Glu Ser Ser Lys Asn Arg Thr Val Ser Gly Gly Gln Tyr Val Val Ala
135                     140                     145                     150 gcc gct ccc aac tta cag aac cag caa gtt ctg aca gga cta cct gga        595
Ala Ala Pro Asn Leu Gln Asn Gln Gln Val Leu Thr Gly Leu Pro Gly
                   155                     160                     165 gtg atg cct aat att cag tat caa gta atc cca cag ttc cag acc gtt        643
Val Met Pro Asn Ile Gln Tyr Gln Val Ile Pro Gln Phe Gln Thr Val
                   170                     175                     180 gat ggg caa cag ctg cag ttt gct gcc act ggg gcc caa gtg cag cag        691
Asp Gly Gln Gln Leu Gln Phe Ala Ala Thr Gly Ala Gln Val Gln Gln
                   185                     190                     195 gat ggt tct ggt caa ata cag atc ata cca ggt gca aac caa cag att        739
Asp Gly Ser Gly Gln Ile Gln Ile Ile Pro Gly Ala Asn Gln Gln Ile
                   200                     205                     210 atc aca aat cga gga agt gga ggc aac atc att gct gct atg cca aac        787
Ile Thr Asn Arg Gly Ser Gly Gly Asn Ile Ile Ala Ala Met Pro Asn
215                     220                     225                     230 cta ctc cag cag gct gtc ccc ctc caa ggc ctg gct aat aat gta ctc        835
Leu Leu Gln Gln Ala Val Pro Leu Gln Gly Leu Ala Asn Asn Val Leu
                   235                     240                     245 tca gga cag act cag tat gtg acc aat gta cca gtg gcc ctg aat ggg        883
Ser Gly Gln Thr Gln Tyr Val Thr Asn Val Pro Val Ala Leu Asn Gly
                   250                     255                     260 aac atc acc ttg cta cct gtc aac agc gtt tct gca gct acc ttg act        931
Asn Ile Thr Leu Leu Pro Val Asn Ser Val Ser Ala Ala Thr Leu Thr
                   265                     270                     275 ccc agc tct cag gca gtc acg atc agc agc tct ggg tcc cag gag agt        979
Pro Ser Ser Gln Ala Val Thr Ile Ser Ser Ser Gly Ser Gln Glu Ser
                   280                     285                     290 ggc tca cag cct gtc acc tca ggg act acc atc agt tct gcc agc ttg       1027
Gly Ser Gln Pro Val Thr Ser Gly Thr Thr Ile Ser Ser Ala Ser Leu
295                     300                     305                     310 gta tca tca caa gcc agt tcc agc tcc ttt ttc acc aat gcc aat agc       1075
Val Ser Ser Gln Ala Ser Ser Ser Ser Phe Phe Thr Asn Ala Asn Ser
                   315                     320                     325 tac tca act act act acc acc agc aac atg gga att atg aac ttt act       1123
Tyr Ser Thr Thr Thr Thr Thr Ser Asn Met Gly Ile Met Asn Phe Thr
                   330                     335                     340 acc agt gga tca tca ggg acc aac tct caa ggc cag aca ccc cag agg       1171
Thr Ser Gly Ser Ser Gly Thr Asn Ser Gln Gly Gln Thr Pro Gln Arg
                   345                     350                     355 gtc agt ggg cta cag ggg tct gat gct ctg aac atc cag caa aac cag       1219
Val Ser Gly Leu Gln Gly Ser Asp Ala Leu Asn Ile Gln Gln Asn Gln
                   360                     365                     370 aca tct gga ggc tca ttg caa gca ggc cag caa aaa gaa gga gag caa       1267
```

```
            Thr Ser Gly Gly Ser Leu Gln Ala Gly Gln Gln Lys Glu Gly Glu Gln
            375             380                 385                 390 aac cag cag aca cag cag caa caa att ctt atc cag cct cag cta gtt      1315
Asn Gln Gln Thr Gln Gln Gln Gln Ile Leu Ile Gln Pro Gln Leu Val
                395                 400                 405 caa ggg gga cag gcc ctc cag gcc ctc caa gca gca cca ttg tca ggg      1363
Gln Gly Gly Gln Ala Leu Gln Ala Leu Gln Ala Ala Pro Leu Ser Gly
                410                 415                 420 cag acc ttt aca act caa gcc atc tcc cag gaa acc ctc cag aac ctc      1411
Gln Thr Phe Thr Thr Gln Ala Ile Ser Gln Glu Thr Leu Gln Asn Leu
            425                 430                 435 cag ctt cag gct gtt cca aac tct ggt ccc atc atc atc cgg aca cca      1459
Gln Leu Gln Ala Val Pro Asn Ser Gly Pro Ile Ile Ile Arg Thr Pro
        440                 445                 450 aca gtg ggg ccc aat gga cag gtc agt tgg cag act cta cag ctg cag      1507
Thr Val Gly Pro Asn Gly Gln Val Ser Trp Gln Thr Leu Gln Leu Gln
455                 460                 465                 470 aac ctc caa gtt cag aac cca caa gcc caa aca atc acc tta gcc cca      1555
Asn Leu Gln Val Gln Asn Pro Gln Ala Gln Thr Ile Thr Leu Ala Pro
                475                 480                 485 atg cag ggt gtt tcc ttg ggg cag acc agc agc agc aac acc act ctc      1603
Met Gln Gly Val Ser Leu Gly Gln Thr Ser Ser Ser Asn Thr Thr Leu
                490                 495                 500 aca ccc att gcc tca gct gct tcc att cct gct ggc aca gtc act gtg      1651
Thr Pro Ile Ala Ser Ala Ala Ser Ile Pro Ala Gly Thr Val Thr Val
            505                 510                 515 aat gct gct caa ctc tcc tcc atg cca ggc ctc cag acc att aac ctc      1699
Asn Ala Ala Gln Leu Ser Ser Met Pro Gly Leu Gln Thr Ile Asn Leu
520                 525                 530 agt gca ttg ggt act tca gga atc cag gtg cac cca att caa ggc ctg      1747
Ser Ala Leu Gly Thr Ser Gly Ile Gln Val His Pro Ile Gln Gly Leu
535                 540                 545                 550 ccg ttg gct ata gca aat gcc cca ggt gat cat gga gct cag ctt ggt      1795
Pro Leu Ala Ile Ala Asn Ala Pro Gly Asp His Gly Ala Gln Leu Gly
                555                 560                 565 ctc cat ggg gct ggt ggt gat gga ata cat gat gac aca gca ggt gga      1843
Leu His Gly Ala Gly Gly Asp Gly Ile His Asp Asp Thr Ala Gly Gly
                570                 575                 580 gag gaa gga gaa aac agc cca gat gcc caa ccc caa gcc ggt cgg agg      1891
Glu Glu Gly Glu Asn Ser Pro Asp Ala Gln Pro Gln Ala Gly Arg Arg
            585                 590                 595 acc cgg cgg gaa gca tgc acc tgc ccc tac tgt aaa gac agt gaa gga      1939
Thr Arg Arg Glu Ala Cys Thr Cys Pro Tyr Cys Lys Asp Ser Glu Gly
        600                 605                 610 agg ggc tcg ggg gat cct ggc aaa aag aaa cag cat att tgc cac atc      1987
Arg Gly Ser Gly Asp Pro Gly Lys Lys Lys Gln His Ile Cys His Ile
615                 620                 625                 630 caa ggc tgt ggg aaa gtg tat ggc aag acc tct cac ctg cgg gca cac      2035
Gln Gly Cys Gly Lys Val Tyr Gly Lys Thr Ser His Leu Arg Ala His
                635                 640                 645 ttg cgc tgg cat aca ggc gag agg cca ttt atg tgt acc tgg tca tac      2083
Leu Arg Trp His Thr Gly Glu Arg Pro Phe Met Cys Thr Trp Ser Tyr
                650                 655                 660 tgt ggg aaa cgc ttc aca cgt tcg gat gag cta cag agg cac aaa cgt      2131
Cys Gly Lys Arg Phe Thr Arg Ser Asp Glu Leu Gln Arg His Lys Arg
            665                 670                 675 aca cac aca ggt gag aag aaa ttt gcc tgc cct gag tgt cct aag cgc      2179
Thr His Thr Gly Glu Lys Lys Phe Ala Cys Pro Glu Cys Pro Lys Arg
    680                 685                 690
```

```
ttc atg agg agt gac cac ctg tca aaa cat atc aag acc cac cag aat    2227
Phe Met Arg Ser Asp His Leu Ser Lys His Ile Lys Thr His Gln Asn
695                 700                 705                 710 aag aag gga ggc cca ggt gta gct ctg agt gtg ggc act ttg ccc ctg    2275
Lys Lys Gly Gly Pro Gly Val Ala Leu Ser Val Gly Thr Leu Pro Leu
            715                 720                 725 gac agt ggg gca ggt tca gaa ggc agt ggc act gcc act cct tca gcc    2323
Asp Ser Gly Ala Gly Ser Glu Gly Ser Gly Thr Ala Thr Pro Ser Ala
        730                 735                 740 ctt att acc acc aat atg gta gcc atg gag gcc atc tgt cca gag ggc    2371
Leu Ile Thr Thr Asn Met Val Ala Met Glu Ala Ile Cys Pro Glu Gly
    745                 750                 755 att gcc cgt ctt gcc aac agt ggc atc aac gtc atg cag gtg gca gat    2419
Ile Ala Arg Leu Ala Asn Ser Gly Ile Asn Val Met Gln Val Ala Asp
760                 765                 770 ctg cag tcc att aat atc agt ggc aat ggc ttc tga gatcaggcac         2465
Leu Gln Ser Ile Asn Ile Ser Gly Asn Gly Phe
775                 780                 785 ccggggccag agacatatgg ccataccccc ttaaccccgg gatgcaaggt agcatgggtc   2525
caagagacat ggaagagaga gccatgaagc attaaaatgc atggtgttga agaatcag    2585
gagagggata caagagagga gatggggtcc cggcacccat ctgtatcatc agtgcctctt   2645
tgaaggtggg aaacattagt gaaaattctg ttggtgccac gctttgatga gcatttgttt   2705
gaccccagtt tcttcttaca cttcttaccc cagcctaccc ttcctgcatt tctcttctca   2765
gctcttccat gatggattcc ccccctttc ctaaagccat catgccttga taaatatata    2825
tgatcattga aatactttt aacaaaaaac agattctata ttattatata tatatatata   2885
tatataaaga tatatagaga tgcattcaca ggggttggct gggaggagga agaccattct   2945
gtgaccaaaa taccttggtc attttttta tattgcctta tttccctatg gctgagcctt    3005
gttgtgacac atcaagcttt tctgtagatg ttgtcttggc ttcccaccag cttaagcgtt   3065
catatgctct gcttttagtt catatataca tacataatgt ttttcctttc ttaattttgt   3125
cttttttgttt gggatcagct tcttgcactc cttccctaac tcaactgttg ccgtctcatc   3185
ttctctcatc tgatcacttc atgttttgtt tttgttactg cctggatgag gcacttctgt   3245
caatttttc aggaccttag ttccagcagc agaatggaaa aatccttgaa gcccaggctg   3305
atgcttgaag taactgtgga gggagtgttc aaaatactac tgacgcaggc accttcttgg   3365
cgctggagag tcaaaggcat ctcccttcat tagctgctct gagcatcaag aattagaagt   3425
ctttcagtgg aattgtacaa gagtcccttt gaagataata atcttggctc agtttgtata   3485
aactgtcaaa ttttcaaata ataggtaggg ggctttcact aggaaaatca tgtgctcaga   3545
agaggaaatg actcgtagtc aggttcagga gttagtggga tatttggact ttggtactgc   3605
tgtcttccaa ggtagctcta agttttgatg tgtgggcttc tgagtttata ttctgaaagg   3665
aaatacactt cttttgaaca tccccactag gttcttttcc attgtcaata aggagcatca   3725
gccagtgaat ctgtttcagg tttccattct gcagaactcc tccaaagcat gtgctagtgg   3785
caagacagtg gttcttatga tgttttccct taacttttcc ttgtatgttc ttgggtggtt   3845
cctaagggaa agggaagcac atgatcatgg gaatgatagc ccagaacaaa agaaatctt   3905
gtcttaccac agtgttttat aggagagatt gggagaaatc atcctgtttt ctctgtgacc   3965
tgatttcaga agagactgat ccaaaaatta taacggcagg gaacctagtg catttggcac   4025
tgagatttaa atgcaaccag aattgtcctc aaggcccagc cataaaagca ttgtctctct   4085
cgaccttctg gtatcttgtt agagagcttt tcactgtgag gaagtgtgga aaaatagctc   4145
```

-continued

```
tgtgtgtgtg tgtgtgtgtg tgtgtgtgtg tgtgtgtaat ctgttaggtt ggggataggt    4205
tttctgctag ccaatattaa aagagacctg caataaaaaa attaccctga tctgatagaa    4265
agcaagtgtt tttgtatgtg tgggtgaatg tgtgttcatg cccgtatatg tctacacaca    4325
gatgacaaat tatatttgaa atcgttggaa aataaattca gatcaaaatg cctttcaggc    4385
ccattaccta gaaatctatc ttaaaacctg ggtatgttcc taaggtcatt tctttgctta    4445
tgctaaatta attacaatta tgaatggagg atattctact gtacttttt aaaaagaaac    4505 tattttttgtg tttgaaagtg aaaccaacat ccagatctat agcagagtcc ttattcttct    4565
cataaatctt tttactttgg ctacaaatag atgatggtat gattctatta tatattttat    4625
ataaaatcca tccaaattaa gttttgggta agtgtgttgt ttaatctgaa ctatagtaac    4685
ttaatactct aaacaatagt tcactccatt tggtcctttc tccacagatg taattatgtt    4745
ttcaactcag gaactatggc aaggaacttt ccccagatca aattctatta acgctgagat    4805
acaagtcatc catgcacagc cactatcata ccctttattc tcactgaaag gcagaactca    4865
gaacctgtta ttttatgtct gtaatcatgt actttggcat cttttggagg aaaggggcag    4925
gataactcac tggaatgtac agtattttgc tagtgcattt caaggaatgg aatcttctcc    4985
agtatgaaat taccagatat aaaataatgt aatgatgctg aggatataag cttttagaag    5045
gtaatttgat ggtatttctt tctcgaatga aaagctgctg gtttaccctc aaccctattc    5105
attagcatta ccatgagtga atttatatct aattatttcc acttgccctg ttctcttcac    5165
accaaggaag ctccagatcc agtatcttgt ttggcctcaa aacagaagca gcttcttttg    5225
tctcccagca gtagtgagcc actcagtctc ttccacagga agtttggagc ctacattcct    5285
tgagtcagga gcttattaca gaaaaacccc gtttccctga acttttggct aacagaaatt    5345
aatttaactg acatgcatat tgattctgaa attttttttcc taagtttttt tcattttttt    5405
gaatgagttt tttaaatttt ttagatgacc aaaacttgca gggcagggga tgcccagaag    5465
agtggtgaga tagtaaaaca cttattccct catcctttca ggttttcagg ttgcccattt    5525
atattcattt acatgtcatt tgactgtctc acttttacc cagaacagta acaacccaca    5585
ccgtcttcct tcagggattt ccaactggca ctctgtgggt gctacacaga atgcaattta    5645
atggatattt ctcagcctgg ttcagaataa attgatcctt tgatcccaga aagtatatac    5705
tgaagtgtgg gataaagatt atgattaggg gagggttgga gacaaaagct gtaaattact    5765
atggctgatt tatttctact atatacatat atatttttg cttttgtata tcctatatag    5825
gaaactaagc attgtatttt ttttaacaaa tctaaaaaag cactatgaac tacaggtgtt    5885
tgactttcaa aatatatttt gtattgttaa tatcttcaca ttgtgtgaat actggaagct    5945
gcagatcttt gctaggacgc aataaattta tatactttt gaggggttct tctgggtgc     6005 taatcaggcc cctgttatgc ttagggggag ccctggtgct acttgcttga agttttcagt    6065
gtaagtaccc tgatgccttt tggaccttgg gatcagatca agagttttgg agatcaggta    6125
ccaaggaaat aaggacagtc tagctgcctc aagtgagggg ccctttgcat agctctcctt    6185 cccctcact gaagctgggt agcctattgg ggttgagagg aaaatgtga aatctcagaa     6245 tttatctccc ttagaagaga gccagtaact tatgtacaag gatgaaagaa aggtcgcagc    6305
agtagctttg gggaaaggga ggaagatatg gcacttctcc aaccccggaa acattgctt     6365 ttgaaaactg ctgataaaat atgagccggt tattacttct gtttgggaga ctgtgctctc    6425
tgtggtgcct ctcttggctc tactccacag ataccagacc tcttctaaga ggatgagcag    6485
```

-continued

```
accagctttg aggttgacct gtttctcttt gtctgccttc ccaaaacacc agcccccagg   6545
aagacattaa gcagccttaa gcttaaattc ctactccctc ttccaaattt ggctcacttg   6605
ccttagatcc aaggcaggga aaggaaaaga agggggtct ctggctttat tactcccta    6665 agtctttact ctgacttccc caaacccaga aagattttct ccacagtgtt catttgaaag   6725
aggagtattt tgtcccattt tccccttcct cattatcaaa cagccccagt cttccttgtc   6785
tctgctaaga aagtagaggc atgatgatct gcctctcaac tgcctaagt cctagctaag    6845 tatcagggga aaaaaaaaa aaaaaagcct aacaaatggg attagactag ggctgcaagt   6905
agtgaggatt ttgttgatac ctctgctggg atgtgtgctt tcccatatct tgccttcagg   6965
aattacactg tgccttttcc ccagggatat gggctctgtc tacccagtgc tccagtttcc   7025
cggtaactgc tcttgaacat tgtggacaag ggcaggtctt catattttg atcatccctt    7085 tctcccagtg aaatcccata gcccttacct agagtctagg gcacaaagac ttcggggaag   7145
atacactgag attgacctga ggagacatct acacacacca gtggcagctg ccccagggcc   7205
tgcttcccct tcctaagtct gtcatcctct ggaagggatg ggtggtgctc caatctctgg   7265
tgcctaaaaa cccaagttta tttctctctt aacactggca ataaccagtc cacaccactg   7325
ttgcctttta aaacctctta ataatctcat gctgtgtttg ttttgattcc aatccaatta   7385
tcaccagggc tgtgtgggta aatgctttta aatgctctct catcttgttc ttcccctca    7445 cccccactc ttaggtatgt atgatgctaa tcttgtccct aagtaagttt cttcctgctc    7505
cttttgtatc ttcctttctt gtctttcctc ctacctttg tctcttggtg ttttgggact    7565
tttttttttt tttttttggc cttttgtaca aagattagtt tcaatgtagt ctgtagcctc   7625
ctttgtaaac caattaaaaa gttttttaat aaaaaaaaaa aa                     7667
```

<210> SEQ ID NO 19
<211> LENGTH: 785
<212> TYPE: PRT
<213> ORGANISM: Homo sapiens

<400> SEQUENCE: 19

Met Ser Asp Gln Asp His Ser Met Asp Glu Met Thr Ala Val Val Lys
1               5                   10                  15

Ile Glu Lys Gly Val Gly Gly Asn Asn Gly Gly Asn Gly Asn Gly Gly
            20                  25                  30

Gly Ala Phe Ser Gln Ala Arg Ser Ser Thr Gly Ser Ser Ser Ser
        35                  40                  45

Thr Gly Gly Gly Gly Gln Glu Ser Gln Pro Ser Pro Leu Ala Leu Leu
    50                  55                  60

Ala Ala Thr Cys Ser Arg Ile Glu Ser Pro Asn Glu Asn Ser Asn Asn
65                  70                  75                  80

Ser Gln Gly Pro Ser Gln Ser Gly Gly Thr Gly Glu Leu Asp Leu Thr
                85                  90                  95

Ala Thr Gln Leu Ser Gln Gly Ala Asn Gly Trp Gln Ile Ile Ser Ser
            100                 105                 110

Ser Ser Gly Ala Thr Pro Thr Ser Lys Glu Gln Ser Gly Ser Ser Thr
        115                 120                 125

Asn Gly Ser Asn Gly Ser Glu Ser Ser Lys Asn Arg Thr Val Ser Gly
    130                 135                 140

Gly Gln Tyr Val Val Ala Ala Ala Pro Asn Leu Gln Asn Gln Gln Val
145                 150                 155                 160

Leu Thr Gly Leu Pro Gly Val Met Pro Asn Ile Gln Tyr Gln Val Ile

-continued

```
              165                 170                 175
Pro Gln Phe Gln Thr Val Asp Gly Gln Gln Leu Gln Phe Ala Ala Thr
            180                 185                 190
Gly Ala Gln Val Gln Gln Asp Gly Ser Gly Gln Ile Gln Ile Ile Pro
            195                 200                 205
Gly Ala Asn Gln Gln Ile Ile Thr Asn Arg Gly Ser Gly Gly Asn Ile
            210                 215                 220
Ile Ala Ala Met Pro Asn Leu Leu Gln Gln Ala Val Pro Leu Gln Gly
225                 230                 235                 240
Leu Ala Asn Asn Val Leu Ser Gly Gln Thr Gln Tyr Val Thr Asn Val
                245                 250                 255
Pro Val Ala Leu Asn Gly Asn Ile Thr Leu Leu Pro Val Asn Ser Val
                260                 265                 270
Ser Ala Ala Thr Leu Thr Pro Ser Ser Gln Ala Val Thr Ile Ser Ser
                275                 280                 285
Ser Gly Ser Gln Glu Ser Gly Ser Gln Pro Val Thr Ser Gly Thr Thr
            290                 295                 300
Ile Ser Ser Ala Ser Leu Val Ser Ser Gln Ala Ser Ser Ser Ser Phe
305                 310                 315                 320
Phe Thr Asn Ala Asn Ser Tyr Ser Thr Thr Thr Thr Ser Asn Met
                325                 330                 335
Gly Ile Met Asn Phe Thr Thr Ser Gly Ser Ser Gly Thr Asn Ser Gln
                340                 345                 350
Gly Gln Thr Pro Gln Arg Val Ser Gly Leu Gln Gly Ser Asp Ala Leu
            355                 360                 365
Asn Ile Gln Gln Asn Gln Thr Ser Gly Gly Ser Leu Gln Ala Gly Gln
            370                 375                 380
Gln Lys Glu Gly Glu Gln Asn Gln Gln Thr Gln Gln Gln Gln Ile Leu
385                 390                 395                 400
Ile Gln Pro Gln Leu Val Gln Gly Gly Gln Ala Leu Gln Ala Leu Gln
                405                 410                 415
Ala Ala Pro Leu Ser Gly Gln Thr Phe Thr Thr Gln Ala Ile Ser Gln
                420                 425                 430
Glu Thr Leu Gln Asn Leu Gln Leu Gln Ala Val Pro Asn Ser Gly Pro
            435                 440                 445
Ile Ile Ile Arg Thr Pro Thr Val Gly Pro Asn Gly Gln Val Ser Trp
            450                 455                 460
Gln Thr Leu Gln Leu Gln Asn Leu Gln Val Gln Asn Pro Gln Ala Gln
465                 470                 475                 480
Thr Ile Thr Leu Ala Pro Met Gln Gly Val Ser Leu Gly Gln Thr Ser
                485                 490                 495
Ser Ser Asn Thr Thr Leu Thr Pro Ile Ala Ser Ala Ala Ser Ile Pro
                500                 505                 510
Ala Gly Thr Val Thr Val Asn Ala Ala Gln Leu Ser Ser Met Pro Gly
                515                 520                 525
Leu Gln Thr Ile Asn Leu Ser Ala Leu Gly Thr Ser Gly Ile Gln Val
            530                 535                 540
His Pro Ile Gln Gly Leu Pro Leu Ala Ile Ala Asn Ala Pro Gly Asp
545                 550                 555                 560
His Gly Ala Gln Leu Gly Leu His Gly Ala Gly Asp Gly Ile His
                565                 570                 575
Asp Asp Thr Ala Gly Gly Glu Glu Gly Glu Asn Ser Pro Asp Ala Gln
            580                 585                 590
```

-continued

```
Pro Gln Ala Gly Arg Arg Thr Arg Arg Glu Ala Cys Thr Cys Pro Tyr
        595                 600                 605

Cys Lys Asp Ser Glu Gly Arg Gly Ser Gly Asp Pro Gly Lys Lys Lys
        610                 615                 620

Gln His Ile Cys His Ile Gln Gly Cys Gly Lys Val Tyr Gly Lys Thr
625                 630                 635                 640

Ser His Leu Arg Ala His Leu Arg Trp His Thr Gly Glu Arg Pro Phe
                645                 650                 655

Met Cys Thr Trp Ser Tyr Cys Gly Lys Arg Phe Thr Arg Ser Asp Glu
            660                 665                 670

Leu Gln Arg His Lys Arg Thr His Thr Gly Glu Lys Lys Phe Ala Cys
        675                 680                 685

Pro Glu Cys Pro Lys Arg Phe Met Arg Ser Asp His Leu Ser Lys His
        690                 695                 700

Ile Lys Thr His Gln Asn Lys Lys Gly Gly Pro Gly Val Ala Leu Ser
705                 710                 715                 720

Val Gly Thr Leu Pro Leu Asp Ser Gly Ala Gly Ser Glu Gly Ser Gly
                725                 730                 735

Thr Ala Thr Pro Ser Ala Leu Ile Thr Thr Asn Met Val Ala Met Glu
            740                 745                 750

Ala Ile Cys Pro Glu Gly Ile Ala Arg Leu Ala Asn Ser Gly Ile Asn
        755                 760                 765

Val Met Gln Val Ala Asp Leu Gln Ser Ile Asn Ile Ser Gly Asn Gly
        770                 775                 780

Phe
785

<210> SEQ ID NO 20
<211> LENGTH: 2415
<212> TYPE: DNA
<213> ORGANISM: Homo sapiens
<220> FEATURE:
<221> NAME/KEY: CDS
<222> LOCATION: (263)..(1894)

<400> SEQUENCE: 20
cttggggagc cgccgccgcc atccgccgcc gcagccagct tccgccgccg caggaccggc      60
ccctgcccca gcctccgcag ccgcggcgcg tccacgcccg cccgcgccca gggcgagtcg     120
gggtcgccgc tgcacgcgtt ctcagtgttc cccgcgcccc gcatgtaacc cggccaggcc     180
cccgcaactg tgtcccctgc agctccagcc ccgggctgca ccccccgcc ccgacaccag     240 ctctccagcc tgctcgtcca gg atg gcc gcg gcc aag gcc gag atg cag ctg     292
                        Met Ala Ala Ala Lys Ala Glu Met Gln Leu
                          1               5                  10 atg tcc ccg ctg cag atc tct gac ccg ttc gga tcc ttt cct cac tcg     340
Met Ser Pro Leu Gln Ile Ser Asp Pro Phe Gly Ser Phe Pro His Ser
             15                  20                  25 ccc acc atg gac aac tac cct aag ctg gag gag atg atg ctg ctg agc     388
Pro Thr Met Asp Asn Tyr Pro Lys Leu Glu Glu Met Met Leu Leu Ser
         30                  35                  40 aac ggg gct ccc cag ttc ctc ggc gcc gcc ggg gcc cca gag ggc agc     436
Asn Gly Ala Pro Gln Phe Leu Gly Ala Ala Gly Ala Pro Glu Gly Ser
     45                  50                  55 ggc agc aac agc agc agc agc agc ggg ggc ggt gga ggc ggc ggg           484
Gly Ser Asn Ser Ser Ser Ser Ser Gly Gly Gly Gly Gly Gly
 60                  65                  70
```

```
ggc ggc agc aac agc agc agc agc agc acc ttc aac cct cag gcg    532
Gly Gly Ser Asn Ser Ser Ser Ser Ser Thr Phe Asn Pro Gln Ala
 75              80                  85                  90 gac acg ggc gag cag ccc tac gag cac ctg acc gca gag tct ttt cct    580
Asp Thr Gly Glu Gln Pro Tyr Glu His Leu Thr Ala Glu Ser Phe Pro
                 95                 100                 105 gac atc tct ctg aac aac gag aag gtg ctg gtg gag acc agt tac ccc    628
Asp Ile Ser Leu Asn Asn Glu Lys Val Leu Val Glu Thr Ser Tyr Pro
                110                 115                 120 agc caa acc act cga ctg ccc ccc atc acc tat act ggc cgc ttt tcc    676
Ser Gln Thr Thr Arg Leu Pro Pro Ile Thr Tyr Thr Gly Arg Phe Ser
            125                 130                 135 ctg gag cct gca ccc aac agt ggc aac acc ttg tgg ccc gag ccc ctc    724
Leu Glu Pro Ala Pro Asn Ser Gly Asn Thr Leu Trp Pro Glu Pro Leu
140                 145                 150 ttc agc ttg gtc agt ggc cta gtg agc atg acc aac cca ccg gcc tcc    772
Phe Ser Leu Val Ser Gly Leu Val Ser Met Thr Asn Pro Pro Ala Ser
155                 160                 165                 170 tcg tcc tca gca cca tct cca gcg gcc tcc tcc gcc tcc gcc tcc cag    820
Ser Ser Ser Ala Pro Ser Pro Ala Ala Ser Ser Ala Ser Ala Ser Gln
                175                 180                 185 agc cca ccc ctg agc tgc gca gtg cca tcc aac gac agc agt ccc att    868
Ser Pro Pro Leu Ser Cys Ala Val Pro Ser Asn Asp Ser Ser Pro Ile
                190                 195                 200 tac tca gcg gca ccc acc ttc ccc acg ccg aac act gac att ttc cct    916
Tyr Ser Ala Ala Pro Thr Phe Pro Thr Pro Asn Thr Asp Ile Phe Pro
            205                 210                 215 gag cca caa agc cag gcc ttc ccg ggc tcg gca ggg aca gcg ctc cag    964
Glu Pro Gln Ser Gln Ala Phe Pro Gly Ser Ala Gly Thr Ala Leu Gln
        220                 225                 230 tac ccg cct cct gcc tac cct gcc gcc aag ggt ggc ttc cag gtt ccc   1012
Tyr Pro Pro Pro Ala Tyr Pro Ala Ala Lys Gly Gly Phe Gln Val Pro
235                 240                 245                 250 atg atc ccc gac tac ctg ttt cca cag cag cag ggg gat ctg ggc ctg   1060
Met Ile Pro Asp Tyr Leu Phe Pro Gln Gln Gln Gly Asp Leu Gly Leu
                255                 260                 265 ggc acc cca gac cag aag ccc ttc cag ggc ctg gag agc cgc acc cag   1108
Gly Thr Pro Asp Gln Lys Pro Phe Gln Gly Leu Glu Ser Arg Thr Gln
                270                 275                 280 cag cct tcg cta acc cct ctg tct act att aag gcc ttt gcc act cag   1156
Gln Pro Ser Leu Thr Pro Leu Ser Thr Ile Lys Ala Phe Ala Thr Gln
            285                 290                 295 tcg ggc tcc cag gac ctg aag gcc ctc aat acc agc tac cag tcc cag   1204
Ser Gly Ser Gln Asp Leu Lys Ala Leu Asn Thr Ser Tyr Gln Ser Gln
        300                 305                 310 ctc atc aaa ccc agc cgc atg cgc aag tac ccc aac cgg ccc agc aag   1252
Leu Ile Lys Pro Ser Arg Met Arg Lys Tyr Pro Asn Arg Pro Ser Lys
315                 320                 325                 330 acg ccc ccc cac gaa cgc cct tac gct tgc cca gtg gag tcc tgt gat   1300
Thr Pro Pro His Glu Arg Pro Tyr Ala Cys Pro Val Glu Ser Cys Asp
                335                 340                 345 cgc cgc ttc tcc cgc tcc gac gag ctc acc cgc cac atc cgc atc cac   1348
Arg Arg Phe Ser Arg Ser Asp Glu Leu Thr Arg His Ile Arg Ile His
                350                 355                 360 aca ggc cag aag ccc ttc cag tgc cgc atc tgc atg cgc aac ttc agc   1396
Thr Gly Gln Lys Pro Phe Gln Cys Arg Ile Cys Met Arg Asn Phe Ser
            365                 370                 375 cgc agc gac cac ctc acc acc cac atc cgc acc cac aca ggc gaa aag   1444
Arg Ser Asp His Leu Thr Thr His Ile Arg Thr His Thr Gly Glu Lys
380                 385                 390
```

```
ccc ttc gcc tgc gac atc tgt gga aga aag ttt gcc agg agc gat gaa    1492
Pro Phe Ala Cys Asp Ile Cys Gly Arg Lys Phe Ala Arg Ser Asp Glu
395                 400                 405                 410 cgc aag agg cat acc aag atc cac ttg cgg cag aag gac aag aaa gca    1540
Arg Lys Arg His Thr Lys Ile His Leu Arg Gln Lys Asp Lys Lys Ala
            415                 420                 425 gac aaa agt gtt gtg gcc tct tcg gcc acc tcc tct ctc tct tcc tac    1588
Asp Lys Ser Val Val Ala Ser Ser Ala Thr Ser Ser Leu Ser Ser Tyr
        430                 435                 440 ccg tcc ccg gtt gct acc tct tac ccg tcc ccg gtt act acc tct tat    1636
Pro Ser Pro Val Ala Thr Ser Tyr Pro Ser Pro Val Thr Thr Ser Tyr
    445                 450                 455 cca tcc ccg gcc acc acc tca tac cca tcc cct gtg ccc acc tcc ttc    1684
Pro Ser Pro Ala Thr Thr Ser Tyr Pro Ser Pro Val Pro Thr Ser Phe
460                 465                 470 tcc tct ccc ggc tcc tcg acc tac cca tcc cct gtg cac agt ggc ttc    1732
Ser Ser Pro Gly Ser Ser Thr Tyr Pro Ser Pro Val His Ser Gly Phe
475                 480                 485                 490 ccc tcc ccg tcg gtg gcc acc acg tac tcc tct gtt ccc cct gct ttc    1780
Pro Ser Pro Ser Val Ala Thr Thr Tyr Ser Ser Val Pro Pro Ala Phe
            495                 500                 505 ccg gcc cag gtc agc agc ttc cct tcc tca gct gtc acc aac tcc ttc    1828
Pro Ala Gln Val Ser Ser Phe Pro Ser Ser Ala Val Thr Asn Ser Phe
        510                 515                 520 agc gcc tcc aca ggg ctt tcg gac atg aca gca acc ttt tct ccc agg    1876
Ser Ala Ser Thr Gly Leu Ser Asp Met Thr Ala Thr Phe Ser Pro Arg
    525                 530                 535 aca att gaa att tgc taa agggaaggg gaagaaagg gaaagggag              1924
Thr Ile Glu Ile Cys
    540 aaaaagaaac acaagagact taaaggacag gaggaggaga tggccatagg agaggagggt  1984 tcctcttagg tcagatggag gttctcagag ccaagtcctc cctctctact ggagtggaag  2044 gtctattggc caacaatcct ttctgcccac ttccccttcc ccaattacta ttcccttcga  2104 cttcagctgc ctgaaacagc catgtccaag ttcttcacct ctatccaaag aacttgattt  2164 gcatggattt tggataaatc atttcagtat catctccatc atatgcctga ccccttgctc  2224 ccttcaatgc tagaaaatcg agttggcaaa atggggtttg ggcccctcag agccctgccc  2284 tgcacccttg tacagtgtct gtgccatgga tttcgttttt cttggggtac tcttgatgtg  2344 aagataattt gcatattcta ttgtattatt tggagttagg tcctcacttg ggggaaaaaa  2404 aaaaaaaaaa a                                                      2415

<210> SEQ ID NO 21
<211> LENGTH: 543
<212> TYPE: PRT
<213> ORGANISM: Homo sapiens

<400> SEQUENCE: 21

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60
```

```
Ser Ser Ser Gly Gly Gly Gly Gly Gly Gly Ser Asn Ser Ser
 65                  70                  75                  80

Ser Ser Ser Ser Thr Phe Asn Pro Gln Ala Asp Thr Gly Glu Gln Pro
             85                  90                  95

Tyr Glu His Leu Thr Ala Glu Ser Phe Pro Asp Ile Ser Leu Asn Asn
        100                 105                 110

Glu Lys Val Leu Val Glu Thr Ser Tyr Pro Ser Gln Thr Thr Arg Leu
    115                 120                 125

Pro Pro Ile Thr Tyr Thr Gly Arg Phe Ser Leu Glu Pro Ala Pro Asn
130                 135                 140

Ser Gly Asn Thr Leu Trp Pro Glu Pro Leu Phe Ser Leu Val Ser Gly
145                 150                 155                 160

Leu Val Ser Met Thr Asn Pro Ala Ser Ser Ser Ala Pro Ser
                165                 170                 175

Pro Ala Ala Ser Ser Ala Ser Ala Ser Gln Ser Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
            245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
    275                 280                 285

Leu Ser Thr Ile Lys Ala Phe Ala Thr Gln Ser Gly Ser Gln Asp Leu
290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Glu Leu Thr Arg His Ile Arg Ile His Thr Gly Gln Lys Pro Phe
        355                 360                 365

Gln Cys Arg Ile Cys Met Arg Asn Phe Ser Arg Ser Asp His Leu Thr
    370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
            405                 410                 415

Ile His Leu Arg Gln Lys Asp Lys Lys Ala Asp Lys Ser Val Val Ala
        420                 425                 430

Ser Ser Ala Thr Ser Ser Leu Ser Ser Tyr Pro Ser Pro Val Ala Thr
            435                 440                 445

Ser Tyr Pro Ser Pro Val Thr Thr Ser Tyr Pro Ser Pro Ala Thr Thr
        450                 455                 460

Ser Tyr Pro Ser Pro Val Pro Thr Ser Phe Ser Ser Pro Gly Ser Ser
465                 470                 475                 480

Thr Tyr Pro Ser Pro Val His Ser Gly Phe Pro Ser Pro Ser Val Ala
```

-continued

```
                485                 490                 495
Thr Thr Tyr Ser Ser Val Pro Pro Ala Phe Pro Ala Gln Val Ser Ser
            500                 505                 510

Phe Pro Ser Ser Ala Val Thr Asn Ser Phe Ser Ala Ser Thr Gly Leu
        515                 520                 525

Ser Asp Met Thr Ala Thr Phe Ser Pro Arg Thr Ile Glu Ile Cys
    530                 535                 540

<210> SEQ ID NO 22
<211> LENGTH: 513
<212> TYPE: DNA
<213> ORGANISM: Homo sapiens
<220> FEATURE:
<221> NAME/KEY: CDS
<222> LOCATION: (1)..(513)

<400> SEQUENCE: 22 atg ccg ctg ccc gtt gcg ctg cag acc cgc ttg gcc aag aga ggc atc      48
Met Pro Leu Pro Val Ala Leu Gln Thr Arg Leu Ala Lys Arg Gly Ile
 1               5                  10                  15 ctc aaa cat ctg gag cct gaa cca gag gaa gag atc att gcc gag gac      96
Leu Lys His Leu Glu Pro Glu Pro Glu Glu Glu Ile Ile Ala Glu Asp
            20                  25                  30 tat gac gat gat cct gtg gac tac gag gcc acc agg ttg gag ggc cta     144
Tyr Asp Asp Asp Pro Val Asp Tyr Glu Ala Thr Arg Leu Glu Gly Leu
        35                  40                  45 cca cca agc tgg tac aag gtg ttc gac cct tcc tgc ggg ctc cct tac     192
Pro Pro Ser Trp Tyr Lys Val Phe Asp Pro Ser Cys Gly Leu Pro Tyr
    50                  55                  60 tac tgg aat gca gac aca gac ctt gta tcc tgg ctc tcc cca cat gac     240
Tyr Trp Asn Ala Asp Thr Asp Leu Val Ser Trp Leu Ser Pro His Asp
 65                  70                  75                  80 ccc aac tcc gtg gtt acc aaa tcg gcc aag aag ctc aga agc agt aat     288
Pro Asn Ser Val Val Thr Lys Ser Ala Lys Lys Leu Arg Ser Ser Asn
                85                  90                  95 gca gca gta agc cga aag gat gaa gag tta gac ccc atg gac cct agc     336
Ala Ala Val Ser Arg Lys Asp Glu Glu Leu Asp Pro Met Asp Pro Ser
           100                 105                 110 tca tac tca gac gcc ccc cgg ggc acg tgg tca aca gga ctc ccc aag     384
Ser Tyr Ser Asp Ala Pro Arg Gly Thr Trp Ser Thr Gly Leu Pro Lys
       115                 120                 125 cgg aat gag gcc aag act ggc gct gac acc aca gca gct ggg ccc ctc     432
Arg Asn Glu Ala Lys Thr Gly Ala Asp Thr Thr Ala Ala Gly Pro Leu
   130                 135                 140 ttc cag cag cgg ccg tat cca tcc cca ggg gct gtg ctc cgg gcc aat     480
Phe Gln Gln Arg Pro Tyr Pro Ser Pro Gly Ala Val Leu Arg Ala Asn
145                 150                 155                 160 gca gag gcc tcc cga acc aag cag cag gat tga                         513
Ala Glu Ala Ser Arg Thr Lys Gln Gln Asp
               165                 170

<210> SEQ ID NO 23
<211> LENGTH: 170
<212> TYPE: PRT
<213> ORGANISM: Homo sapiens

<400> SEQUENCE: 23

Met Pro Leu Pro Val Ala Leu Gln Thr Arg Leu Ala Lys Arg Gly Ile
 1               5                  10                  15

Leu Lys His Leu Glu Pro Glu Pro Glu Glu Glu Ile Ile Ala Glu Asp
            20                  25                  30
```

```
Tyr Asp Asp Pro Val Asp Tyr Glu Ala Thr Arg Leu Glu Gly Leu
            35                  40                  45

Pro Pro Ser Trp Tyr Lys Val Phe Asp Pro Ser Cys Gly Leu Pro Tyr
 50                  55                  60

Tyr Trp Asn Ala Asp Thr Asp Leu Val Ser Trp Leu Ser Pro His Asp
 65                  70                  75                  80

Pro Asn Ser Val Val Thr Lys Ser Ala Lys Lys Leu Arg Ser Ser Asn
                 85                  90                  95

Ala Ala Val Ser Arg Lys Asp Glu Leu Asp Pro Met Asp Pro Ser
            100                 105                 110

Ser Tyr Ser Asp Ala Pro Arg Gly Thr Trp Ser Thr Gly Leu Pro Lys
            115                 120                 125

Arg Asn Glu Ala Lys Thr Gly Ala Asp Thr Thr Ala Ala Gly Pro Leu
130                 135                 140

Phe Gln Gln Arg Pro Tyr Pro Ser Pro Gly Ala Val Leu Arg Ala Asn
145                 150                 155                 160

Ala Glu Ala Ser Arg Thr Lys Gln Gln Asp
            165                 170

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Glu Tyr Pro Pro Tyr Pro Pro Pro Pro Tyr Pro Ser
 1               5                  10

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Gly Leu Pro Pro Ser Trp Tyr Lys Val Phe Asp Pro Ser Cys Gly Leu
 1               5                  10                  15

Pro Tyr Tyr Trp Asn Ala Asp Thr Asp Leu Val Ser Trp Leu Ser Pro
                20                  25                  30

His Asp Pro Asn
            35

<210> SEQ ID NO 26
<211> LENGTH: 846
<212> TYPE: DNA
<213> ORGANISM: Feline immunodeficiency virus
<220> FEATURE:
<221> NAME/KEY: CDS
<222> LOCATION: (1)..(846)

<400> SEQUENCE: 26 tcc tcc tgg gtt gaa aga att gaa gaa gca gaa ata aat cat gaa aaa      48
Ser Ser Trp Val Glu Arg Ile Glu Glu Ala Glu Ile Asn His Glu Lys
 1               5                  10                  15 ttt cat tca gat tca cag tac ttg agg act gaa ttt aag tta ccc aga      96
Phe His Ser Asp Ser Gln Tyr Leu Arg Thr Glu Phe Lys Leu Pro Arg
```

```
                    20                  25                  30
atg gtg gct gaa gaa ata aaa aga aaa tgc cct cta tgt aga att aga        144
Met Val Ala Glu Glu Ile Lys Arg Lys Cys Pro Leu Cys Arg Ile Arg
             35                  40                  45 gga gaa cag gtg gga gga caa tta aaa att gga cca gga att tgg caa        192
Gly Glu Gln Val Gly Gly Gln Leu Lys Ile Gly Pro Gly Ile Trp Gln
 50                  55                  60 gtg gat tgc aca cat ttc aat aat aaa ata att ctt gtg gca att cat        240
Val Asp Cys Thr His Phe Asn Asn Lys Ile Ile Leu Val Ala Ile His
 65                  70                  75                  80 gtc gaa tca gga ttc ctt tgg gca caa ata ata cca caa gaa aca gct        288
Val Glu Ser Gly Phe Leu Trp Ala Gln Ile Ile Pro Gln Glu Thr Ala
                 85                  90                  95 gac tgc aca gtc aaa gca ata atg caa ctc cta agt gct cat aat gtt        336
Asp Cys Thr Val Lys Ala Ile Met Gln Leu Leu Ser Ala His Asn Val
            100                 105                 110 aca gaa ctg caa aca gac aat ggg cca aat ttt aga aat caa aaa atg        384
Thr Glu Leu Gln Thr Asp Asn Gly Pro Asn Phe Arg Asn Gln Lys Met
            115                 120                 125 gaa ggt tta ctc aat tac atg gga ata aaa cat aaa ttt gga ata cca        432
Glu Gly Leu Leu Asn Tyr Met Gly Ile Lys His Lys Phe Gly Ile Pro
        130                 135                 140 ggc aac cct caa tct caa gct ttg gtt gaa aat gcc aat aat act tta        480
Gly Asn Pro Gln Ser Gln Ala Leu Val Glu Asn Ala Asn Asn Thr Leu
145                 150                 155                 160 aag tgt tgg att cag aag ttt ttg cct gaa aca aca tct tta gac aat        528
Lys Cys Trp Ile Gln Lys Phe Leu Pro Glu Thr Thr Ser Leu Asp Asn
                165                 170                 175 gct ttg gct ctc gct ctg cat tgc ctt aat ttt aaa caa agg ggt aga        576
Ala Leu Ala Leu Ala Leu His Cys Leu Asn Phe Lys Gln Arg Gly Arg
            180                 185                 190 ata ggg gga atg gcc cca tat gaa tta tta aca caa caa gaa tca tta        624
Ile Gly Gly Met Ala Pro Tyr Glu Leu Leu Thr Gln Gln Glu Ser Leu
        195                 200                 205 aga ata cag gat tat ttt tct caa att cca agc aaa ttg caa agt cag        672
Arg Ile Gln Asp Tyr Phe Ser Gln Ile Pro Ser Lys Leu Gln Ser Gln
    210                 215                 220 tgg att tac tat aaa gat caa aaa gac aaa aat tgg aaa gga cca atg        720
Trp Ile Tyr Tyr Lys Asp Gln Lys Asp Lys Asn Trp Lys Gly Pro Met
225                 230                 235                 240 aga gta gag tat tgg gga caa gga tca gtg tta tta aag gat gaa gag        768
Arg Val Glu Tyr Trp Gly Gln Gly Ser Val Leu Leu Lys Asp Glu Glu
                245                 250                 255 agg gga tat ttt ctt gta cct agg agg cac ata cgg aga gtc cca gaa        816
Arg Gly Tyr Phe Leu Val Pro Arg Arg His Ile Arg Arg Val Pro Glu
            260                 265                 270 ccc tgc act ctt cct gaa ggg gat gag tga                                846
Pro Cys Thr Leu Pro Glu Gly Asp Glu
        275                 280

<210> SEQ ID NO 27
<211> LENGTH: 281
<212> TYPE: PRT
<213> ORGANISM: Feline immunodeficiency virus

<400> SEQUENCE: 27

Ser Ser Trp Val Glu Arg Ile Glu Glu Ala Glu Ile Asn His Glu Lys
 1               5                  10                  15

Phe His Ser Asp Ser Gln Tyr Leu Arg Thr Glu Phe Lys Leu Pro Arg
            20                  25                  30
```

-continued

```
Met Val Ala Glu Glu Ile Lys Arg Lys Cys Pro Leu Cys Arg Ile Arg
            35                  40                  45

Gly Glu Gln Val Gly Gly Gln Leu Lys Ile Gly Pro Gly Ile Trp Gln
        50                  55                  60

Val Asp Cys Thr His Phe Asn Asn Lys Ile Ile Leu Val Ala Ile His
 65              70                  75                      80

Val Glu Ser Gly Phe Leu Trp Ala Gln Ile Ile Pro Gln Glu Thr Ala
                85                  90                  95

Asp Cys Thr Val Lys Ala Ile Met Gln Leu Leu Ser Ala His Asn Val
            100                 105                 110

Thr Glu Leu Gln Thr Asp Asn Gly Pro Asn Phe Arg Asn Gln Lys Met
        115                 120                 125

Glu Gly Leu Leu Asn Tyr Met Gly Ile Lys His Lys Phe Gly Ile Pro
        130                 135                 140

Gly Asn Pro Gln Ser Gln Ala Leu Val Glu Asn Ala Asn Asn Thr Leu
145                 150                 155                 160

Lys Cys Trp Ile Gln Lys Phe Leu Pro Glu Thr Thr Ser Leu Asp Asn
            165                 170                 175

Ala Leu Ala Leu Ala Leu His Cys Leu Asn Phe Lys Gln Arg Gly Arg
            180                 185                 190

Ile Gly Gly Met Ala Pro Tyr Glu Leu Leu Thr Gln Gln Glu Ser Leu
            195                 200                 205

Arg Ile Gln Asp Tyr Phe Ser Gln Ile Pro Ser Lys Leu Gln Ser Gln
210                 215                 220

Trp Ile Tyr Tyr Lys Asp Gln Lys Asp Lys Asn Trp Lys Gly Pro Met
225                 230                 235                 240

Arg Val Glu Tyr Trp Gly Gln Gly Ser Val Leu Leu Lys Asp Glu Glu
                245                 250                 255

Arg Gly Tyr Phe Leu Val Pro Arg Arg His Ile Arg Arg Val Pro Glu
            260                 265                 270

Pro Cys Thr Leu Pro Glu Gly Asp Glu
        275                 280
```